US007709031B2

(12) United States Patent
Greenway et al.

(10) Patent No.: US 7,709,031 B2
(45) Date of Patent: May 4, 2010

(54) ANGIOGENIC AGENTS FROM PLANT EXTRACTS, GALLIC ACID, AND DERIVATIVES

(75) Inventors: Frank L. Greenway, Baton Rouge, LA (US); Zhijun Liu, Baton Rouge, LA (US); Eugene A. Woltering, Kenner, LA (US)

(73) Assignee: Board of Supervisors of Louisiana State University And Agricultural and Mechanical College, Baton Rouge, LA (US)

( * ) Notice: Subject to any disclaimer, the term of this patent is extended or adjusted under 35 U.S.C. 154(b) by 770 days.

(21) Appl. No.: 10/559,091

(22) PCT Filed: May 27, 2004

(86) PCT No.: PCT/US2004/016647

§ 371 (c)(1),
(2), (4) Date: May 8, 2006

(87) PCT Pub. No.: WO2005/000330

PCT Pub. Date: Jan. 6, 2005

(65) Prior Publication Data

US 2007/0031332 A1    Feb. 8, 2007

Related U.S. Application Data

(60) Provisional application No. 60/473,806, filed on May 28, 2003.

(51) Int. Cl.
*A61K 36/00* (2006.01)
*A61K 51/00* (2006.01)
*A61K 39/395* (2006.01)
*A61K 38/21* (2006.01)

(52) U.S. Cl. .................. 424/725; 424/1.69; 424/145.1; 424/85.4

(58) Field of Classification Search ........................ None
See application file for complete search history.

(56) References Cited

U.S. PATENT DOCUMENTS

| 6,220,568 B1 | 4/2001 | Wu ............................ 251/114 |
| 6,440,448 B1 | 8/2002 | Intelisano .................... 424/439 |
| 6,444,236 B1 | 9/2002 | Han ............................ 424/725 |
| 6,524,625 B2 | 2/2003 | Aga ........................ 424/195.1 |
| 6,544,947 B2 | 4/2003 | Holaday et al. ................. 512/2 |
| 7,208,181 B1 * | 4/2007 | King et al. ................... 424/725 |

FOREIGN PATENT DOCUMENTS

EP    727218 / APP    8/1996

OTHER PUBLICATIONS

Health and Healing Fact Sheets (website is http://berryhealth.fst.oregonstate.edu/healing/fact_sheets/blac_raspberry_facts.htm, see article).*

Bicknell, R., "Vascular targeting and the inhibition of angiogenesis," Annals of Oncology, vol. 5, pp. 45-50 (1994).
*Colored Illustrations of Chinese Traditional and Herbal Ordinary Drugs in China*, Wu Jianrong and Qiu Dewen, editors; Guizhou Technology and Science Press, Guiyang, China, 8 pgs. (1993).
Creamer, D. et al., "Overexpression of the angiogenic factor platelet-derived endothelial cell growth factor/thymidine phosphorylase in psoriatic epidermis," Br. J. Dermatol.,vol. 137, pp. 851-855 (1997).
Eerola, A.-K. et al., "Tumour infiltrating lymphocytes in relation to tumour angiogenesis, apoptosis and prognosis in patients with large cell lung carcinoma," Lung Cancer, vol. 26, pp. 73-83 (1999).
Encyclopedia of Traditional Chinese Medicine, Shanghai S&T Press, 47 pgs. (1986).
Gao, F. et al., "19α-hydroxyursane-type triterpene glucosyl esters from the roots of *Rubus suavissimus* S. Lee," Chem. Pharm. Bull., vol. 33, pp. 37-40 (1985).
Gasparini, G, "The rationale and future potential of angiogenesis inhibitors in neoplasia," Drugs, vol. 58, No. 1, pp. 17-33 (1999).
Glick, Z. et al., "Effect of Tannic Acid and Related Compounds on the Absorption and Utilization of Proteins in the Rat," J. Nutrition, vol. 100, No. 5, pp. 516-520 (1970).
Glick, Z. et al., "Food Intake Depression and Other Metabolic Effects of Tannic Acid in the Rat," J. Nutrition, vol. 100, No. 5, pp. 509-515 (1970).
Glick, Z., "Modes of Action of Gallic Acid in Suppressing Food Intake of Rate," J. of Nut., vol. 111, No. 11, pp. 1910-1916 (1981).
Hirono, S. et al, "Sweet and Bitter Diterpene-glucosides from Leaves of *Rubus suavissimus*," Chem. Pharm. Bull., vol. 38, No. 6, pp. 1743-1744 (1990).
Huang, P.-F. et al., "Complex Utilization of *Rubus suavissimus* S. Lee," Guangxi Chemical Industry, vol. 31, No. 2, pp. 24-25 (2002).
Isuzugawa, K. et al., "Different Generation of Inhibitors Against Gallic Acid-induced Apoptosis Produces Different Sensitivity to Gallic Acid," Biol. Pharm. Bull., vol. 24, No. 3, pp. 249-253 (2001).
Kawada, M., "Anti-tumor effect of gallic acid on LL-2 lung cancer cells transplanted in mice," Anticancer Drugs, vol. 12, pp. 847-852 (2001).
Kotaro, U., "Antiallergy action of *Rubus suavissimus*," Shokuhin Kogyo, vol. 40, pp. 52-59 (1997).

(Continued)

*Primary Examiner*—Christopher R Tate
*Assistant Examiner*—Randall Winston
(74) *Attorney, Agent, or Firm*—Bonnie J. Davis; John H. Runnels

(57) ABSTRACT

An extract of Chinese blackberry (*Rubus suavissimus*) has been found to inhibit angiogenesis, and two active fractions isolated. Gallic acid was shown to be one of the active anti-angiogenic compounds by an in vitro human angiogenesis model. Aqueous extracts from other plants either known or found to have gallic acid were also found to have anti-angiogenic activity. Various derivatives of gallic acid were found to inhibit angiogenesis. The extract from Chinese blackberry also slowed the growth of a pancreatic tumor and of corneal neovascularization in rats. Extracts from pomegranate were shown to inhibit angiogenesis in fat tissue. Extracts from *Rubus* spp, and other plants with gallic acid, and gallic acid and its derivatives will be useful for treating various diseases associated with neovascularization, including diabetic retinopathy, psoriasis, tumors, obesity, cancer, rheumatoid arthritis, etc.

31 Claims, 51 Drawing Sheets

OTHER PUBLICATIONS

Liu, D. et al., "Studies on Chemical Constituents from *Tetrastigma hypoglaucum*," Chinese Trad. And Herbal Drugs, vol. 34, No. 1, pp. 4-6 (2003).

Liu, Z. et al., *Encyclopedia of Woody Medicinal Plants of China*, CD-ROM, Academic Services Associates, Inc., Seattle, Washington (2000.

Lu, J. et al., "Differential Effects of Theaflavin Monogallates on Cell Growth, Apoptosis, and *Cox-2* Gene Expression in Cancerous Versus Normal Cells," Cancer Research, vol. 60, pp. 6465-6471 (2000).

Maniotis, A.J. et al., "Vascular Channel Formation by Human Melanoma Cells in Vivo and in Vitro: Vasculogenic Mimicry," Am. J. Pathol., vol. 155, No. 3, pp. 739-752 (1999).

Nakahara, K., "Anti-allergic activity of Tiencha and oolong tea polyphenols," Food Style 21, vol. 2, pp. 45-49 (1998).

Nakamura, E.S. et al., "Cancer chemopreventive effects of constituents of Caesalpinia ferrea and related compounds," Cancer Lett., vol. 177, pp. 119-24 (2002).

Ohno, T. et al., "Cytotoxic activity of gallic acid against liver metasis of mastocytoma cells P-815," Anticancer Res., vol. 21, pp. 3875-80 (2001).

Ohtani, K. et al., "Minor Diterpene Glycosides from Sweet Leaves of *Rubus suavissimus*," Phytochemistry, vol. 31, No. 5, pp. 1553-1559 (1992).

Ono, Y., "The health beneficial effects of Tien-cha (*Rubus suavissimus* tea) and its applications," Food Style 21, vol. 6, pp. 77-80 (2002).

Panizzi, L. et al., "In Vitro Antimicrobial Activity of Extracts and Isolated Constituents of *Rubus Ulmifolins*," J. Ethnopharmacol., vol. 29, pp. 165-8 (2002).

Polewski, K. et al., "Gallic Acid, a Natural Antioxidant, in Aqueous and Micellar Environment: Spectroscopic Studies," Current Topics in Biophysics, vol. 26, No. 2, pp. 217-227 (2002).

Rosen, L, "Antiangiogenic Strategies and Agents in Clinical Trials," Oncologist, vol. 5, supplement 1, pp. 20-27 (2000).

Rupnick, M.A. et al., "Adipose Tissue Mass Can Be Regulated Through the Vasculature," PNAS, vol. 99, No. 16, pp. 10730-10735 (2002).

Seto, T. et al., "β-Glucosyl Esters of 19α-hydroxyursolic Acid Derivatives in Leaves of *Rubus* species," Phytochemistry, vol. 23, No. 12, pp. 2829-2834 (1984).

Tanaka, T. et al., "Rubusoside (β-D-glucosyl ester of 13-O-62 -D-glucosyl-steviol), a Sweet Principle of *Rubus chingii* Hu (Rosaceae)," Agric. Biol. Chem., vol. 45, No. 9, pp. 2165-2166 (1981).

Wenger, F.A. et al., "Tumor Size and Lymph-node Status in Pancreatic Carcinoma—Is There a Correlation to the Preoperative Immune Function?," Langenbecks Archives of Surgery, vol. 384, pp. 473-478 (1999).

Wolfe, K. et al., "Antioxidant Activity of Apple Peels," J. Agric. Food Chem., vol. 51, pp. 609-614 (2003).

Yang, G.Y. et al., "Effect of Black and Green Tea Polyphenols on C-jun Phosphorylation and $H_2O_2$ Production in Transformed and Non-transformed Human Bronchial Cell Lines: Possible Mechanisms of Cell Growth Inhibition and Apoptosis Induction," Carcinogenesis, vol. 21, No. 11, pp. 2035-2039 (2000).

Zhou, W.-H. et al., "A New Sweet Diterpene-glucoside in Leaves of *Rubus suavissimus*," Acta Botanica Sinica, vol. 34, No. 4, pp. 315-318 (1992).

* cited by examiner

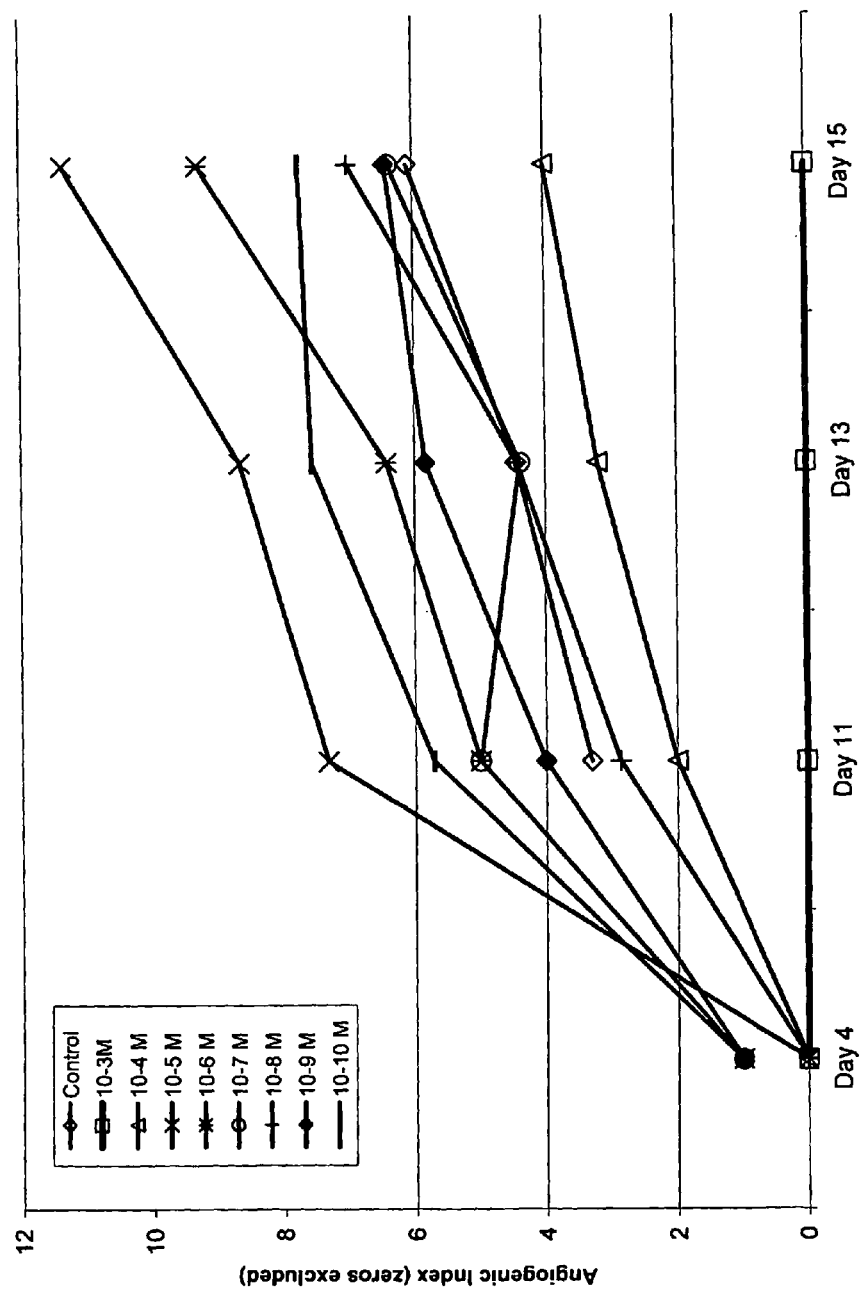

ANGIOGENIC AGENTS FROM PLANT EXTRACTS, GALLIC ACID, AND DERIVATIVES

The development of this invention was subject to a contract between the Board of Supervisors of Louisiana State University and Agricultural and Mechanical College, and the United States Department of Veterans Affairs. The United States Government has certain rights in this invention.

This is the United States national stage of international application PCT/US04/016647, filed 27 May 2004, which claims the benefit of the 28 May 2003 filing date of U.S. provisional application Ser. No. 60/473,806 under 35 U.S.C. §119(e).

The benefit of the May 28, 2003 filing date of provisional application Ser. No. 60/473,806 is claimed under 35 U.S.C. §119(e).

TECHNICAL FIELD

This invention pertains to a method to inhibit angiogenesis by use of extracts of certain *Rubus* plant species and of certain other plants, and by use of gallic acid and its active derivatives.

BACKGROUND ART

Angiogenesis

In an adult, two types of blood vessels can potentially be found. The normal blood vessel is a resting, quiescent, fully developed vessel. A second form, a proliferating or developing blood vessel, occurs rarely during the normal life cycle (only in early development and reproduction, e.g., menstrual cycle and pregnancy). In contrast, the process of angiogenesis, the proliferation and development of new blood vessels, often occurs in wound healing and in pathological processes, e.g., tumor growth. Angiogenesis is a complex process involving many stages, including extracellular matrix remodeling, endothelial cell migration and proliferation, capillary differentiation, and anastomosis. All detectable solid tumors (tumors over 2 mm in diameter) exploit angiogenesis to supply the needed blood to proliferating tumor cells. Studies have demonstrated that the level of vascularization in a tumor is strongly associated with metastasis in melanoma, breast, and lung carcinomas. See R. Bicknell, "Vascular targeting and the inhibition of angiogenesis," Annals of Oncology, vol. 5, pp. 45-50 (1994).

Angiogenesis inhibitors have been suggested to intervene into neoplastic processes. See G. Gasparini, "The rationale and future potential of angiogenesis inhibitors in neoplasia," Drugs, vol. 58, pp. 17-38 (1999). The inhibitory agents block angiogenesis, thereby causing tumor regression in various types of neoplasia. Known therapeutic candidates include naturally occurring angiogenic inhibitors (e.g., angiostatin, endostatin, platelet factor-4), specific inhibitors of endothelial cell growth (e.g., TNP-470, thalidomide, interleukin-12), agents that neutralize angiogenic molecules (e.g., antibodies to fibroblast growth factor or vascular endothelial growth factor), suramin and its analogs, tecogalan, agents that neutralize receptors for angiogenic factors, agents that interfere with vascular basement membrane and extracellular matrix (e.g., metalloprotease inhibitors, angiostatic steroids), and anti-adhesion molecules (e.g., antibodies such as anti-integrin alpha v beta 3). See L. Rosen, "Antiangiogenic strategies and agents in clinical trials," Oncologist, vol. 5, supplement 1, pp. 20-27 (2000).

Abnormal angiogenesis occurs when improper control of angiogenesis causes either excessive or insufficient blood vessel growth. Excessive blood vessel proliferation favors tumor growth and development of distant metastases, blindness, skin disorders such as psoriasis, and rheumatoid arthritis. Diseases or conditions that have been associated with undesired vascularization include, for example, diabetic retinopathy, retinopathy of prematurity, corneal graft rejection, neovascular glaucoma, retrolental fibroplasia, epidemic keratoconjunctivits, Vitamin A deficiency, atopic keratitis, contact lens overwear, superior limbic keratitis, pterygium keratitis sicca, sjogren's syndrome, acne rosacea, phylectenulosis, syphilis, myobacterial infections, lipid degeneration, chemical bursn, bacterial ulcers, fungal ulcers, Herpes simplex infections, Herpes zoster infections, protozoan infections, Kaposi's sarcoma, Mooren's ulcer, Terrien's marginal degeneration, marginal keratolysis, trauma, rheumatoid arthritis, systemic lupus, polyarteritis, Wegener's sarcoidosis, scleritis, Stevens-Johnson disease, radial keratotomy, macular degeneration, sickle cell anemia, sarcoidosis, pseudoxanthoma elasticum, Paget's disease, vein occlusion, carotid obstructive disease, chronic uveitis, chronic vitritis, Lyme's disease, Eales' disease, Behcet's disease, myopia, optic pits, Stargardt's disease, pars planitis, chronic retinal detachment, hyperviscosity syndromes, toxoplasmosis, post-laser complications, abnormal proliferation of fibrovascular or fibrous tissue, hemangiomas, Osler-Weber-Rendu disease, solid tumors, blood borne tumors, acquired immune deficiency syndrome, ocular neovascular disease, age-related macular degeneration, osteoarthritis, diseases caused by chronic inflammation, Crohn's disease, ulceritive colitis, tumors of rhabdomyosarcoma, tumors of retinoblastoma, tumors of Ewing's sarcoma, tumors of neuroblastoma, tumors of osteosarcoma, leukemia, psoriasis, atherosclerosis, pemphigoid, infections causing retinitis or choroiditis, presumed ocular histoplasmosis, Best's disease, proliferative vitreoretinopathy, Bartonellosis, acoustin neuroma, neruofibroma, trachooma, pyogenic granulomas, obesity, corneal neovascularization, malignant tumor growth beyond 2 mm, benign tumors, benign functional endocrine tumors, arterial/venous malformations, primary hyperparathyroidism, secondary hyperparathyroidism, and tertiary hyperparathyroidism. Other angiogenic-related diseases may include, for example, diseases associated with rubeosis (neovascularization of the angle), and diseases caused by abnormal proliferation of fibrovascular or fibrous tissue, including all forms of proliferative vitreoretinopathy. Any disease having a known angiogenic counterpart could potentially be treated with an anti-angiogenic factor, e.g., psoriasis. See D. Creamer et al., "Overexpression of the angiogenic factor platelet-derived endothelial cell growth factor/thymidine phosphorylase in psoriatic epidermis," Br. J. Dermatol., vol. 137, pp. 851-855 (1997).

Angiogenesis is a prominent contributor to solid tumor growth and the formation of distant metastases. Several experimental studies have concluded that primary tumor growth, tumor invasiveness, and metastasis all require neovascularization. The process of tumor growth and metastasis is complex, involving interactions among transformed neoplastic cells, resident tissue cells (e.g., fibroblasts, macrophages, and endothelial cells), and recruited circulating cells (e.g., platelets, neutrophils, monocytes, and lymphocytes). A possible mechanism for the maintenance of tumor growth is an imbalance, or disregulation, of stimulatory and inhibitory growth factors in and around the tumor. Disregulation of multiple systems allows the perpetuation of tumor growth and eventual metastasis. Angiogenesis is one of many systems that is disregulated in tumor growth. In the past it has been difficult to distinguish between disregulation of angiogenesis and disregulation of other systems affecting a developing tumor. Another complicating factor is that aggressive human melanomas mimic vasculogenesis by producing channels of patterned networks of interconnected loops of extracellular matrix, in which red blood cells, but not endothelial cells, are detected. See A. J. Maniotis et al., "Vascular channel formation by human melanoma cells in vivo and in vitro: Vasculogenic mimicry," Am. J. Pathol., vol. 155, pp. 739-52 (1999). These channels may facilitate perfusion of tumors, independent of perfusion from angiogenesis.

A tumor cannot expand beyond approximately 2 mm without a blood supply to provide nutrients and remove cellular wastes. Tumors in which angiogenesis is important include solid tumors, and benign tumors including acoustic neuroma, neurofibroma, trachoma, and pyogenic granulomas. Inhibiting angiogenesis could halt the growth and potentially lead to regression of these tumors. Angiogenic factors have been reported as being associated with several solid tumors, including rhabdomyosarcoma, retinoblastoma, Ewing sarcoma, neuroblastoma, and osteosarcoma.

Angiogenesis has also been associated with some non-solid tumors, including blood-born tumors such as leukemias, various acute or chronic neoplastic diseases of the bone marrow marked by unrestrained proliferation of white blood cells, usually accompanied by anemia, impaired blood clotting, and enlargement of the lymph nodes, liver, and spleen. It is believed that angiogenesis may play a role in the abnormalities in the bone marrow that give rise to leukemias and multiple myelomas.

Anti-angiogenic factors inhibit tumor growth beyond 2 mm by inhibiting the angiogenic response and thus inhibiting blood vessel growth to the tumor. Although angiogenesis in a tumor may begin at an early stage, a tumor requires a blood supply to grow much beyond about 2 mm. Up to 2 mm diameter, tumors can survive by obtaining nutrients and oxygen by simple diffusion. Most anti-angiogenic factors are not cytotoxic, i.e., capable of killing the tumor cells directly. Small tumors of a size about 1 $mm^3$ can be effectively inhibited and destroyed by factors, either endogenous or exogenous, that stimulate the immune system. It is generally accepted that once a tumor has reached a critical size, the immunological system is no longer able to effectively destroy the tumor; i.e., there is a negative correlation between tumor size and immune competence. See A. K. Eerola et al., "Tumour infiltrating lymphocytes in relation to tumour angiogenesis, apoptosis," Lung Cancer, vol. 26, pp. 73-83 (1999); and F. A. Wenger et al., "Tumor size and lymph-node status in pancreatic carcinoma—is there a correlation to the preoperative immune function?," Langenbecks Archives of Surgery, vol. 384, pp. 473-478 (1999). Early adjuvant use of an effective anti-angiogenic agent to preclude development of tumor metastases beyond 1 to 2 $mm^3$ may allow more effective tumor attack and control by the body's immunological mechanisms. In addition, prolonged adjuvant use of a non-toxic angiogenic inhibitor may prevent tumor dissemination by blocking the growth of vessels required for the transport of tumor cells that would form metastatic foci.

Angiogenesis has also been implicated in obesity. Several mice strains, both young and aged animals, used as obesity models treated with anti-angiogenic agents lost weight. See M. A. Rupnick et al., "Adipose tissue mass can be regulated through the vasculature," PNAS, vol. 99, pp. 10730-10735 (2002). This same study also found that adipose tissue mass was reduced by the anti-angiogenic compounds.

New anti-angiogenic factors are needed, in particular, compounds that not only inhibit new angiogenic growth, but also that degrade existing capillary networks. Very few anti-angiogenic factors have been reported to diminish existing capillary networks.

Chinese Blackberry, *Rubus suavissimus* S. lee

*Rubus suavissimus* S. Lee, a perennial shrub, Chinese blackberry, is one of some 62 species in the genus *Rubus* of the Rosaceae family. It is widely distributed in the southwest of China but flourishes in Guangxi Autonomous Region. Leaves of Chinese blackberry have long been used in southern China as a tea due to its sweet taste, thus the Chinese name Tiancha or Sweet Leaf Tea. The sweet taste is due to the presence of dipterpene glucosides in the leaves, one of which is rubusoside, reaching a concentration of over 5% (w/w). See T. Tanaka et al., "Rubusoside (β-D-glucosyl ester of 13-O-β-D-glucosyl-steviol), a sweet principle of *Rubus chingii* Hu (Rosaceae)," Agric. Biol. Chem., vol. 45, pp. 2165-2166 (1981); and T. Seto et al., "β-Glucosyl esters of 19α-hydroxyursolic acid derivatives in leaves of *Rubus* species," Phytochemistry, vol. 23, pp. 2829-2834 (1984). There were other diterpene glucosides found in the leaves, e.g., suavioside A and suaviosides B, $C_1$, $D_2$, F, G, H, I, and J. See S. Hirono et al., "Sweet and bitter diterpene-glucosides from leaves of *Rubus suavissimus*," Chem. Pharm. Bull., vol. 38, pp. 1743-1744 (1990); W.-H. Zhou et al., "A new sweet diterpene-glucoside in leaves of *Rubus suavissimus*, " " Acta Botanica Sinica, vol. 34, pp. 315-318 (1992); and K. Ohtani et al., "Minor diterpene glycosides from sweet leaves of *Rubus suavissimus*," Phytochemistry, vol. 31, pp. 1553-1559 (1992). Further chemical analyses over the leaves of thirty-nine other *Rubus* spp. revealed that the presence of diterpene glycosides is only limited to the leaves of *R. suavissimus* and *R. chingii*, whereas glucosyl 19α-hydroxyuresana-type triterpenes are more common as constituents in the leaves of *Rubus* spp. See F. Gao et al., "19α-hydroxyursane-type triterpene glucosyl esters from the roots of *Rubus suavissimus* S. Lee," Chem. Pharm. Bull., vol. 33, pp. 37-40 (1985)

In southern China, especially in Guangxi Autonomous Region, the leaves of *R. suavissimus* are used not only as tea and a food additive, but also as herbal medicines thought to nourish the kidneys and lower blood pressure. See P.-F. Huang et al., "Comprehensive utilization of *Rubus suavissimus* S. Lee," Guangxi Huagong, vol. 31, pp. 24-25 (2002). The leaf of Chinese blackberry has also been said to help with fever, to relieve stress on the lungs, to reduce the secretion of phlegm, and to relieve coughs. See Y. Ono, "The health beneficial effects of Tien-cha (*Rubus suavissimus* tea) and its applications," Food Style 21, vol. 6, pp. 77-80 (2002). Recent studies indicated an anti-inflammatory and anti-allergy effect. See U. Kotaro, "Antiallergy action of *Rubus suavissimus*," Shokuhin Kogyo, vol. 40, pp. 52-59 (1997); K. Nakahara, "Anti-allergic activity of Tiencha and oolong tea polyphenols," Food Style 21, vol. 2, pp. 45-49 (1998); and K. Nakahara et al., "Anti-allergic composition containing GOD-type ellagitannin as active ingredient," European Patent Application No. 727218 (1996).

Black Raspberry, *Rubus occidentalis*

*Rubus occidentalis* or black raspberry is a perennial shrub native to North America. The berries are juicy and black, with multiple drupes, and ripen from June to July. When picked the berries separate from their fleshy core, forming a hollow shell compared to the stick core on blackberries. Oregon is the major producer of black raspberry, producing 1.9 million pounds of fresh berries in 1996.

The berries are rich in anthocyanins, pectin, fruit acids, and vitamins A, $B_1$ and C. Anthocyanins are widely distributed in plants, and are responsible for the pink, red, purple and blue hues seen in many flowers, fruits and vegetables. They are water-soluble flavonoid derivatives, which can be glycosylated and acylated. Increased interest is seen in anthocyanins due to their activity as antioxidants, which act as scavengers to free radicals thus avoiding oxidative stress to tissues and cells. See J. M. Kong et al., "Analysis and biological activities of anthocyanins," Phytochemistry, vol. 64(5), pp. 923-33 (2003). The antioxidant activities of the anthocyanins may account for some of beneficial effects derived from the consumption of fruits and vegetables high in anthocyanins against cardiovascular and other diseases.

Black raspberry is a common food item, and also used by USDA inspectors as a natural "ink" to stamp commercial meat products. Recently, the antioxidant activity, corresponding to the high anthocyanin and phenolic content, of black raspberry has been reported. See L. Wada L et al., "Antioxidant activity and phenolic content of Oregon caneberries," J. Agric. Food Chem., vol. 50(12), pp. 3495-500 (2002); and S. Y. Wang et al., "Scavenging capacity of berry crops on superoxide radicals, hydrogen peroxide, hydroxyl radicals, and singlet oxygen," J. Agric. Food Chem., vol. 48(11), pp. 5677-84 (2000). A black raspberry extract was found to inhibit tumor development in rodents, possibly by impairing signal transduction pathways leading to activation of activated protein 1 and nuclear factor kappa B and by inhibiting the activity of cyclooxygenase. See C. Huang et al., "Inhibition of benzo (a)pyrene diol-epoxide-induced transactivation of activated Protein 1 and Nuclear Factor B by black raspberry extracts," Cancer Research, vol. 62, pp. 6857-6863 (2002); and N. P. Seeram et al., "Cyclooxygenase inhibitory and antioxidant cyanidin glycosides in cherries and berries," Phytomedicine, vol. 8(5), pp. 362-9 (2001). The active antioxidant compounds in black raspberry are known to be orally bioavailable. See T. K. McGhie et al., "Anthocyanin glycosides from berry fruit are absorbed and excreted unmetabolized by both humans and rats," J. Agric. Food Chem., vol. 51(16), pp. 4539-4548 (2003). However, dietary intervention often fails in clinical studies, probably due to the low levels and huge variations of the unidentified active compounds in the berry diet tested. See B. L. Halvorsen et al., "A systematic screening of total antioxidants in dietary plants," J. Nutr., vol. 132(3), pp. 461-71 (2002).

Earlier studies suggested that a component(s) in black raspberry influenced the metabolism of N-nitrosomethylbenzylamine. See L. A. Kresty et al., "Inhibitory effect of lyophilized black raspberries on esophageal tumorigenesis and $O^6$-methylguanine levels in the F344 rat," Proc. Annu. Meet. Am. Assoc. Cancer Res., vol. 39, p. A120 (1998). This chemopreventive effect has primarily been attributed to the ellagic acid in black raspberries, which has been shown to inhibit cancers induced in rodents by several carcinogens. The chemopreventive activity of ellagic acid and black raspberry fractions was assessed in a Syrian hamster embryo cell transformation model, finding that ellagic acid and a methanol fraction of black raspberry produced a dose-dependent decrease in transformation, possibly through interfering with the uptake, activation, and/or detoxification of the carcinogenic benzo[a]pyrene and/or the intervention of DNA binding and DNA repair. See H. Xue et al., "Inhibition of cellular transformation by berry extracts," Carcinogenesis, vol. 22(2), pp. 351-6 (2001).

Pomegranate Fruit, *Punica granatum* L.

Pomegranate, *Punica granatum* L., is of the family *Punicaceae* and is called the Wonderful cultivar. The fruits are commercially available. A number of studies have reported that pomegranate fruit and its methanol extract possess antioxidant compounds. See M. I. Gil et al., "Antioxidant activity of pomegranate juice and its relationship with phenolic composition and processing," J. Agric. Food Chem., vol. 48(10), pp. 4581-9 (2000); R. P. Singh et al., "Studies on the antioxidant activity of pomegranate (*Punica granatum*) peel and seed extracts using in vitro models," J. Agric. Food Chem., vol. 50(1), pp. 81-6 (2002); and International Application Nos. WO 00/64472 and WO 2004/022028. Anthocyanins and hydrolysable tannins in the form of ellagic acid and derivatives were detected in the juice. Also pomegranate fruit wine demonstrated antioxidant activity and inhibited nuclear factor kappa B. See S. Y. Schubert et al., "A novel mechanism for the inhibition of NF-kappaB activation in vascular endothelial cells by natural antioxidants," FASEB J., vol. 16(14), pp. 1931-3 (2002). An organic extract of pomegranate peel fed to albino Wistar rats inhibited oxidative enzymes such as catalase, peroxidase and superoxide dismutase, but increased lipid peroxidation. See K. N. Chidambara Murthy et al., "Studies on antioxidant activity of pomegranate (*Punica granatum*) peel extract using in vivo models," J. Agric. Food Chem., vol. 50(17), pp. 4791-5 (2002). Histopathological studies of the liver demonstrated a protective effect the methanolic extract of pomegranate peel on hepatic architecture. The antioxidant activity displayed by the pomegranate peel extract may be due to gallotannins and a range of prodelphinidins as well as anthocyanidins. See G. W. Plumb et al., "Antioxidant properties of gallocatechin and prodelphinidins from pomegranate peel," Redox Rep., vol. 7(1), pp. 41-6 (2002); and Y. Noda et al., "Antioxidant activities of pomegranate fruit extract and its anthocyanidins: delphinidin, cyanidin, and pelargonidin," J. Agric. Food Chem., vol. 50(1), pp. 166-71 (2002). Pomegranate polyphenols were found to protect low-density lipoprotein against cell-mediated oxidation via two pathways: direct interaction of the polyphenols with the lipoprotein and/or an indirect effect through accumulation of polyphenols in arterial macrophages. See M. Aviram et al., "Pomegranate juice flavonoids inhibit low-density lipoprotein oxidation and cardiovascular diseases: studies in atherosclerotic mice and in humans," Drugs Exp. Clin. Res., vol. 28(2-3), pp. 49-62 (2002). The antioxidative and antiatherogenic effects of pomegranate polyphenols were demonstrated using an in vitro assay in humans and in atherosclerotic apolipoprotein E deficient mice. See M. Kaplan et al., "Pomegranate juice supplementation to atherosclerotic mice reduces macrophage lipid peroxidation, cellular cholesterol accumulation and development of atherosclerosis," J. Nutr., vol. 131(8), pp. 2082-9 (2001).

Pomegranate seed oil (5%) was tested in a mouse model for its chemopreventive activity against cancer and found that it significantly decreased tumor incidence, decreased the number of tumor sites, and decreased 12-O-tetradecanoylphorbol 13-acetate (TPA)-induced ornithine decarboxylase activity. See J. J. Hora et al., "Chemopreventive effects of pomegranate seed oil on skin tumor development in CD1 mice," J. Med. Food., vol. 6(3), pp. 157-61 (2003); and International Application No. WO 02/094303. Components of pomegranate fruit (fermented juice, aqueous pericarp extract, and cold-pressed or supercritical CO2-extracted seed oil) displayed various degrees of anti-proliferative effects on a human breast cancer cell line and the activity was correlated with polyphenols in these fractions. See N. D. Kim et al., "Chemopreventive and adjuvant therapeutic potential of pomegranate (*Punica granatum*) for human breast cancer," Breast Cancer Res. Treat., vol. 71(3), pp. 203-17 (2002).

Pomegranate extract has also been shown to be anti-inflammatory. Combined with the extract of *Centella asiatica*, pomegranate extract was able to reduce clinical signs of chronic periodontitis. See G. Sastravaha et al., "Adjunctive periodontal treatment with *Centella asiatica* and *Punica granatum* extracts. A preliminary study," J. Int. Acad. Periodontol., vol. 5(4), pp. 106-15 (2003). Pomegranate extract used topically reduced candidiasis associated with denture stomatitis. See L. C. Vasconcelos et al., Use of *Punica granatum* as an antifungal agent against candidosis associated with denture stomatitis," Mycoses, vol. 46(5-6), vol. 192-6 (2003).

Absorption into blood stream of ingested pomegranate ellagitannins in the form of punicalagin is around 3 to 6%, indicating that a large amount of the extract has to be ingested for the active components to be bioavailable. See B. Cerda et al., "Evaluation of the bioavailability and metabolism in the rat of punicalagin, an antioxidant polyphenol from pomegranate juice," Eur. J. Nutr., vol. 42(1), pp. 18-28 (2003).

Using a human umbilical vein endothelial cell (HUVEC) model, pomegranate seed oil and fermented juice polyphenols were demonstrated to be anti-angiogenic, inhibiting proliferation of the endothelial cells, myometrial cells, amniotic fluid fibroblasts, and tubule formation. See M. Toi et al., "Preliminary studies on the anti-angiogenic potential of pomegranate fractions in vitro and in vivo," Angiogenesis, vol. 6, pp. 121-128 (2003); and International Application No. 2004/019961. These preparations also showed downregulation of vascular endothelial growth factor, which is required during the processes of angiogenic initiation and growth. In a test using the chicken chorioallantoic membrane model, pomegranate fermented juice polyphenols were found to inhibit angiogenesis, but the pomegranate pericarp polyphenols were not active. This suggests different inhibitory activities displayed by different sources of the same class of polyphenols. See Toi et al., 2003.

Gallic Acid

Gallic acid or 3,4,5-trihydroxy benzoic acid, is a colorless crystalline organic acid found in many plants. The list of plants that have been shown to contain gallic acid include: *Abrus prccatorius* L.; *Acacia catechu* (L.) Willd.; *Ampelopsis brevipedunculata; Ampelopsis japonica; Coriaria sinica* Maxim.; *Cornus officinalis* Sieb. et Zucc. (Dogwood); *Cotinus coggygria* Scop. (Smokebush); *Daucus carota* L. var. *Sativa* DC.; *Iridium stephanianum* Willd.; *Eucalyptus robusta* Sm.; *Euonymus bungeanus* Maxim. (Winterberry Euonymus); *Euphorbia humifusa* Wild. (Wolf's milk); *Geranium pratense* L.; *Geranium wilfordii* Maxim. (Heron's Bill); *Juglans regia* L.; *Loropetalum chinensis* (R. Br.) *Oliv.* (Chinese fringe tree); *Lythrum salicaria* L.; *Malus* spp. (Apple); *Mangifera indica* L. (Mango); *Macrocarpium officinale* Sieb. et Zucc.; *Passiflora caerulea* L.; *Pharbitis nil* (L.) Choisy; *Phyllanthus emblica* L.; *Pistacia chinensis* Bge.; *Platycarya longipes* Wu.; *Platycarya strobilacea* Sieb. et Zucc. (Australia cheesewood); *Polygonum aviculare* L.; *Polygonum bistortal*. (Bistort); *Psidium guajava* L. (guava); *Quercus infectoria* Oliver; *Rheum officinale* Baill.; *Rheum palmatum* L. (Rhubarb); *Rheum tanguticum* Maxim. Ex Reg.; *Rhus chinensis* Mill. (Chinese sumac gallnut); *Rhus potaninii* Maxim. (Sumac gallnut); *Rosa chinensis* Jacq. (Mini rose); *Rosa rugosa* Thunb. (Rose); *Rubus ulmifolius; Rumex japonicus* Houtt. (Japanese dock); *Sanguisorba officinalis* L. (Burnet); *Sapium sebiferum* (L.) Roxby.; *Syzygium cumini* (L.) Skeels; *Tamarix chinensis* Lour.; *Terminalia chebula* Retz. (Medicine terminalia); *Tetrastigma hypoglaucum* Planch.; and *Tussilago farfara* L. See U.S. Pat. No. 6,444,236; Colored Illustrations of Chinese Traditional and Herbal Ordinary Drugs in China, Wu Jianrong and Quiz Dewey, editors; Huizhou Technology and Science Press, Guiyang, China (1993); Z. Liu et al., *Encyclopedia of Woody Medicinal Plants of China*, CD-ROM, Academic Services Associates, Inc., Seattle, Wash. (2000); D. Liu et al., "Studies on Chemical Constituents from *Tetrastigma Hypoglaucum*," Chinese Trad. And Herbal Drugs, vol. 34, pp. 4-6 (2003); L. Panizzi et al., "In Vitro Antimicrobial Activity of Extracts and Isolated Constituents of *Rubus Ulmifolins*," J. Ethnopharmacol., vol. 29, pp. 165-8 (2002); Encyclopedia of Traditional Chinese Medicine, Shanghai S&T Press (1986); and K. Wolfe et al., "Antioxidant activity of apple peels," J. Agric. Food Chem., vol. 51, pp. 609-14 (2003).

Since gallic acid has hydroxyl groups and a carboxylic acid group in the same molecule, two molecules can react to form an ester, digallic acid. Gallic acid is usually obtained by the hydrolysis of tannic acid with sulfuric acid. Gallic acid is known to be a strong natural antioxidant. See K. Polewski et al., "Gallic acid, a natural antioxidant, in aqueous and micellar environment: spectroscopic studies," Current Topics in Biophysics, vol. 26, pp. 217-227 (2002).

Gallic acid is wide-spread in plant foods and beverages such as tea and wine and has been shown to be one of the anticarcinogenic polyphenols present in green tea. Gallic acid has been shown to display selective cytotoxicity against tumor cells, and to induce apoptosis in tumor cells. See K. Isuzugawa et al., "Different generation of inhibitors against gallic acid-induced apoptosis produces different sensitivity to gallic acid," Biol. Pharm. Bull., vol. 24, pp. 249-253 (2001). Also, theaflavin monogallates and digallates isolated from tea have been shown to inhibit cancer cell growth and induce apoptosis. See, e.g., J. Lu et al., "Differential effects of theaflavin monogallates on cell growth, apoptosis, and Cox-2 gene expression in cancerous versus normal cells," Cancer Research, vol. 60, pp. 6465-6471 (2000); T. Ohno et al., "Cytotoxic activity of gallic acid against liver metasis of mastocytoma cells P-815," Anticancer Res., vol. 21, pp. 3875-80 (2001); and G. Y. Yang et al., "Effect of black and green tea polyphenols on c-jun phosphorylation and $H_2O_2$ production in transformed and non-transformed human bronchial cell lines: possible mechanisms of cell growth inhibition and apoptosis induction," Carcinogenesis, vol. 21, pp. 2035-2039 (2000). The anti-tumor promoting active constituents of the fruits of *Caesalpinia ferrea* were identified as gallic acid and methyl gallate. See E. S. Nakamura et al., "Cancer chemopreventive effects of constituents of *Caesalpinia ferrea* and related compounds," Cancer Lett., vol. 177, pp. 119-24 (2002). Orally administered gallic acid, with and without the anti-cancer drug cisplatin, was found to cause apoptosis in lung cancer cells transplanted in mice. See M. Kawada, "Anti-tumor effect of gallic acid on LL-2 lung cancer cells transplanted in mice," Anticancer Drugs, vol. 12, pp. 847-852 (2001).

Gallotannic acid, gallic acid, and catechin were found to cause food intake and growth depression when fed to weanling rats. See M. A. Joslyn et al., "Comparative effects of gallotannic acid and related phenolics on the growth of rats," J. Nutrition, vol. 98, pp. 119-126 (1969). The tolerance of the rats to tannic acid depended on their initial age and weight. Older and heavier rats adjusted to tannic acid in the diet. See Z. Glick et al., "Food intake depression and other metabolic effects of tannic acid in the rat," J. Nutrition, vol. 100, pp. 509-515 (1970). Gallic acid was found to induce a fatty liver. Tannic acid, but not gallic acid, increased excretion of nitrogen. See Z. Glick et al., "Effect of tannic acid and related compounds on the absorption and utilization of proteins in the rat," J. Nutrition, vol. 100, pp. 516-520 (1970). Gallic acid and propyl gallate were found to suppress food intake and retard growth, with propyl gallate having a much greater effect. See Z. Glick, "Modes of action of gallic acid in suppressing food intake in rats," J. Nutrition, vol. 111, pp. 1910-

1916 (1981). In a study on mice assessing the toxicity of gallic acid, gallic acid did not affect weight of the mice at 1000 mg/kg for 28 days, but a slight decrease in food intake was noted. See K. Rajalakshmi et al., "Assessment of the no-observed-adverse-effect level (NOAEL) of gallic acid in mice," Food and Chemical Toxicology, vol. 39, pp. 919-922 (2001). However, in a subchronic toxicity study on rats, 5% gallic acid was found to suppress body weight gain over a period of 13 wks. See N. Niho et al., "Subchronic toxicity study of gallic acid by oral administration in F344 rats," Food and Chemical Toxicology, vol. 39, pp. 1063-1070 (2001).

U.S. Patent Application No. 2002/0068094 discloses a physiologically active extract from indigo which includes tryptanthrin, 3,5,4'-rihydroxy-6,7-m-ethylenedioxy-flavone, kaempferol, 3,5,7,4'-tetrahydroxy-6-methoxy-flavone, gallic acid, caffeic acid, indirubin, pheophorbide a, and methyl pheophorbide a. Although indicating that the extract may have many different physiological functions, experiments are discussed only to show antiseptic action, antiviral action, antitumor action, radical-entrapping action, apoptosis controlling action, and action for controlling the production of cytokine. Gallic acid was shown to have radical-entrapping action.

DISCLOSURE OF INVENTION

We have discovered that an extract of Chinese blackberry (*Rubus suavissimus*) inhibited angiogenesis. From the extract, a least two fractions were isolated that showed powerful anti-angiogenic activity. From one of these fractions, gallic acid was shown to be the active compound. The anti-angiogenic activity was measured by an assay that is an in vitro human angiogenesis model using a human placental vein disc. Aqueous extracts from other plants either known or found to have gallic acid (rhubarb root, persimmon fruit, blackberry (*Rubus fruticosus*) leaf and berry, dogwood berry, black raspberry, and pomegranate fruit) were also found to have anti-angiogenic activity. Various derivatives of gallic acid (gallotannin (tannic acid), methyl gallate, propyl gallate, butyl gallate, and octyl gallate) were also found to inhibit angiogenesis. Other derivatives of gallic acid are believed to be anti-angiogenic, including ethyl gallate, lauryl gallate, ellagic acid, BUSMUTH-gallate, galloyl glucose, di-galloyl glucose, tri-galloyl glucose, tetra-galloyl glucose, penta-galloyl glucose, and glyceryl trigallate. The extract from Chinese blackberry also slowed the growth of a pancreatic tumor and of corneal neovascularization in rats. Gallic acid and a refined pomegranate extract were shown to inhibit angiogenesis in fat tissue. Extracts from *Rubus* spp, pomegranate, other plants with gallic acid, and gallic acid and its derivatives will be useful for treating various diseases associated with neovascularization, including diabetic retinopathy, psoriasis, tumors, obesity, cancer, rheumatoid arthritis, etc.

BRIEF DESCRIPTION OF THE DRAWINGS

FIG. 6c illustrates the effect of several concentrations of gallic acid on angiogenesis in human placental vein discs as measured by an angiogenic index after removing discs with a zero angiogenic index (i.e., discs that never initiated an angiogenic response).

FIG. 15b illustrates the effect of the effect of various concentrations (0.1%, 0.075%, 0.05%, 0.025%, 0.01%) of black raspberry berry refined fraction RUO-95 on angiogenesis (both initiation and proliferation) in human placental vein discs as measured by an angiogenic index (Including the Zero Wells and Excluding the Zero Wells).

MODES FOR CARRYING OUT THE INVENTION

EXAMPLE 1

Materials and Methods for Angiogenesis Assay

Figure 1:
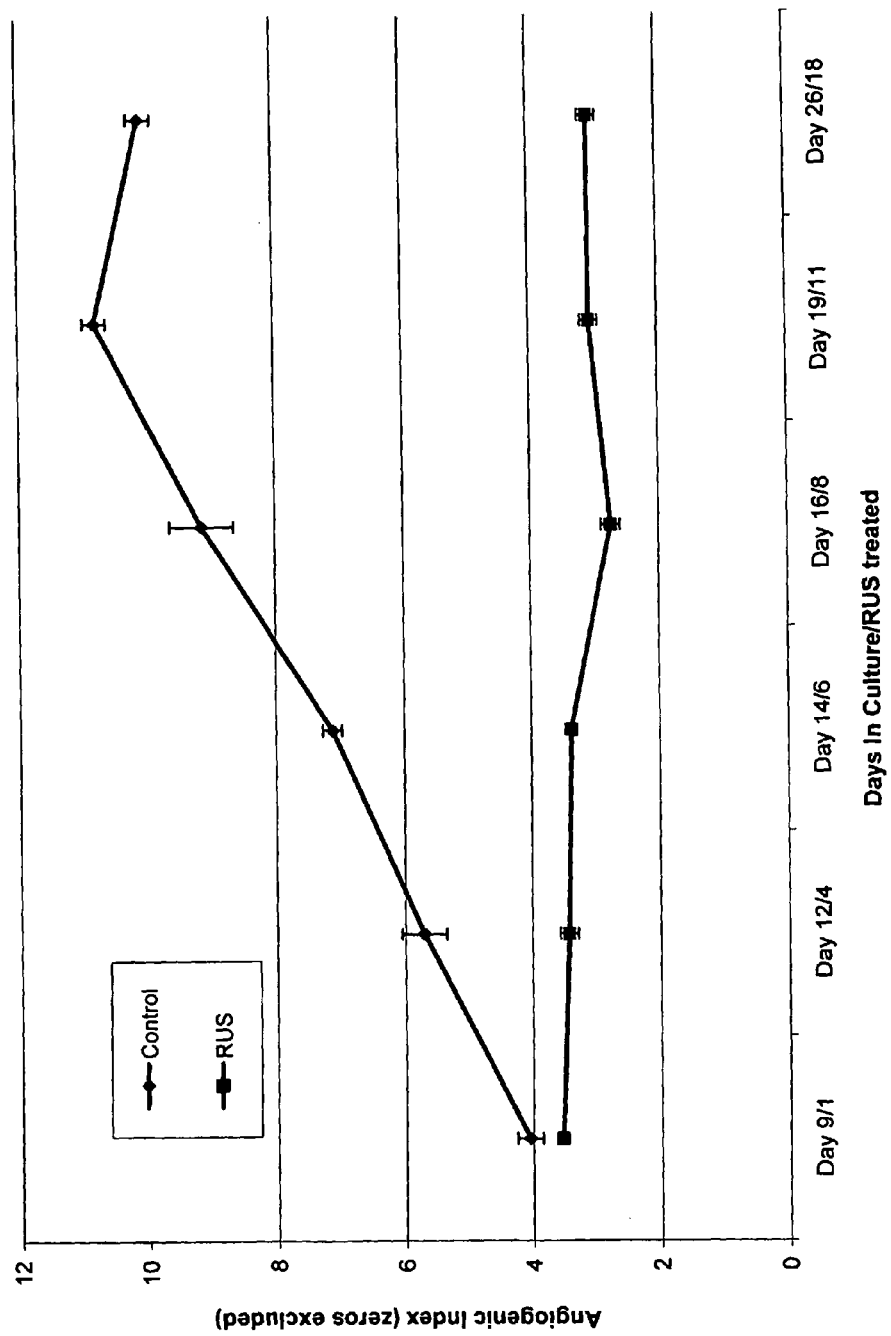
FIG. 1 illustrates the effect of 0.1% Chinese blackberry leaf extract (RUS) on angiogenesis in human placental vein discs as measured by an angiogenic index after removing discs with a zero angiogenic index (i.e., discs that never initiated an angiogenic response).

The Human Placental Vein Angiogenesis Model: Discarded human placentas were obtained anonymously with prior approval of an Institutional Review Board. The placental veins were dissected free from the placenta and adventitial tissue. The trimmed vein segment was opened longitudinally to produce a flat film of venous tissue of full thickness. Vein discs (2 mm diameter) were created with a sterile skin punch (Miltex Instrument Company, Inc.; Lake Success, N.Y.). The discs were placed into wells of a standard 96-well plate (Corning Inc., Corning, N.Y.). The vein disc harvest was completed within three hours of delivery to optimize endothelial cell viability. Vein discs from a single placenta were distributed equally among all treatment groups to ensure randomization. Each well was preloaded with a human thrombin solution (0.05 IU in 2.0 µl), and allowed to evaporate to dryness before use. All chemicals were purchased from Sigma Chemical Company (St. Louis, Mo.) unless otherwise indicated.

Following the placement of the 2 mm vein disc in the bottom of each thrombin-containing well, the disc was covered with 100 µl of a clot-forming medium, comprising 3 mg/ml fibrinogen and 0.5% Σ-amino caproic acid dissolved in Human Placental Vein Angiogenesis Media (HPVAM). HPVAM is made of Medium 199 (Vitrogen Corporation, Carlsbad, Calif.), an antibiotic/antimycotic solution (100 U/ml penicillin, 100 U/ml streptomycin sulfate, and 0.25 µg/ml amphotericinβ; Vitrogen Corporation), and endothelial growth medium (25%) (Vitrogen Corporation). The mixture was allowed to clot by incubating in 5% $CO_2$, 95% air at 37° C. in a humidified incubator. After the medium-containing placental discs had clotted, the vein-containing clot was supplemented with 100 µl HPVAM containing 20% fetal bovine serum (Vitrogen Corporation). The total well volume was 200 µl.

Evaluation of Angiogenesis: Visual evaluation of all wells was performed at 20× or 40× magnification with a standardized reference grid by an unbiased observer using an inverted microscope. Every other day, discs were graded using two criteria: the initiation of sprouting vessels (initiation) and the degree of sprouting (angiogenic index). Initiation of an angiogenic response was defined as the development of three or more vessel sprouts around the periphery of the vein disc. Initiation occurred in 50-95% of the wells, usually 4 to 6 days after establishment of the clots. Initiation was expressed as the percent of the total wells plated that indicated an angiogenic response.

The angiogenic index (AI) was defined using a subjective visual rating system. Each disc was visually rated for the development of vessel sprouting in each of four quadrants. Each of the four quadrants for each disc was rated on a 0-4 scale, depending on the number of sprouts (density) and the length of sprouts. Scores for all four quadrants were summed to express the AI, a numerical rating that could range from 0 to 16. A score of zero indicated no vessel growth in any of the four quadrants, while a score of 16 indicated long, dense angiogenic vessel growth in all four quadrants. For most experiments, the AI was expressed as a mean plus/minus a standard error of the mean.

To separate the process of initiation from that of proliferation, the AI was analyzed both with zero AI data points and without zero AI data points. A zero AI indicated that no angiogenic initiation occurred in that disc. This lack of initiation could have been due either to the effect of the experimental compound, to the insensitivity of the vein disc to stimulation in the culture conditions, or to the vein disc not being viable. In previous experiments, we have shown that only a small percent, about 2 to 3%, of vein discs are not viable (data not shown). Thus, a graph of AI with zero AI data points indicates the complete angiogenic response of initiation and growth under the experimental conditions. However, a graph of AI without the zero AI data points indicates only growth of the vessels after initiation.

To assay for the effect of gallic acid or plant extracts on angiogenesis, the solution to be tested was added in various percentages to HPVAM to yield the tests groups. The control medium was HPVAM supplemented with a matching concentration of NaCl to ensure that the observed effects were not due to a difference in concentration of the medium ingredients. Every two days the medium in each well was replaced, and each well was scored for both initiation of angiogenesis and angiogenic index.

EXAMPLE 2

*Rubus suavissimus* Extractions Assay

RUS Extract: The leaves of *Rubus suavissimus*, Chinese blackberry, were collected from Guangxi, People's Republic of China. The leaves were air-dried and stored at room temperature before extraction. One hundred grams of dried leaves were soaked in 2 L tap water for 1 hr and then brought to a boil two times for 30 min each. The mixture was then filtered with cheesecloth and spray dried to obtain 31 g crude extract powder, the "RUS" extract.

Treatments and Fractionation of the RUS Extract

RUS-A Extract: The crude extract RUS was re-constituted with deionized water and subjected to five consecutive freeze-thaw cycles to yield "RUS-A" extract.

RUS-B Extract: Crude extract RUS was re-constituted with deionized water and boiled for 20 min to yield "RUS-B" extract.

RUS-C and RUS-D Extracts: Crude extract RUS was re-constituted with deionized water, and mixed with 20% trichloroacetic acid (TCA) at a 1:1 v/v ratio and 0.1 ml 10% bovine serum albumin. This mixture was incubated at 4° C. for 30 min and centrifuged at 300× for 30 min. The pH was adjusted to 7 with NaOH, and the mixture re-centrifuged. The precipitate and supernatant were separated to become RUS-C and RUS-D extracts, respectively.

RUS-E and F Extracts: Crude extract RUS was re-constituted with deionized water, and the mixture extracted with 0.8 volume of chloroform three times. The aqueous phase was collected and freeze-dried to yield RUS-F fraction powder. The chloroform phase was collected and further processed. The chloroform was removed by sequentially adding 200 ml methanol to facilitate the evaporation, 500 ml deionized water to remove methanol, and then another 200 ml deionized water to remove any residual organic solvents from the liquid extract. The aqueous liquid extract was then freeze-dried to powder, the "RUS-E" extract.

Further Fractions of RUS-F: The RUS-F fraction was fractionated using column chromatography. The RUS-F powder was dissolved in 50% methanol and then loaded on a 30 g Sephadex LH-20 column. After loading the sample, 50% methanol was used to elute the column. Each 10 ml eluate was collected during the first 100 ml of eluate for 10 fractions (Eluate 1 through 10), and then the second 100 ml eluate was collected as a whole (Eluate 11). Chemical fingerprints of each eluate were obtained using a high performance liquid chromatography system (Beckman Instruments, Fullerton, Calif.). A C18 column (15 cm long, 4.6 mm internal diameter) was used. The mobile phase was set at 1% methanol in water and a flow rate of 1 ml per minute. UV absorption was measured at 254 nm wavelength. Eluate fractions 4 through 10 indicated similar chemical fingerprints, and were combined. The other eluates were kept separate. The resulting eluate fractions were removed of organic solvents, and freeze-dried to yield powder fractions named "RUS-F01" (eluate fraction 1), "RUS-F02" (eluate fraction 2), "RUS-F03" (eluate fraction 3), "RUS-F04" (eluate fractions 4 through 10), and "RUS-F11" (eluate fraction 11).

EXAMPLE 3

Gallic Acid Extraction and Source

Source of Gallic Acid: Gallic acid was isolated and purified as described below from aqueous Chinese blackberry extract prepared from air-dried leaves purchased from Guangxi Botanical Garden, Nanning and Guangxi Normal University S&T New Tech Company, Guilin, China. Gallic acid, methyl gallate, ethyl gallate, propyl gallate, butyl gallate, lauryl gallate, octyl gallate, ellagic acid, BUSMUTH-gallate were purchased from Sigma Chemical Company (St. Louis, Mo.).

Extraction of Gallic Acid from Chinese Blackberry

Fraction RUS-F11 as isolated in Example 2 was further purified by dissolving in 50% methanol and again loading on a Sephadex LH-20 column. This purification step was done twice and yielded a pure compound, initially labeled "RUSF260." RUSF260 was shown to be gallic acid by several methods. The chemical structure of RUSF260 was elucidated in CD3OD carrier solvent on a Bruker DPX400 MHz Nuclear Magnetic Resonance Spectrometer using both $^1$HNMR and $^{13}$CNMR and comparing the spectra with standards. RUSF260 was determined to be gallic acid (data not shown). In addition, mass spectrometry confirmed that the molecular weight of RUSF260 (170.2) matched that of gallic acid. (data not shown)

EXAMPLE 4

Extraction of Other Plant Sources

Rhubarb root (Anguo Herbal Product Market, Hebei, China; grown in Gansu, China), persimmon calyx (Southside Produce, Baton Rouge, La.), and dogwood berry (Anguo Herbal Product Market, Hebei, China; grown in Henan, China) were separately ground to particles of 6 mm or smaller dimensions. For each plant, ten grams of ground particles were added to a 1 L flask with 200 ml ddH$_2$O and allowed to soak overnight at room temperature (20 to 25° C.). The mixture was then boiled for 30 min. After cooling, the supernatant was collected and filtered through a 20 µM filter paper. The filtrate was then concentrated in a rotary evaporator, and then freeze-dried to a powder. This extraction procedure produced the following amounts of crude extracts: rhubarb, 1.98 g; persimmon, 1.27 g; and dogwood, 2.27 g.

EXAMPLE 5

Inhibitory Effects of a Chinese Blackberry Extract (RUS) on Angiogenesis

To test the effectiveness of Chinese blackberry extract on pre-existing angiogenesis, human placental vein discs (PVD) were obtained as above and grown for 9 days in HPVAM with the medium changed every two days. Two groups each with 9 PVDs were used for the control and for the Chinese blackberry extract. At day 9, 0.1% Chinese blackberry extract (extract RUS as named in Example 2) was added to the HPVAM when all PVDs had initiated angiogenesis. Every two to three days after the addition of the Chinese blackberry extract, the PVD were scored and the medium was changed as discussed in Example 1.

The number of wells with angiogenic vessels decreased upon addition of 0.1% Chinese blackberry extract. FIG. 1 shows the angiogenic index without the zero points which indicates the growth of angiogenic vessels after initiation as described in Example 1. Each data point represents an average of 7 observations. The x-axis in FIG. 1 represents the number of days of culture/the number of days since addition of Chinese blackberry extract. The Chinese blackberry-treated PVD stopped angiogenesis whereas untreated PVD continued to develop angiogenesis at a steady rate until day 19.

Figure 2A:
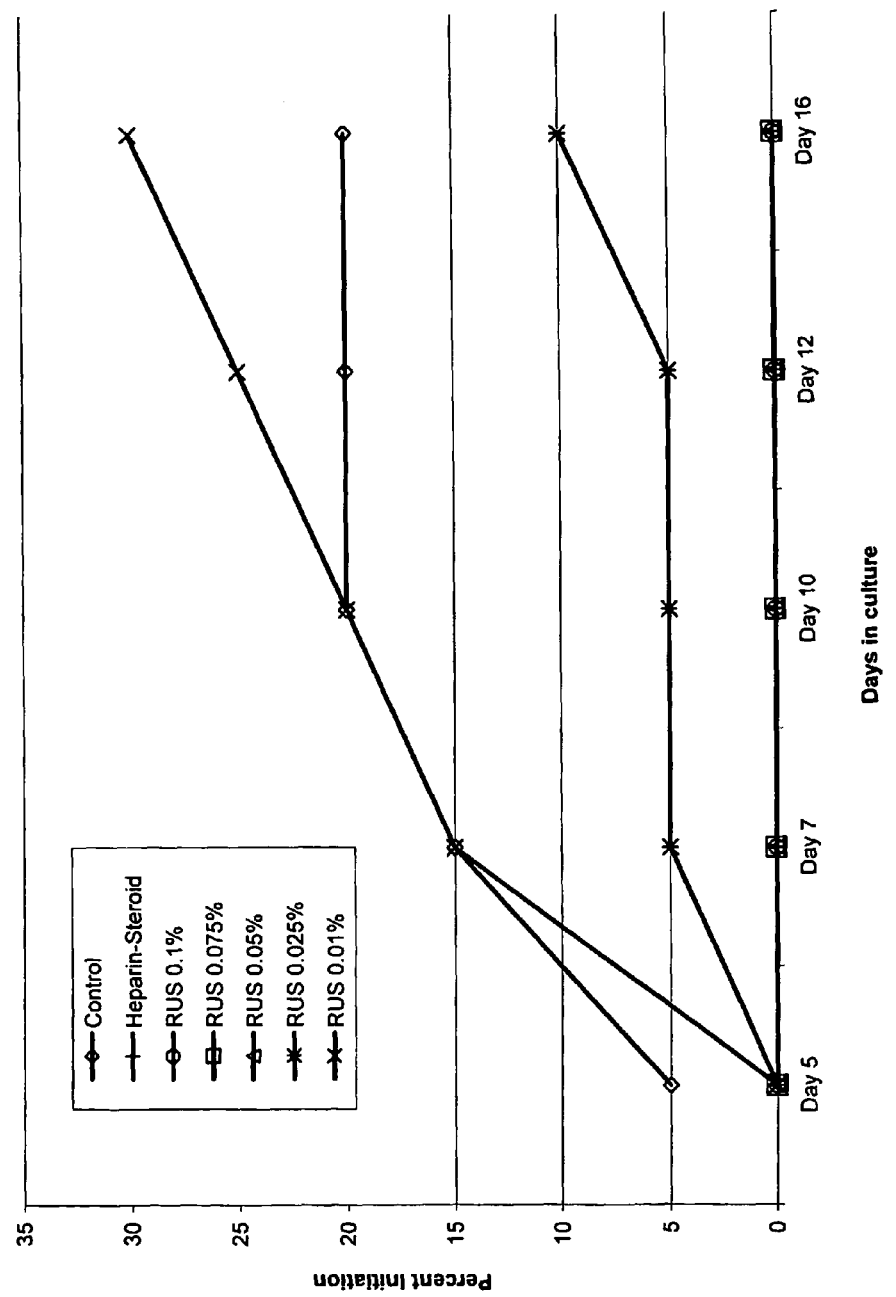
FIG. 2a illustrates the effect of Chinese blackberry leaf extract (RUS) at various concentrations on the initiation of angiogenesis in human placental vein discs.
Figure 2B:
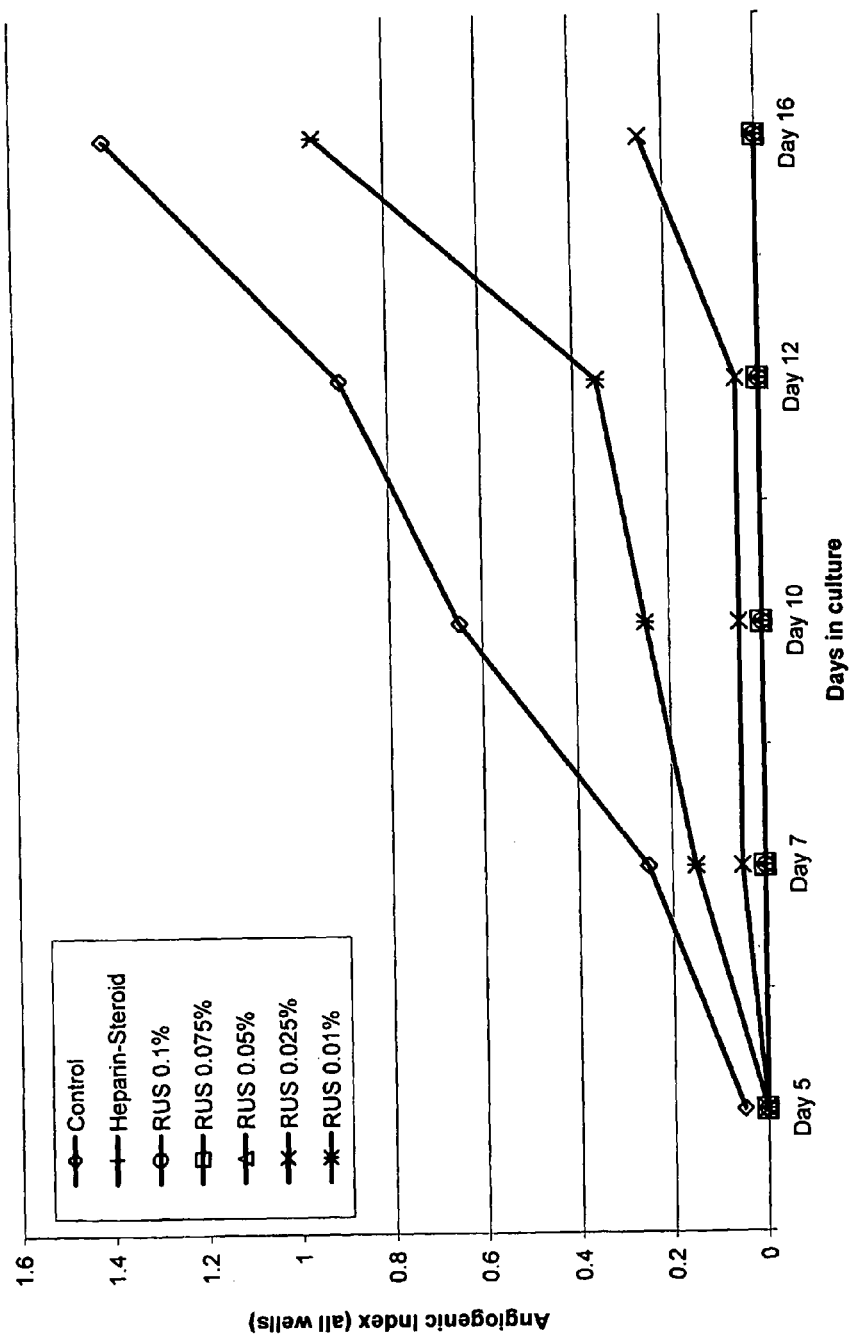
FIG. 2b illustrates the effect of Chinese blackberry leaf extract (RUS) at various concentrations on angiogenesis (both initiation and proliferation) in human placental vein discs as measured by an angiogenic index.
Figure 2C:
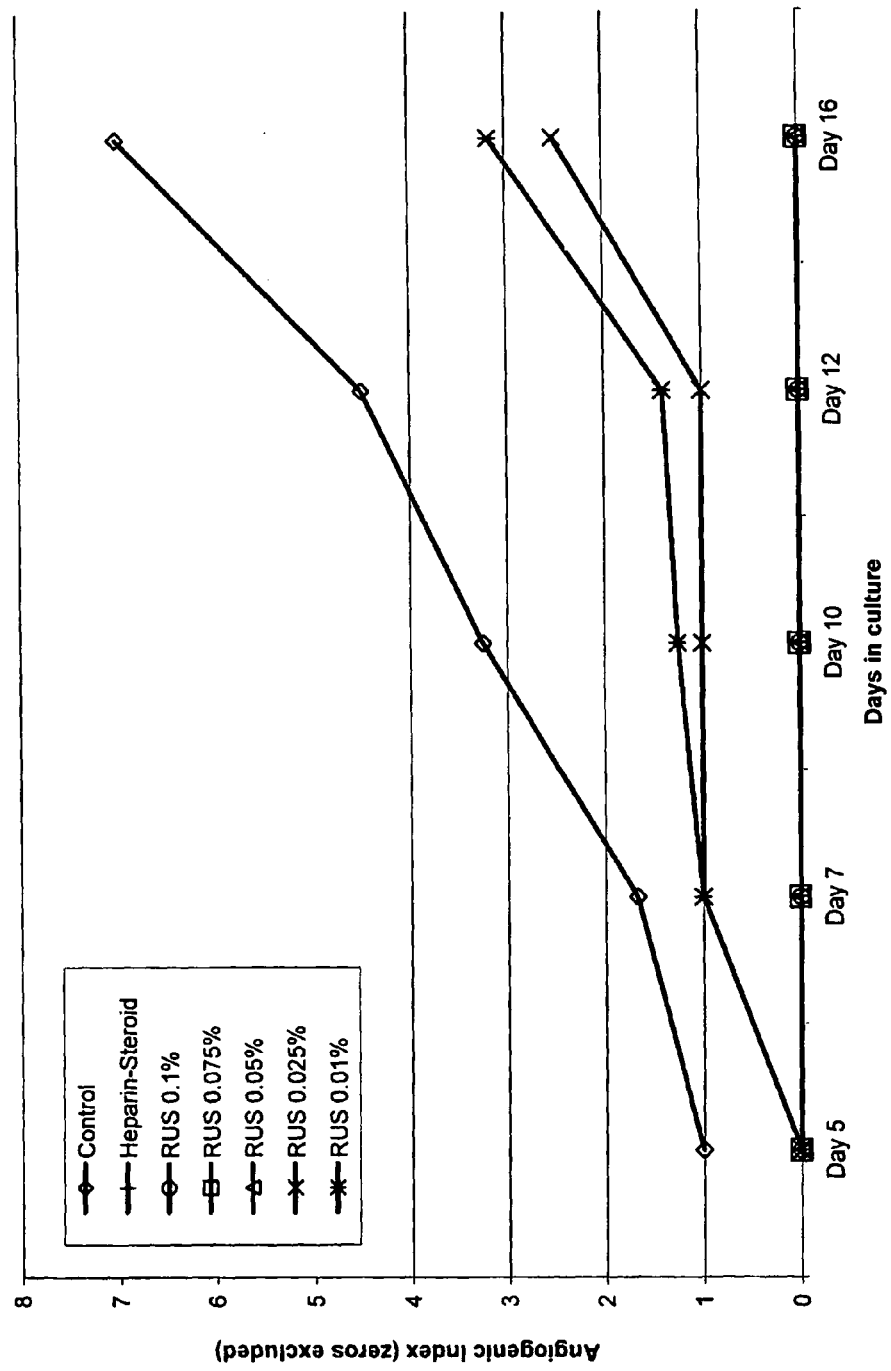
FIG. 2c illustrates the effect of Chinese blackberry leaf extract (RUS) at various concentrations on angiogenesis in human placental vein discs as measured by an angiogenic index after removing discs with a zero angiogenic index (i.e., discs that never initiated an angiogenic response).

To test the effects of the RUS extract at various concentrations on angiogenesis, PVDs were grown in HPVAM supplemented with the RUS extract re-constituted with HPVAM to the following concentrations: 0.1%, 0.075%, 0.05%, 0.025%, and 0.01% (w/v). The control group was supplemented with similar concentrations of NaCl. For each group, 20 PVDs were used. The PVDs were allowed to grow for six days in only HPVAM before adding either NaCl or the RUS extract. Then every two to three days the medium in each well was replaced, and each well scored for both initiation of angiogenesis and the angiogenic index. As shown in FIG. 2a, the initiation of angiogenesis was totally inhibited by 0.05% or higher RUS concentrations, partially inhibited by 0.025%, but was not affected by 0.01%. Similar results were seen in the angiogenic index both with and without the zero data points. (FIGS. 2b and 2c) However, 0.01% RUS showed some inhibitory action in the angiogenic index, indicating some anti-proliferation activity.

These results indicate that the Chinese blackberry extract contains effective and potent anti-angiogenic compounds.

EXAMPLE 6

Inhibitory Effects After Various Treatments of RUS Extract on Angiogenesis

Treatments and Initial Fractions of RUS

To identify the active anti-angiogenic compounds present in the RUS extract, the extract was subjected to various treatments and several fractions collected as described in Example 2. PVDs were grown in HPVAM supplemented with either RUS, RUS-A, RUS-B, RUS-C, RUS-D, RUS-E or RUS-F. All extracts were reconstituted to a concentration of 0.1% (w/v) in HPVAM. Two control groups were used: one group with NaCl as a supplement, and a second group with a heparin-steroid combination for a positive control. The positive control group was treated with a heparin-steroid (21-phosphate hydrocortisone) mixture (300 μg/ml and 350 μg/ml, respectively), which was previously found to reduce angiogenesis by 30 to 40%. Twenty PVDs for each group was used. The PVDs were grown for six days in only HPVAM before adding any extract or control supplement. After addition of the supplements, every two to three days, the medium was replaced in each well, and each well was scored for both initiation of angiogenesis and angiogenic index.

Figure 3A:
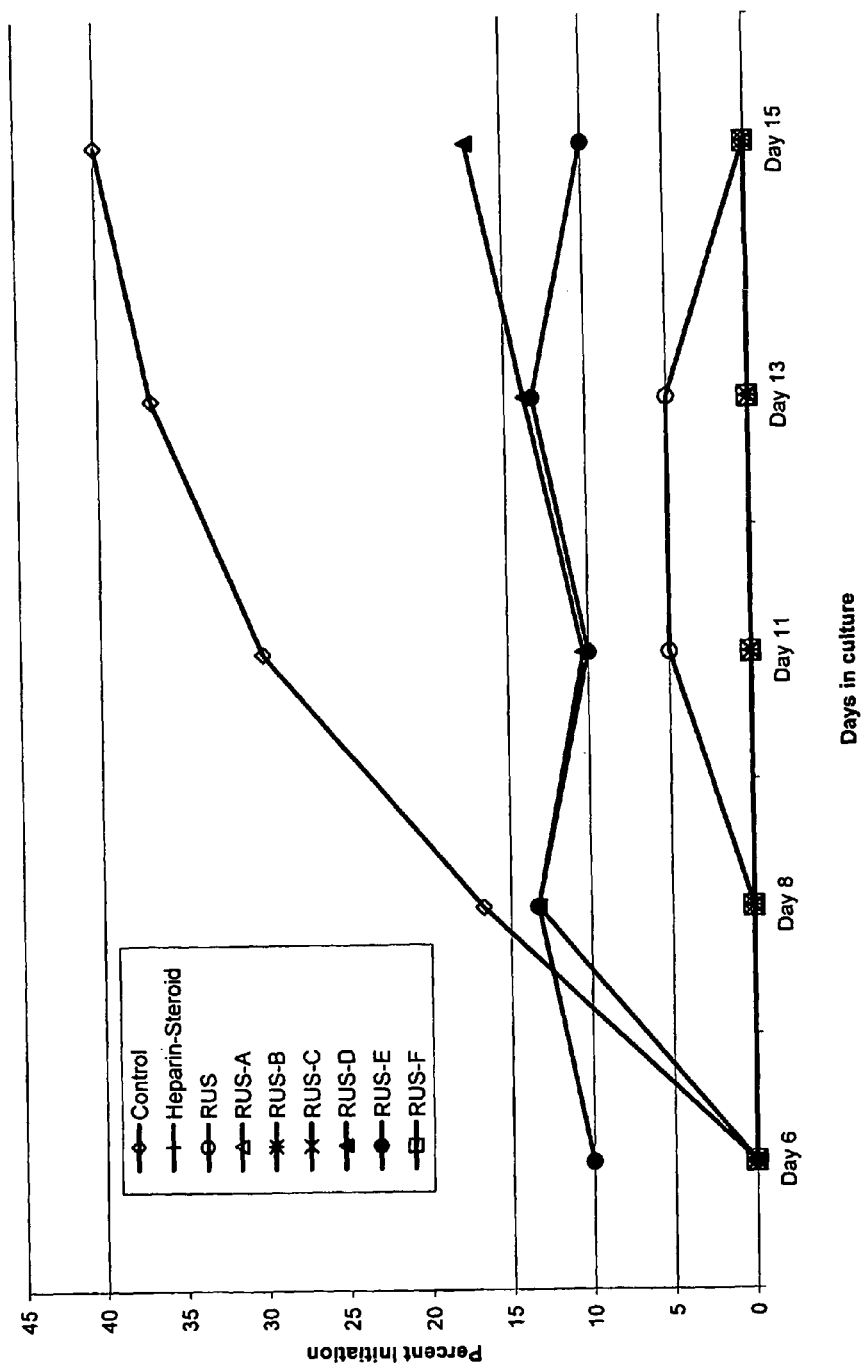
FIG. 3a illustrates the effect of Chinese blackberry leaf extract (RUS) after subjected to various treatments and reconstituted to 0.1% (w/v) on the initiation of angiogenesis in human placental vein discs.
Figure 3B:
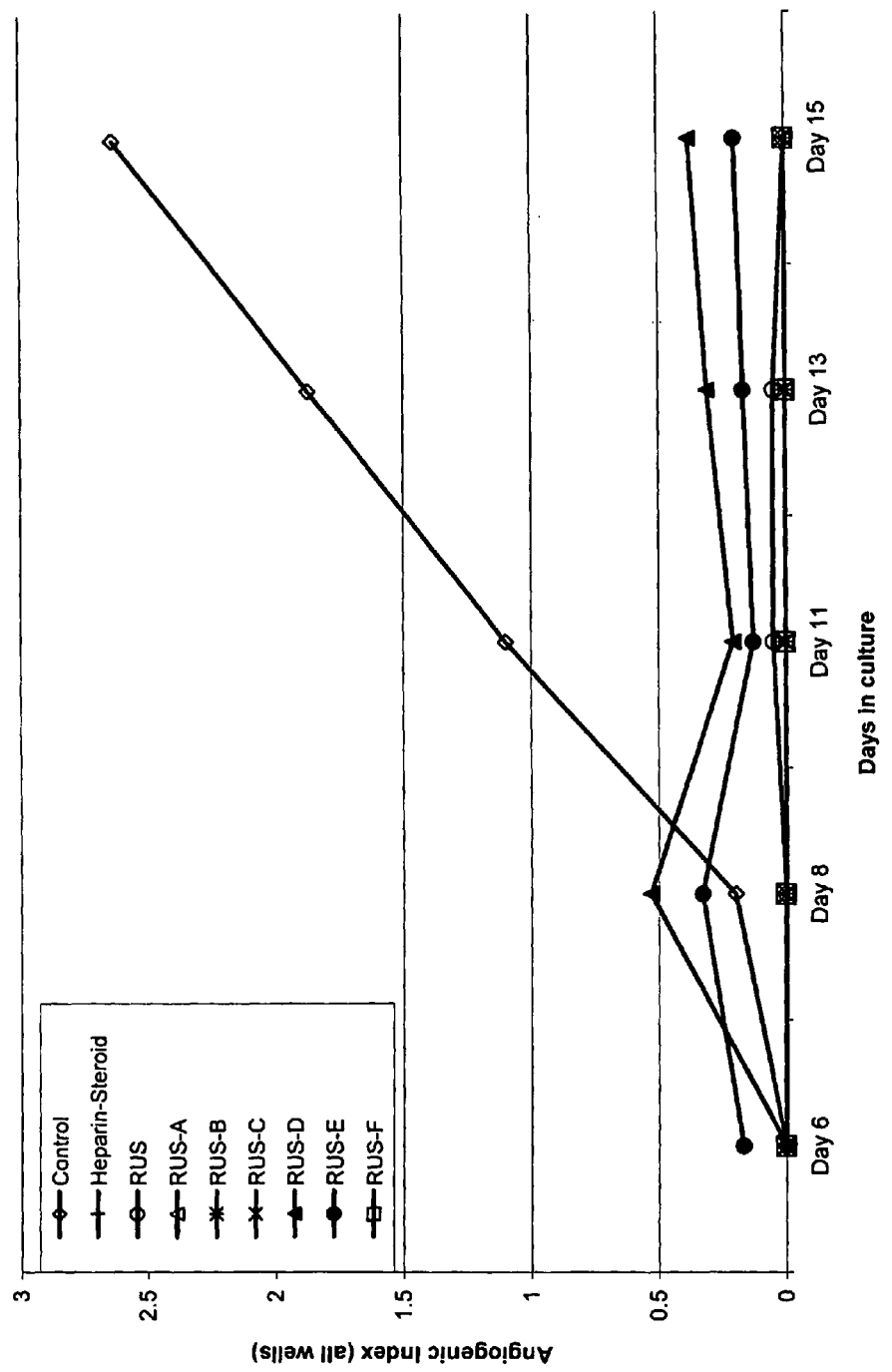
FIG. 3b illustrates the effect of Chinese blackberry leaf extract (RUS) after subjected to various treatments and reconstituted to 0.1% (w/v) on angiogenesis (both initiation and proliferation) in human placental vein discs as measured by an angiogenic index.
Figure 3C:
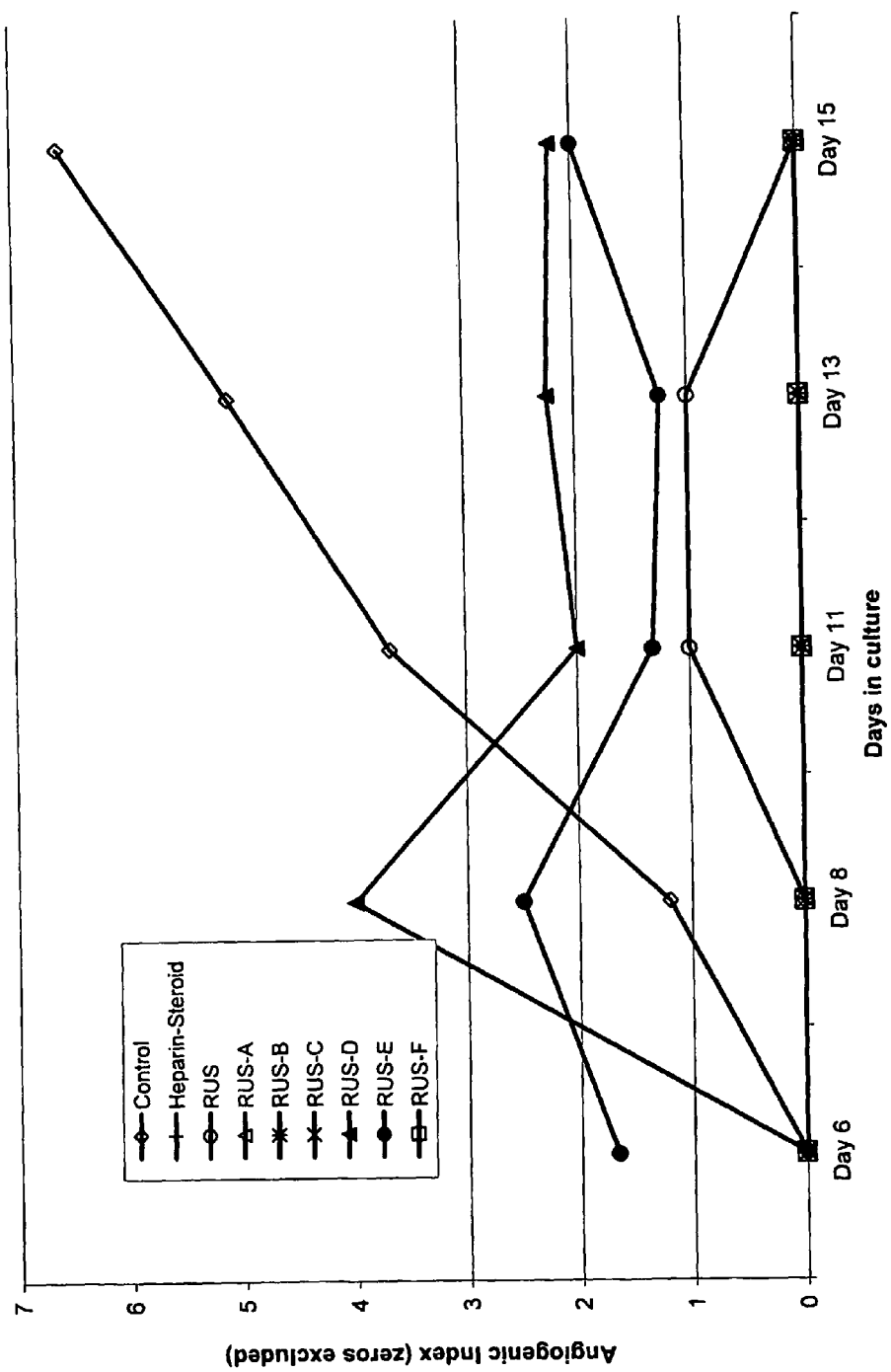
FIG. 3c illustrates the effect of Chinese blackberry leaf extract (RUS) after subjected to various treatments and reconstituted to 0.1% (w/v) on angiogenesis in human placental vein discs as measured by an angiogenic index after removing discs with a zero angiogenic index (i.e., discs that never initiated an angiogenic response).

As shown in FIG. 3a, the initiation of angiogenesis was totally inhibited by the RUS-C and RUS-F fractions and only partially inhibited by RUS-D and RUS-E fractions. RUS-A and RUS-B, the boiling and freeze-thaw treatments of RUS, were still inhibitory, indicating that neither boiling or freezing destroyed the anti-angiogenic activity of the RUS extract. RUS-C contained large molecules such as proteins, complex carbohydrates etc., indicating the likely active compounds could be macromolecules rather than small molecules. Conversely (or complementarily), RUS-D contained smaller molecules such as phenolic acids. RUS-D's partial inhibitory activity may indicate the presence of active compounds but in a reduced concentration due to the formation of salts after the addition of TCA as described in Example 2. RUS-E's low inhibitory activity indicates that potent inhibitors are likely to be polar compounds. The strong inhibitory activity by RUS-F indicates that potent inhibitors are likely to be polar compounds. Similar results were seen in the angiogenic index results, both with and without the zero data points. FIGS. 3b and 3c.

These results indicated that fractions RUS-C and RUS-F retained potent anti-angiogenic activity. The active angiogenic inhibitors should be present in these two fractions in significant amounts that could exert a total inhibition.

Subfractions of RUS-F

The RUS-F extract was further fractionated as described in Example 2 to further isolate the compounds with anti-angiogenic activity. These extracts were then used in the human placental vein disc assay described in Example 1. PVDs were grown in HPVAM for six days. Then the HPVAM medium was supplemented with 0.1% (w/v) of one of the five fractions: RUS-F01, RUS-F02, RUS-F03, RUS-F04, and RUS-F11. The control medium was supplemented with NaCl. Twenty PVDs were used for each group. After addition of the various extracts, every two or three days, the medium in each well was replaced, and each well was scored for both initiation of angiogenesis and angiogenic index.

Figure 4A:
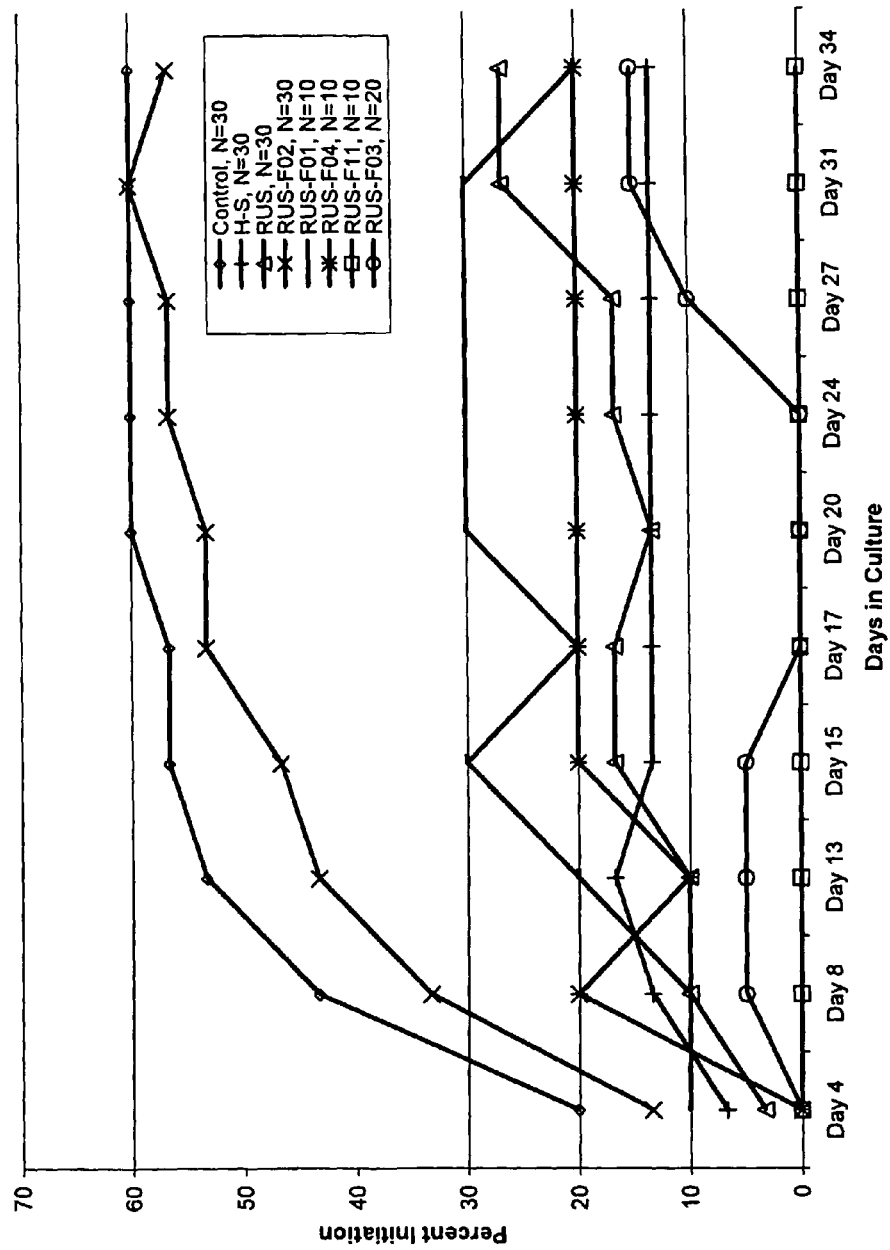
FIG. 4a illustrates the effects of several fractions from one of the Chinese blackberry leaf extracts (RUS-F) at a 0.1% concentration on the initiation of angiogenesis in human placental vein discs.
Figure 4B:
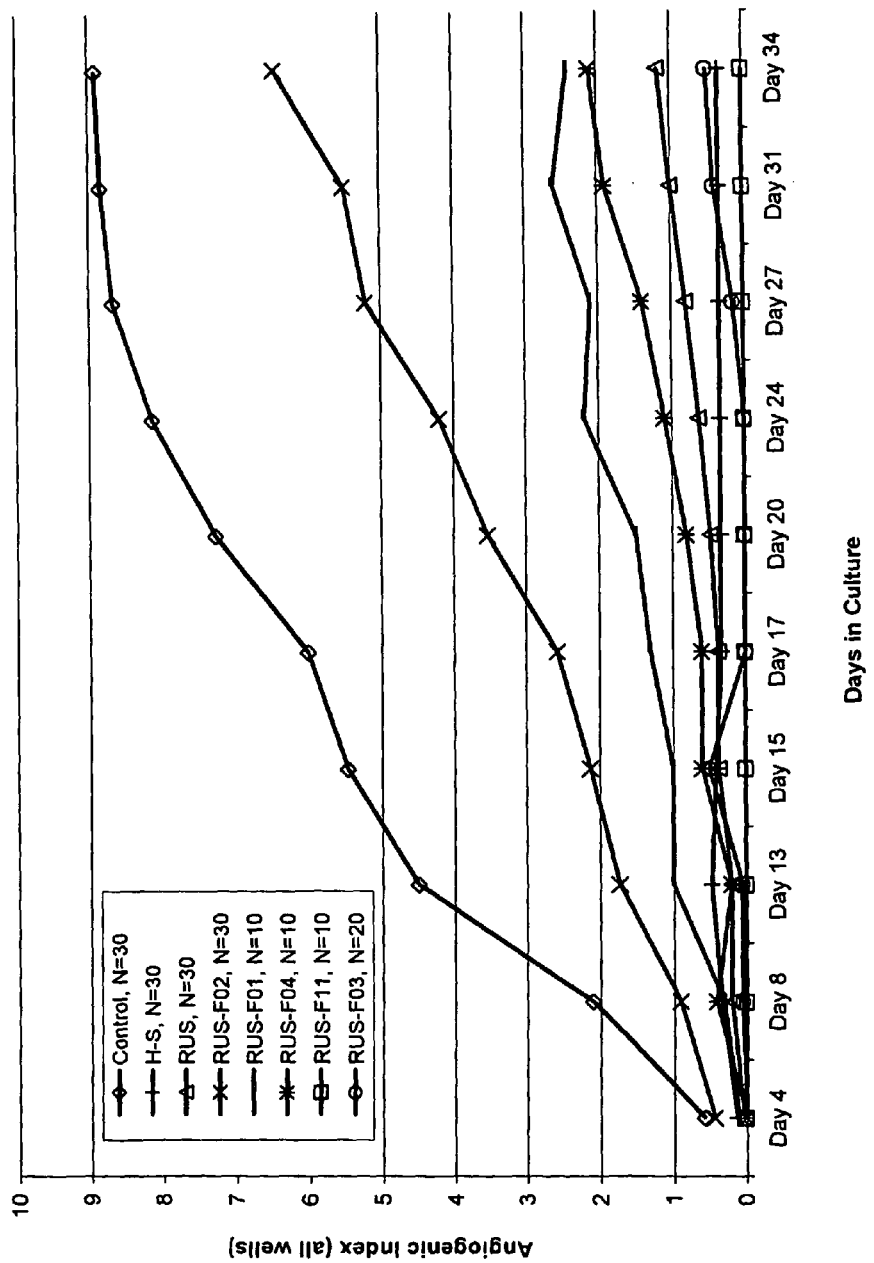
FIG. 4b illustrates the effects of several fractions from one of the Chinese blackberry leaf extracts (RUS-F) at a 0.1% concentration on angiogenesis (both initiation and proliferation) in human placental vein discs as measured by an angiogenic index.
Figure 4C:
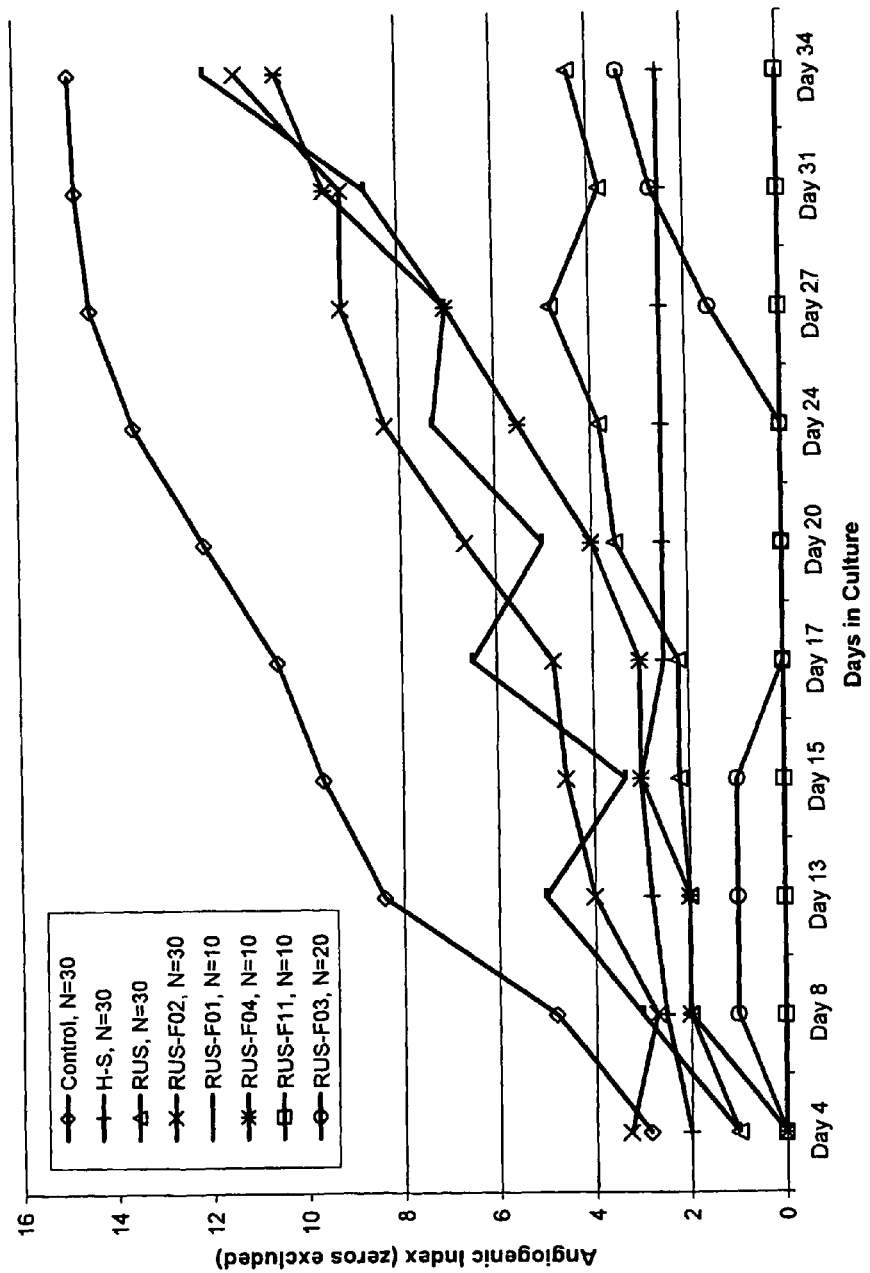
FIG. 4c illustrates the effects of several fractions from one of the Chinese blackberry leaf extracts (RUS-F) at a 0.1% concentration on angiogenesis in human placental vein discs as measured by an angiogenic index after removing discs with a zero angiogenic index (i.e., discs that never initiated an angiogenic response).

As shown in FIG. 4a, the initiation of angiogensis was totally inhibited by RUS-F11, nearly completely inhibited by RUS-F03, somewhat inhibited by RUS-F01 and RUS-F04, but not inhibited by RUS-F02. Similar results were seen in the angiogenic index both with (FIG. 4b) and without zero data points (FIG. 4c).

These results indicate that at least two active fractions of RUS-F that inhibit angiogenesis: RUS-F03 and RUS-F11.

EXAMPLE 7

Inhibitory Effects of a Purified Chinese Blackberry Extract (RUSF260) on Angiogenesis To test the effectiveness of purified Chinese blackberry extracts on angiogenesis, human placental vein discs (PVD) were grown in HPVAM supplemented with a purified RUSF260 fraction (0.025%). The control medium was supplemented with similar concentrations of NaCl. Two groups each with 30 PVDs were used for the control and for the RUSF260 fraction. The PVDs were allowed to grow for six days in only HPVAM before adding the Chinese blackberry extract. After addition of the extract, every two to three days, the medium in each well was replaced, and each well was scored for both initiation of angiogenesis and angiogenic index.

Figure 5A:
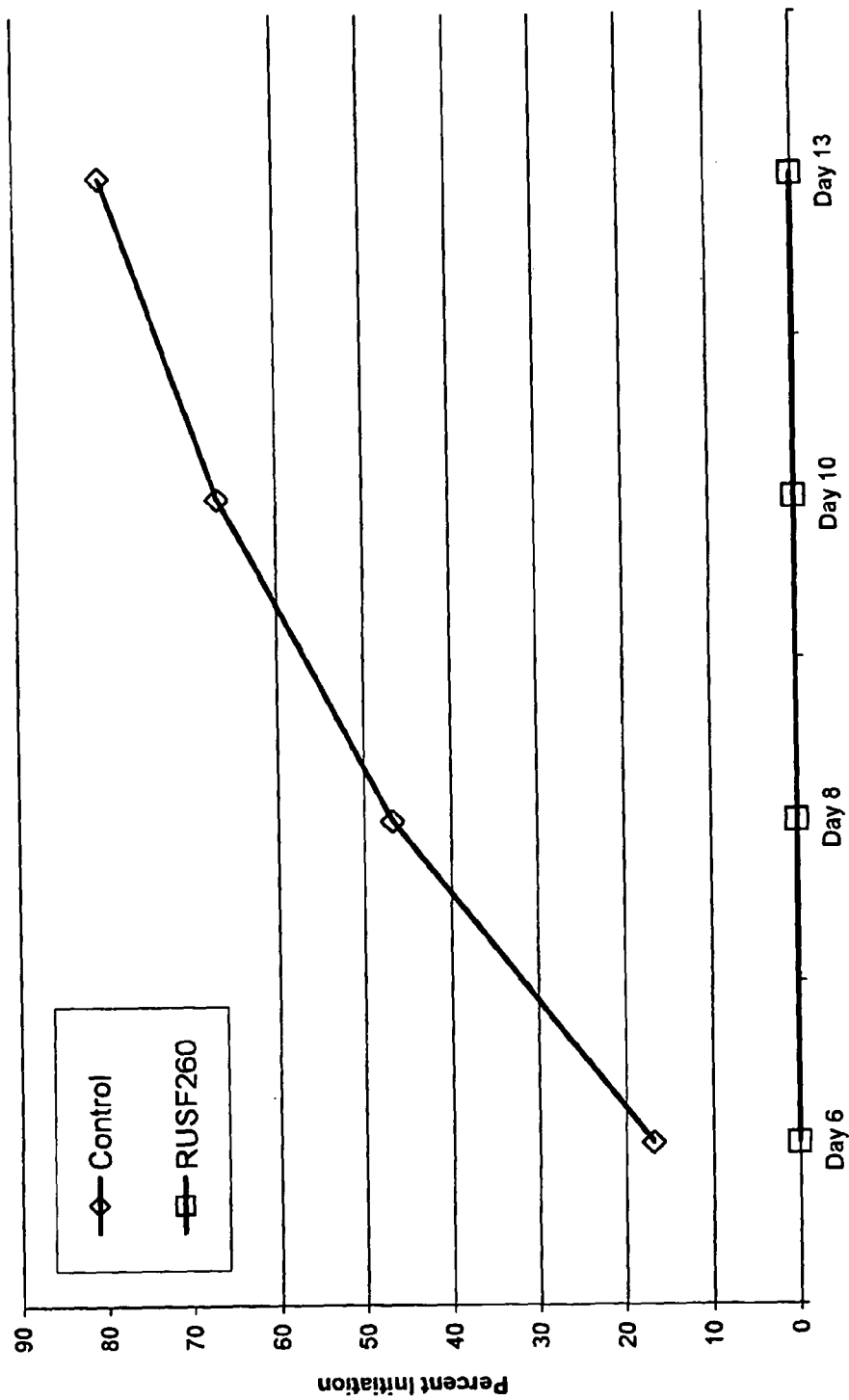
FIG. 5a illustrates the effect of a purified compound isolated from the leaf extract of Chinese blackberry (0.025% RUSF260) on the initiation of angiogenesis in human placental vein discs.
Figure 5B:
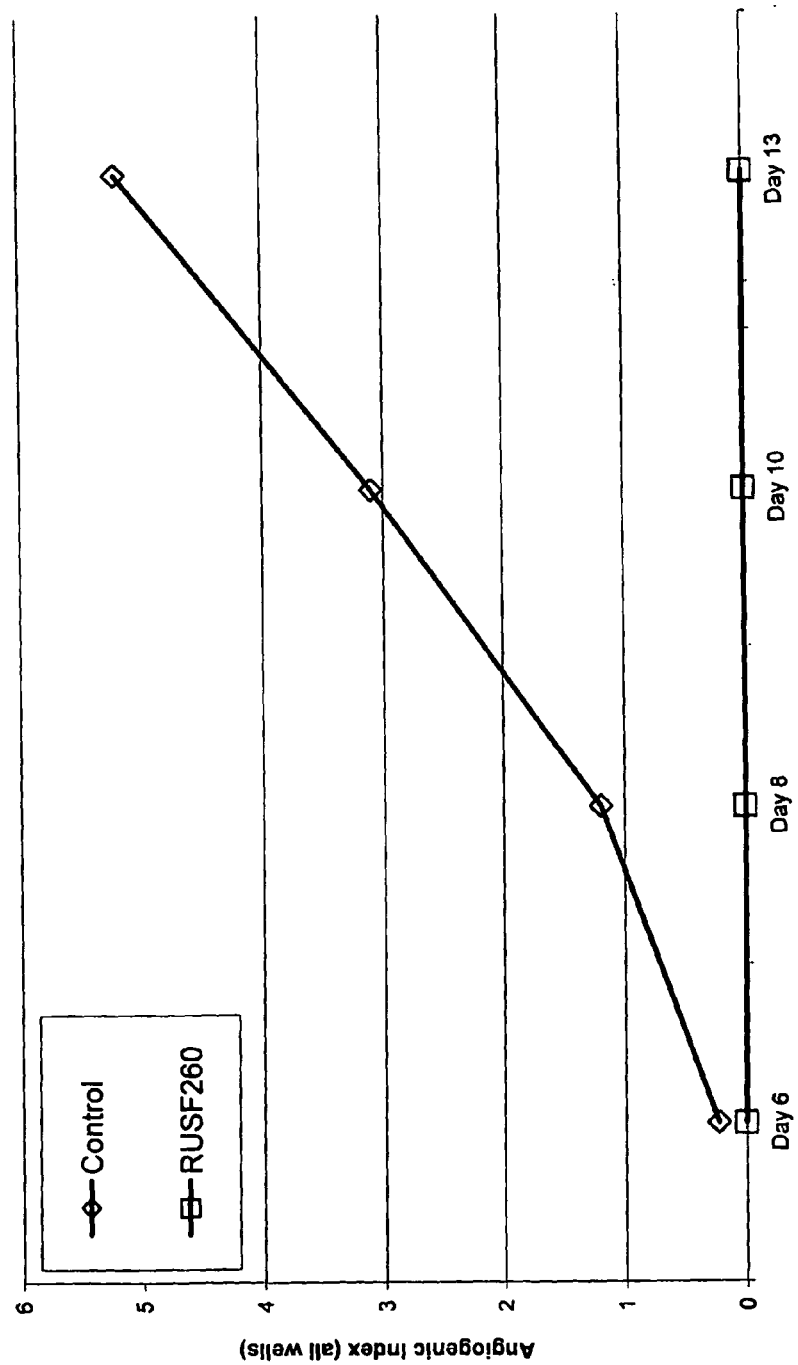
FIG. 5b illustrates the effect of a purified compound isolated from the leaf extract of Chinese blackberry (0.025% RUSF260) on angiogenesis (both initiation and proliferation) in human placental vein discs as measured by an angiogenic index.
Figure 5C:
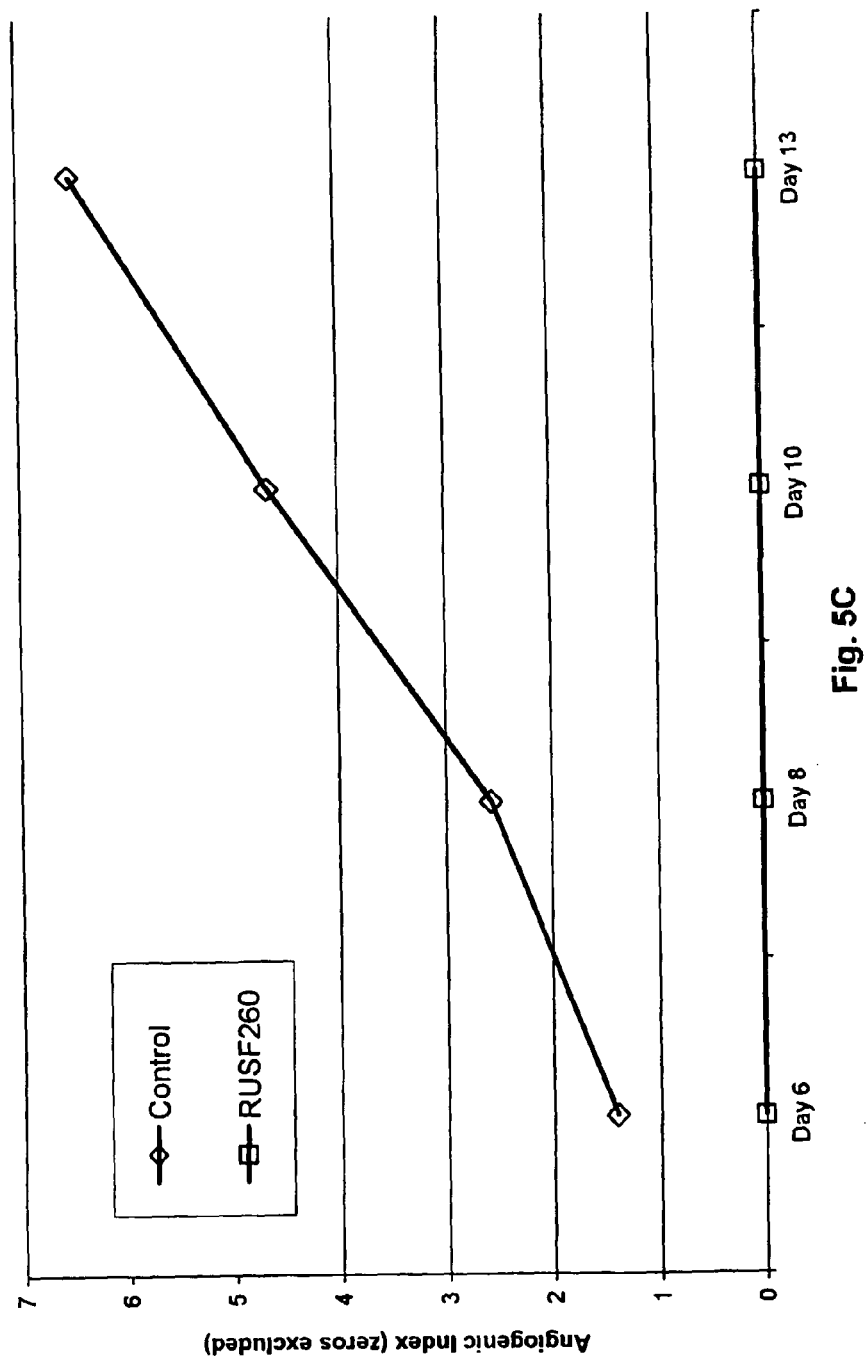
FIG. 5c illustrates the effect of a purified compound isolated from the leaf extract of Chinese blackberry (0.025% RUSF260) on angiogenesis in human placental vein discs as measured by an angiogenic index after removing discs with a zero angiogenic index (i.e., discs that never initiated an angiogenic response).

As shown in FIG. 5a, the initiation of angiogenesis was totally inhibited by 0.025% RUSF260. Similar results were seen in the angiogenic index with and without the zero data points. See FIG. 5b and FIG. 5c. (In FIGS. 5a and 5b, each data point represents an average of 30 observations; and in FIG. 5c, each data point represents an average of 20 observations.) These results indicated that the component labeled RUSF260 was a very effective anti-angiogenic agent. This component was then identified as gallic acid by the methods described in Example 2.

EXAMPLE 8

Inhibitory Effects of Various Concentrations of Gallic Acid on Angiogenesis

To test the effectiveness of gallic acid on angiogenesis, gallic acid was purchased as described in Example 2, and dissolved in Medium 199 (Gibco) to reach concentrations ranging from $10^{-3}$ M to $10^{-10}$ M. These concentrations were added to PVDs that had been grown for four days in HPVAM. After addition of the various extracts, every two to three days, the medium in each well was replaced, and each well was scored for both initiation of angiogenesis and angiogenic index.

Figure 6A:
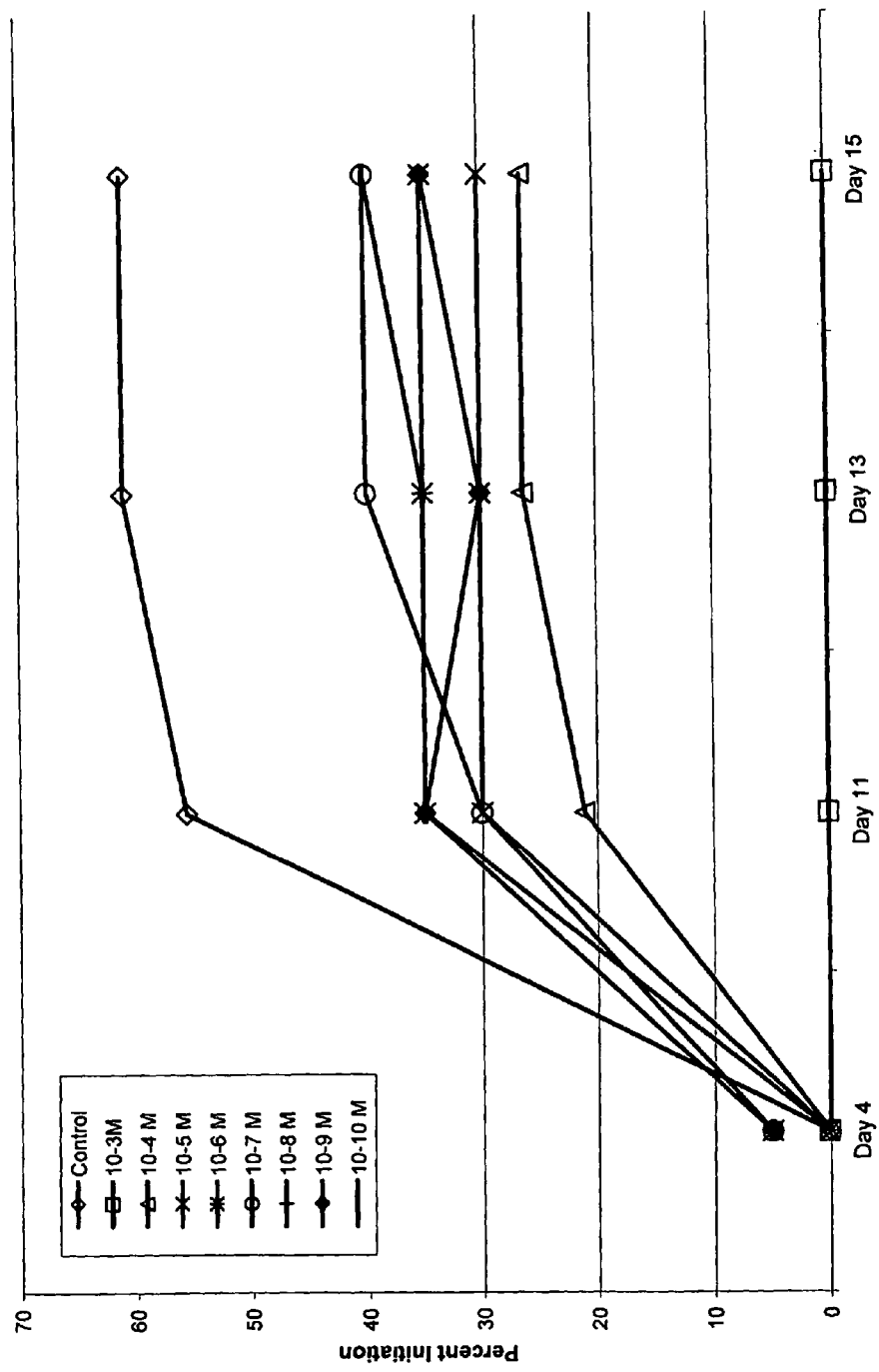
FIG. 6a illustrates the effect of several concentrations of gallic acid on the initiation of angiogenesis in human placental vein discs.

As shown in FIG. 6a, gallic acid at $10^{-3}$ M totally inhibited the initiation of angiogenesis. The percent inhibition by gallic acid was dependent on the concentration. Percent initiation decreased to 56% with $10^{-4}$ M, 50% at $10^{-5}$ M. and 33% up to $10^{-10}$ M. Thus even at the lower concentrations, gallic acid is an inhibitor of angiogenic initiation. (In FIG. 6a, each data point represents an average of 18 to 20 observations.)

Figure 6B:
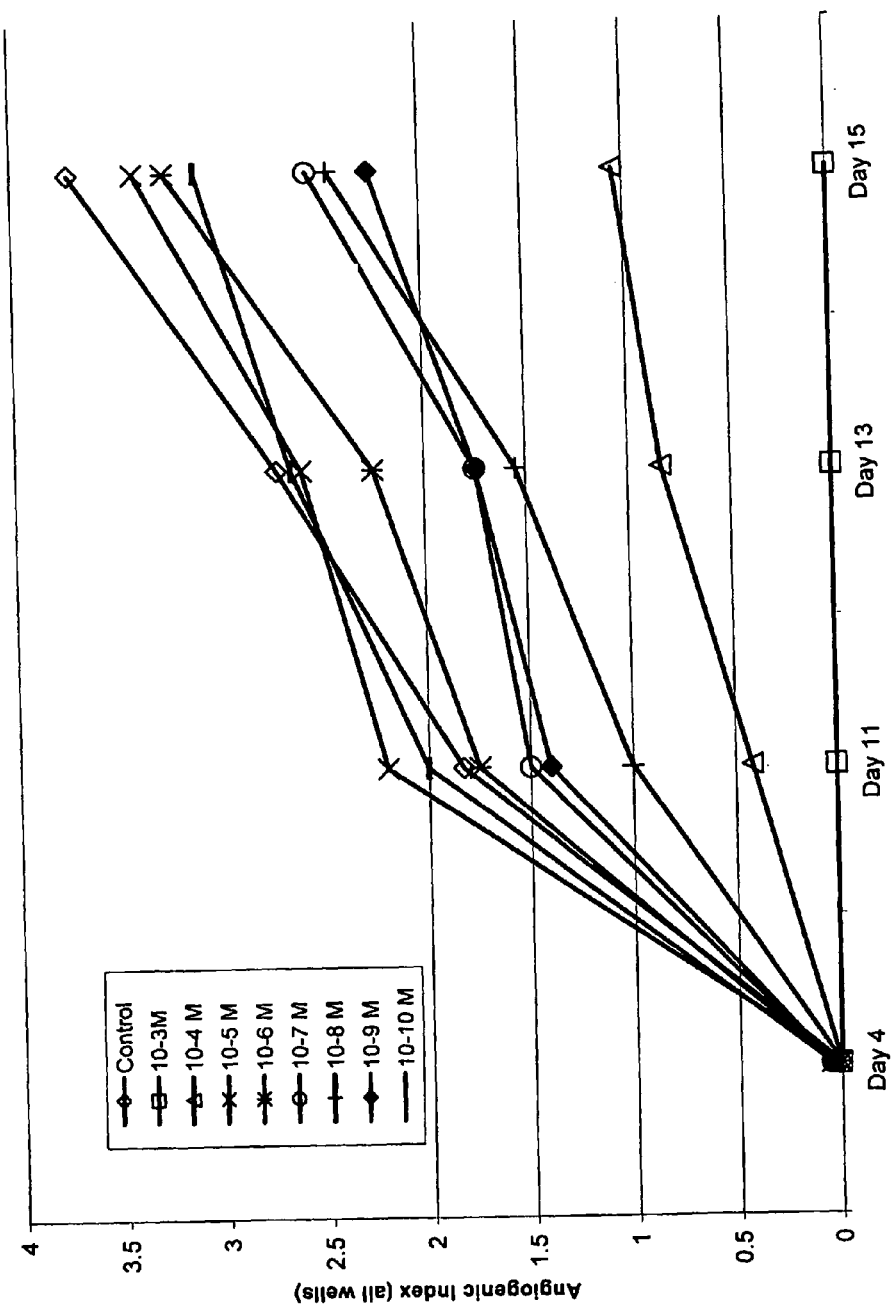
FIG. 6b illustrates the effect of several concentrations of gallic acid on angiogenesis (both initiation and proliferation) in human placental vein discs as measured by an angiogenic index.

When initiation and proliferation are considered together, as measured by the mean AI with the zero points included (FIG. 6b), gallic acid at $10^{-3}$ M again totally inhibited angiogenesis. (In FIG. 6b, each data point represents an average of 18 to 20 observations.) However, the inhibitory effect of gallic acid stopped at concentrations of $10^{-6}$ M and lower. When only proliferation is considered by looking at the mean AI without the zero points (FIG. 6c), only concentrations greater than $10^{-4}$ M showed inhibition. (In FIG. 6c, each data point represents an average of between 5 and 11 observations.)

Thus gallic acid in concentrations greater than $10^{-4}$ M will be effective in inhibiting angiogenesis, with the effect being greater at $10^{-3}$ M.

EXAMPLE 9

Inhibitory Effects of Extracts from Plants Known to Have Gallic Acid

Extracts from rhubarb, persimmon and dogwood berry were isolated as described in Example 4. These three plants were known or were found (See Example 16) to contain gallic acid. The extracts were used in the angiogenesis assay to test for inhibition of angiogenesis. PVDs were grown and prepared as described in Example 1 for eight days before addition of the extracts. The extracts were added to HPVAM to a final concentration of 0.1%. After addition of the various extracts, every two to three days, the medium in each well was replaced, and each well was scored for both initiation of angiogenesis and angiogenic index. In addition, a positive control group was established using a heparin-steroid (21-phosphate hydrocortisone) mixture (300 μg/ml and 350 μg/ml, respectively), which was previously found to reduce angiogenesis by 30 to 40%. An untreated control group was also established. The PVDs were scored, and the media changed every two to three days.

Figure 7A:
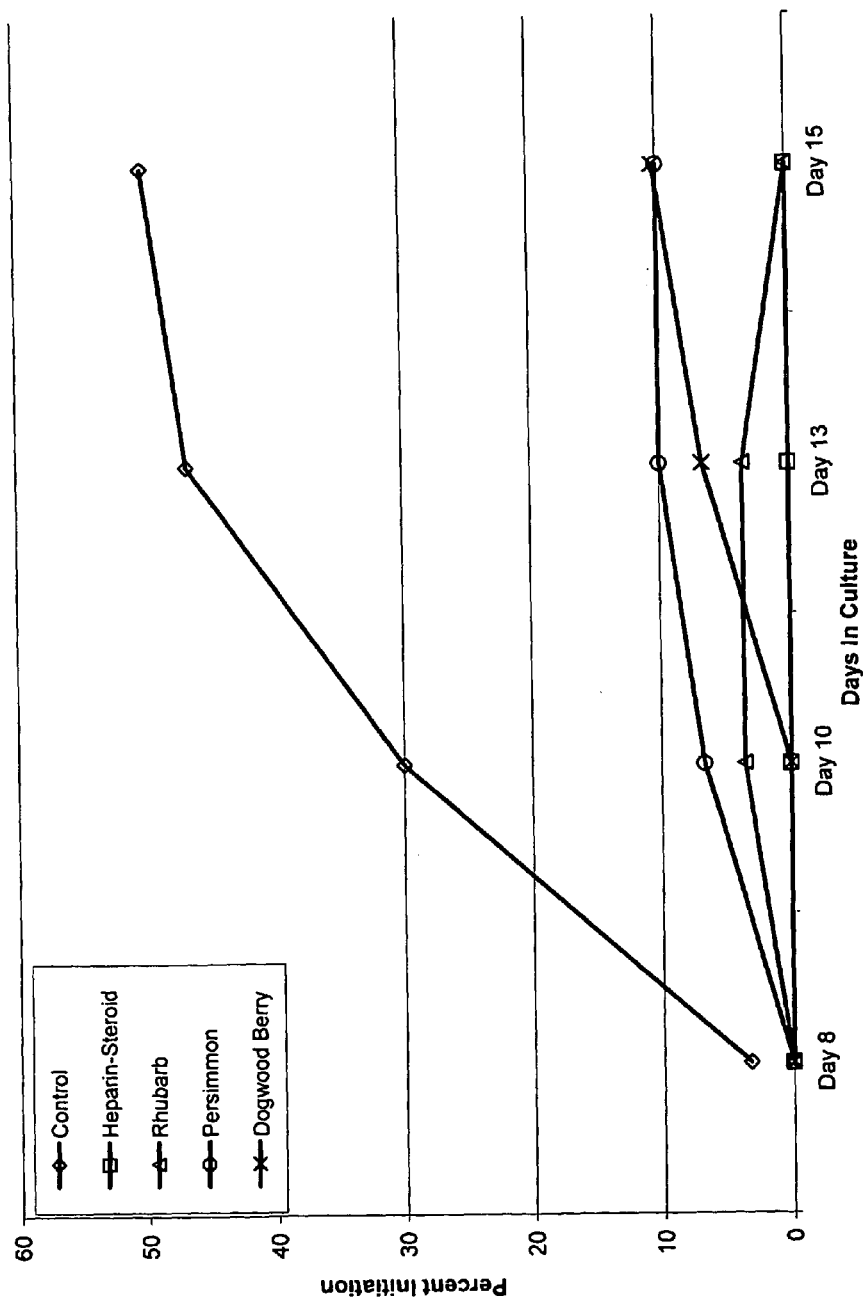
FIG. 7a illustrates the effect of extracts from several plants known or found to contain gallic acid on the initiation of angiogenesis in human placental vein discs.
Figure 7B:
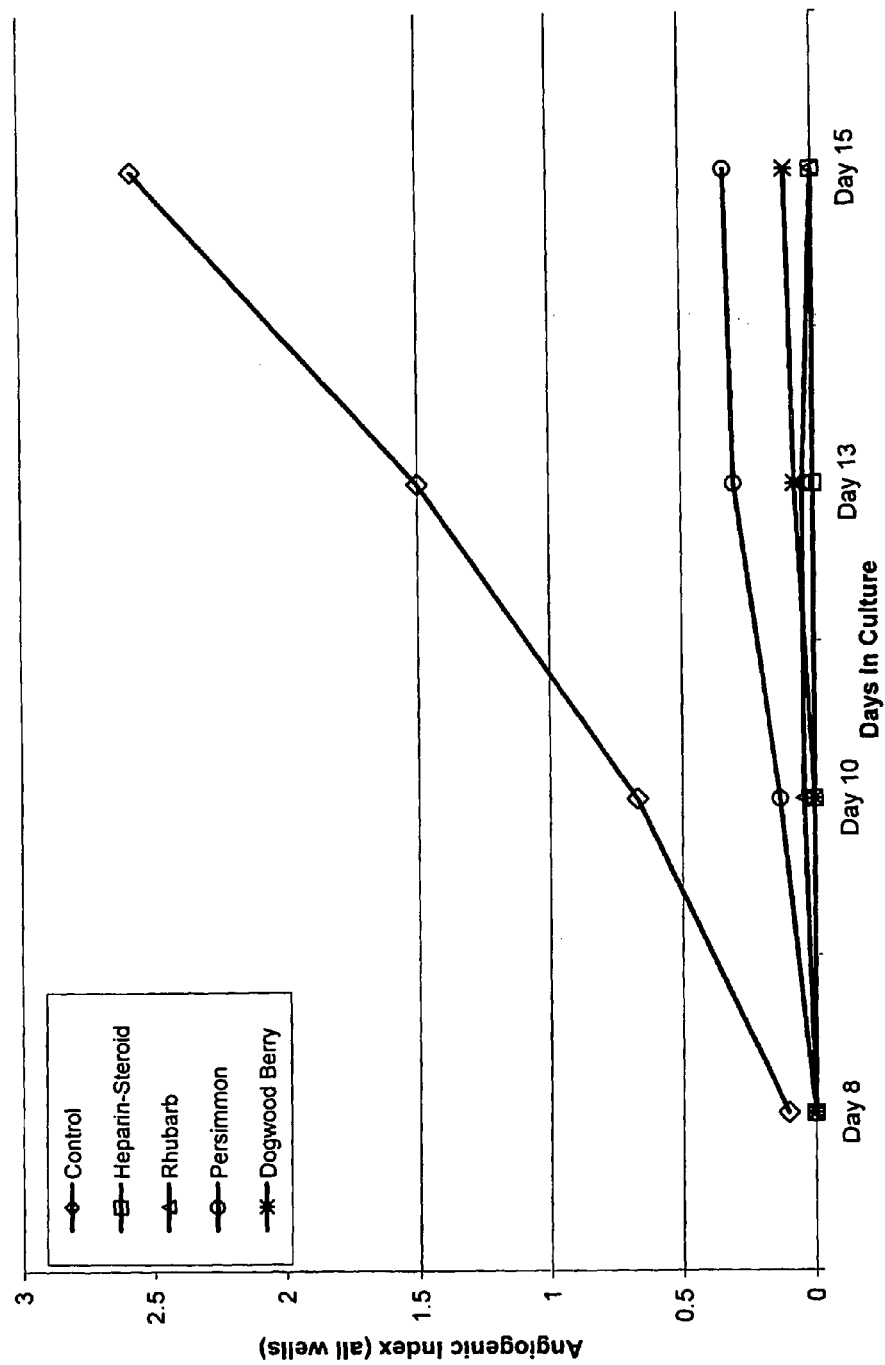
FIG. 7b illustrates the effect of extracts from several plants known or found to contain gallic acid on angiogenesis (both initiation and proliferation) in human placental vein discs as measured by an angiogenic index.
Figure 7C:
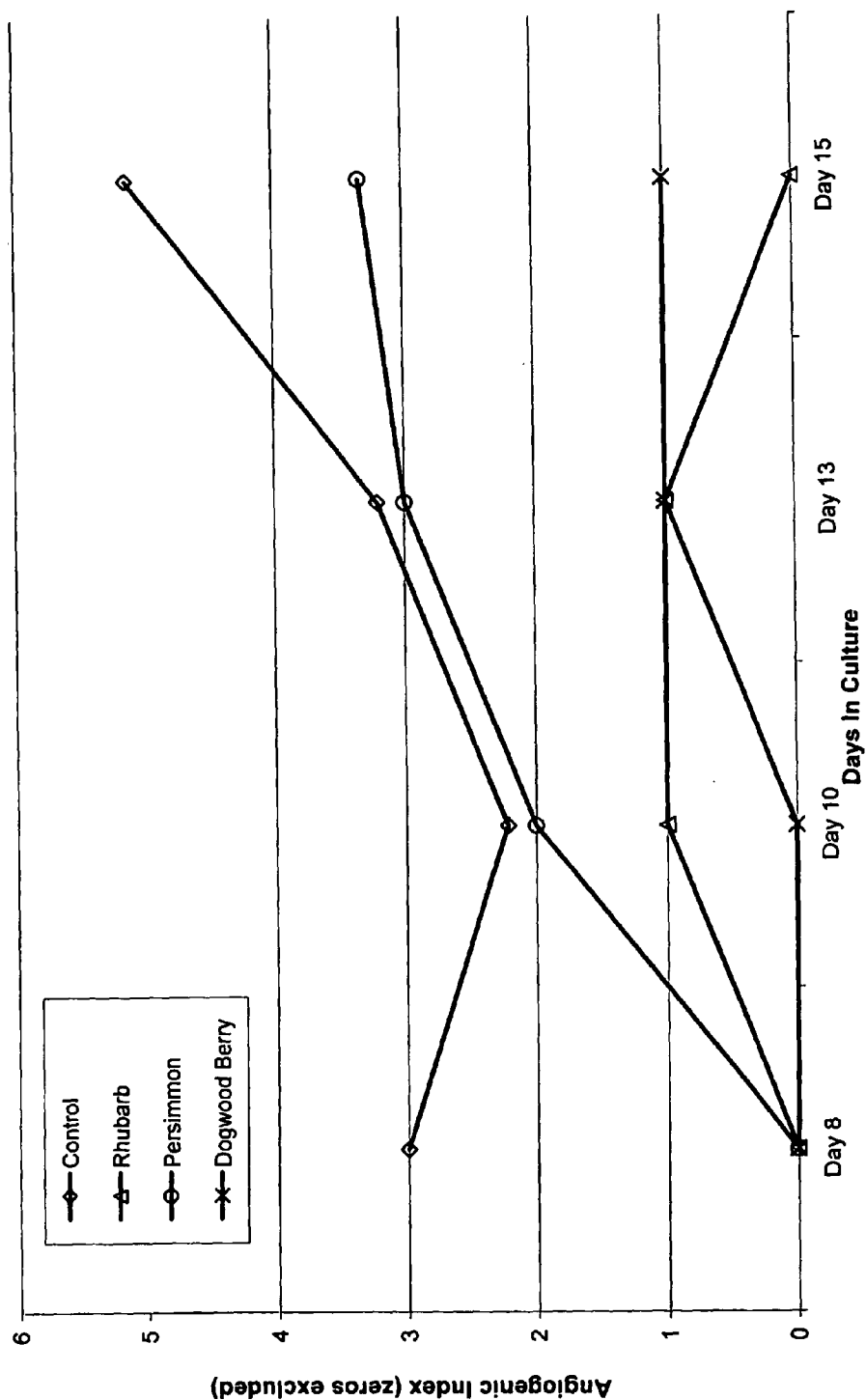
FIG. 7c illustrates the effect of extracts from several plants known or found to contain gallic acid on angiogenesis in human placental vein discs as measured by an angiogenic index after removing discs with a zero angiogenic index (i.e., discs that never initiated an angiogenic response).

As shown in FIG. 7a, all three extracts showed 80 to 100% inhibition of initiation of angiogenesis. (In FIG. 7a, each data point represents an average of 28 to 30 observations.) This indicates that extracts of plants known to have gallic acid are effective inhibitors of angiogenesis. A similar result was seen when initiation and proliferation are considered together as measured by the mean AI with the zero points added. (FIG. 7b; each data point represents an average of between 28 to 30 observations). However, when only proliferation is considered (FIG. 7c, mean AI without the zero points), while both rhubarb and dogwood berry inhibited the growth of angiogenesis, the persimmon extract did not. (In FIG. 7c, each data point represents an average of between 3 and 8 observations.) This may be due to differences in the other components in the extracts or in the concentration of gallic acid in the extracts.

EXAMPLE 10

Effect of Tannic Acid, a Derivative of Gallic Acid, on Angiogenesis

Tannic acid is a conjugated form of gallic acid, a gallotannin, with a molecular weight of 1701.23 and a formula of $C_{76}H_{52}O_{46}$. Tannic acid can be hydrolyzed to monomers of gallic acid and glucose. Tannic acid was commercially purchased (Sigma Chemical Co., St. Louis, Mo.), and was tested in the human placental vein angiogenesis assay at a concentration of 0.1% in HPVAM. Included in the assay were an untreated control and a positive heparin-steroid control as described in Example 9.

Figure 8A:
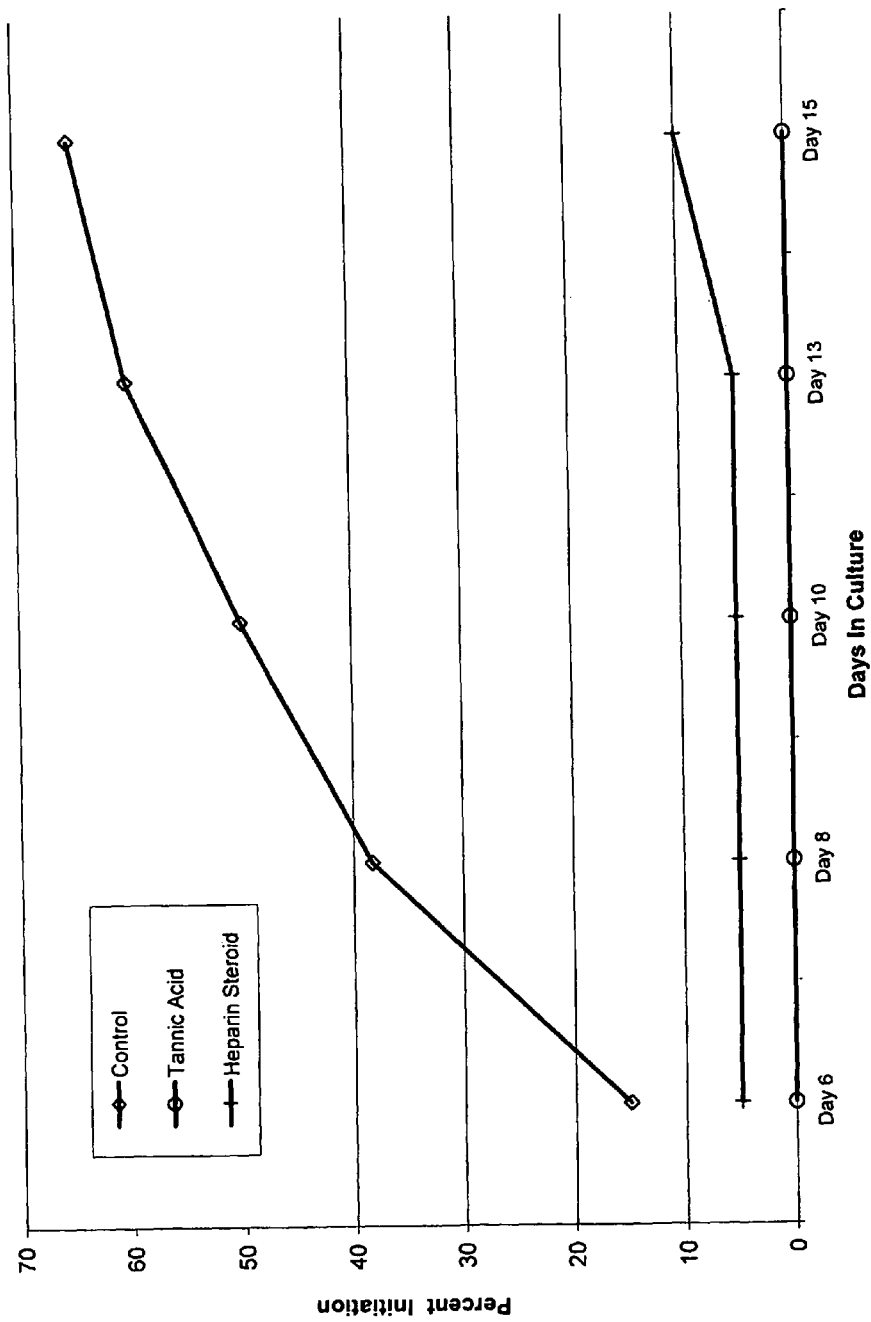
FIG. 8a illustrates the effect of tannic acid (a derivative of gallic acid) on the initiation of angiogenesis in human placental vein discs.
Figure 8B:
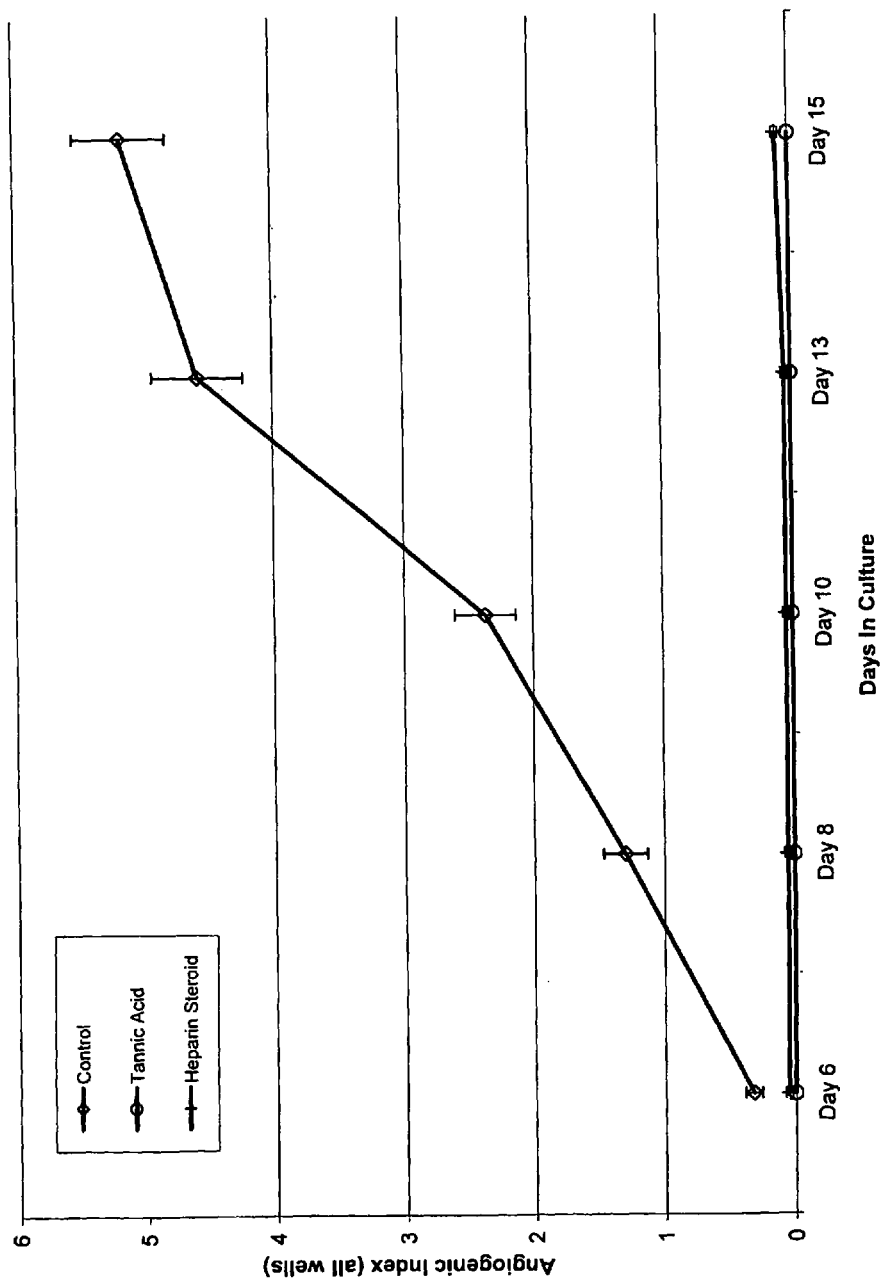
FIG. 8b illustrates the effect of tannic acid (a derivative of gallic acid) on angiogenesis (both initiation and proliferation) in human placental vein discs as measured by an angiogenic index.
Figure 8C:
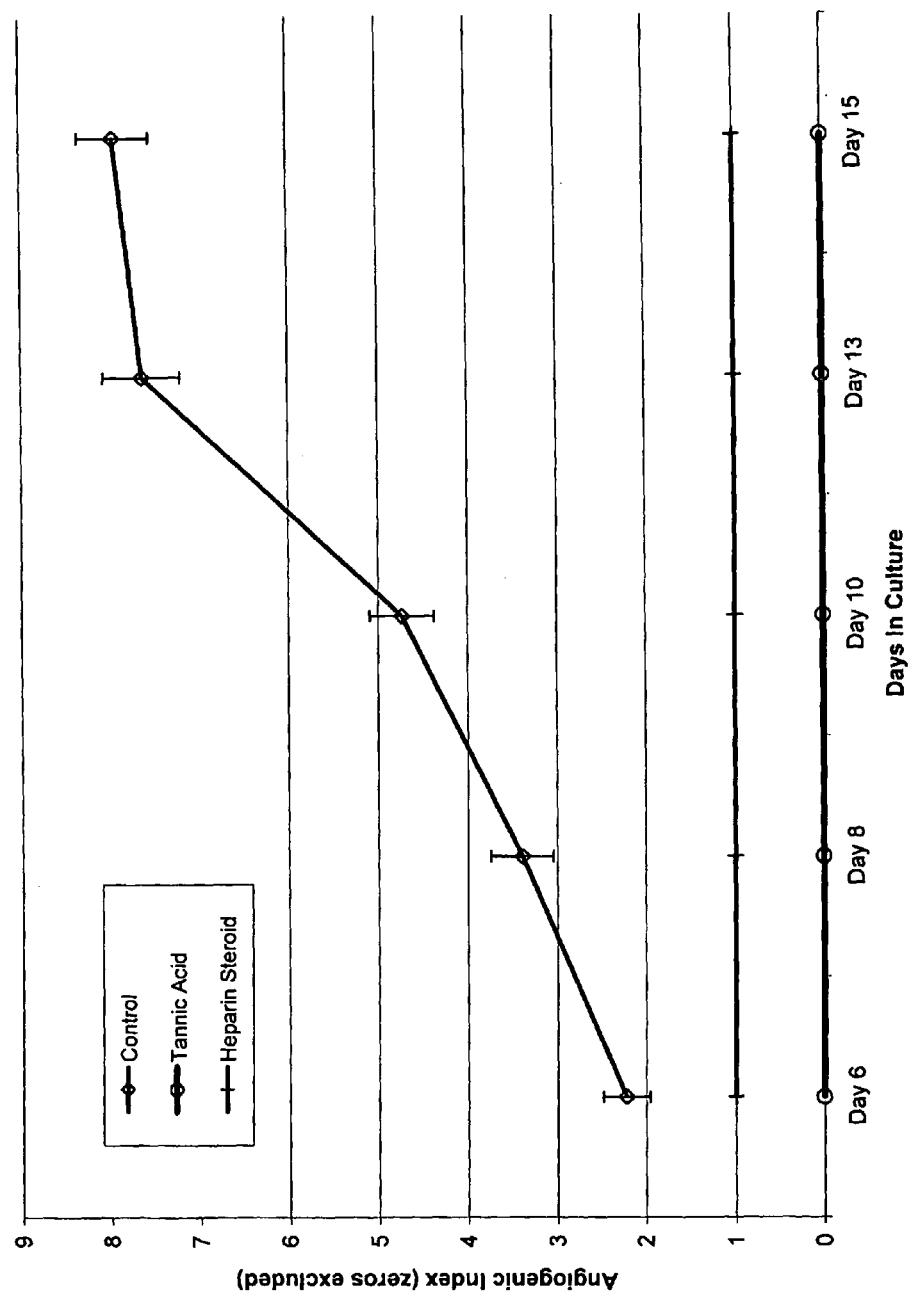
FIG. 8c illustrates the effect of tannic acid (a derivative of gallic acid) on angiogenesis in human placental vein discs as measured by an angiogenic index after removing discs with a zero angiogenic index (i.e., discs that never initiated an angiogenic response).

As seen in FIG. 8a, 0.1% tannic acid inhibited the initiation of angiogenesis even better than the positive heparin-steroid control. A similar result is seen in FIG. 8b when both initiation and proliferation are considered. (In FIGS. 8a, 8b, and 8c, each data point represents either an average of 10 (tannic acid), 60 (control), or 20 (heparin-steroid control) observations.) The vertical bars at the data points in FIGS. 8b and 8c represent one standard error of the mean.

EXAMPLE 11

Effect of Chinese Blackberry Extract or Gallic Acid on Psoriasis

To test the effectiveness of a gallic acid or a plant extract (Chinese blackberry or other) high in gallic acid on psoriasis, patients with psoriasis will be selected. All patients will be asked to continue using whatever therapy they have been using for the psoriasis. Each patient will be given two distinct 8 gm jars of a gel, one a gel with gallic acid (or a plant extract) (the "experimental gel") and one a control gel. The jars will not indicate which contains the gallic acid. The patients will be randomly divided on which arm (right or left) will be treated with the experimental gel, and which arm treated with the control gel. The patients will be asked to treat the affected area topically twice a day. Pre-study photographs of psoriatic lesions on both arms will be taken. Patients will be monitored and photographed weekly or bi-weekly. Patients will also be asked to rate the condition of their skin. An unbiased observer will also rate the lesions or plaques on the skin, using a 9-point grading system. The 9-point grading system is the sum of a grade of 0 to 3 for each of three categories—erythema, scale, and elevation.

The experimental gel will be prepared by using purchased gallic acid or using plant extract that has been freeze-dried into a powder. The powder will then be compounded into a gel at a concentration of about 20% wt/vol, by initially using rosewater if necessary to mask any odor differences. Then Krisgel liquid, cellulose hydroxy propyl ether (Professional Compounding Centers of America, Houston, Tex.), will be added to bring the volume to the final total, and the combination mixed until it gelled. The control will be the same rosewater/Krisgel liquid mixture without the gallic acid or plant extract.

It is believed that the arm treated with the gel with gallic acid or plant extract will show significant improvement over the control arm. This improvement should be reflected both by the patients objective scoring and by the rating from the independent observer.

In similar experiments, gallic acid or a plant extract will be tested for effectiveness of a topical administration against other skin disorders that involve angiogenesis, e.g., Kaposis sarcoma and some skin cancers.

EXAMPLE 12

Treatment of Proliferative Retinopathies by Chinese Blackberry Extract or Gallic Acid To test the effectiveness of gallic acid or an active extract of a plant known to contain gallic acid (Chinese blackberry or other), patients with symptoms of proliferative retinopathies, e.g., diabetic retinopathy, will be divided into two groups. One group will receive a placebo; and the other gallic acid or a plant extract, administered either by injection or orally in a tablet form, per os. The treatment will be administrated during prolonged periods of time after disease onset to inhibit pathological neovascularization. The degree of neovascularization will be followed using standard methods to measure vascularization in the eye. The treatment with gallic acid or with a plant extract high in gallic acid will result in a decrease in the degree of preexisting vascularization and will prevent the development of new angiogenic vessels.

EXAMPLE 13

Oral Versus Injected Chinese Blackberry Extract for Angiogenesis Inhibition

An experiment was conducted to test the efficacy of the Chinese blackberry extract (RUS) to inhibit angiogenesis when given orally to a rat. Fifteen male Osborne-Mendel rats (300 g each; from a breeding colony at Pennington Biomedical Research Center, Baton Rouge, La.) were used. Each rat was housed individually and fed rat chow ad libitum. The rats were randomized into five groups of three rats. Group 1 received no treatment and served as the control. Group 2 was injected intraperitoneally for three days with only 0.9% saline (w/v) (0.1 ml saline/100 g body weight) with a dose of 250 mg/day. Group 3 was injected intraperitoneally for three days with 250 mg of Chinese blackberry extract in 0.1 ml saline/100 mg body weight. For intraperitonial injection, the Chinese blackberry extract was vortexed and passed through a 0.22μ filter before suspension in sterile 0.9% saline (w/v). Group 4 was gavaged with 250 mg of Chinese blackberry extract (prepared as above) in 1 ml water daily for three days. Group 5 was gavaged with 750 mg of Chinese blackberry extract (prepared in saline as above) in ml water for three days. One to four hours after administering the last dose of the extract, the rats were sacrificed by guillotine and trunk blood was collected for the preparation of serum. The blood was then centrifuged to collect serum. The serum was used in the HPVAM angiogenesis model at a concentration of 10%, supplemented with 10% fetal bovine serum to provide growth factors. In the control, 20% FBS was used. For each rat serum, 10 wells were used. HPVAM explants were observed daily under an inverted phase scope and graded for the percentage wells that became angiogenic, as well as for the angiogenic index as described in Example 1.

Figure 9:
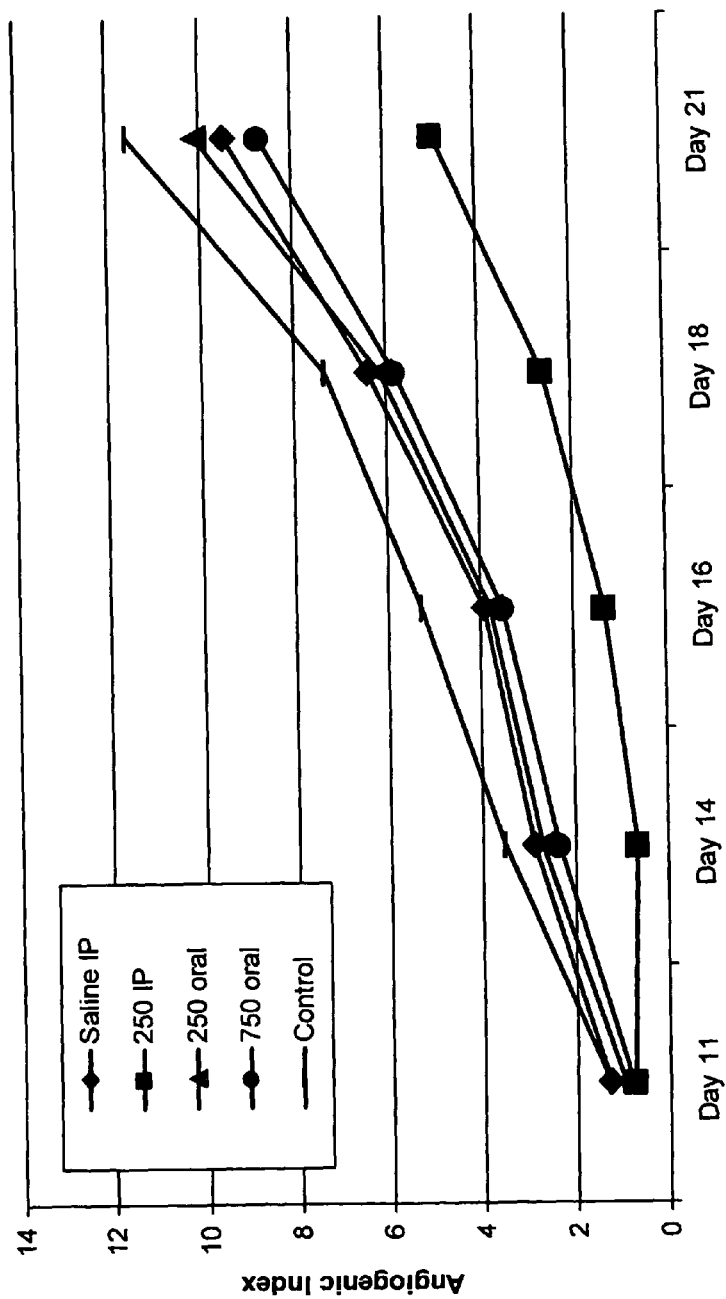
FIG. 9 illustrates the angiogenic activity of several serum samples isolated from rats that were given various doses of the RUS extract from *Rubus suavissimus* (Chinese blackberry) both orally and as an intraperitoneal injection (IP).

The results are shown in FIG. 9. Each point represents the mean angiogenic index for an individual rat. Serum from the rats that were injection with 250 mg/day of the RUS extract clearly inhibits angiogenesis when compared with the control. Although the serum from the rats given the RUS extract orally is not statistically different from the control, there is a suggestion of oral activity. In addition, there is a suggestion of a dose response since the line for the 750 mg/day dose lies below that for the 250 mg/day dose. It is believed that a larger oral dose would prove to be more effective.

EXAMPLE 14

Efficacy of Chinese Blackberry Extract (RUS) on Tumors

To further characterize the effect of Chinese blackberry extract as an anti-tumor agent, two Lewis rats (Charles River Laboratories; Wilmington, Mass.) were implanted with CA 20948 rat pancreatic tumors (Erasmus University; Rotterdam, The Netherlands), and the tumors allowed to grow until palpable. The tumor was measured weekly by the product of the two largest diameters (tumor area $cm^2$). One rat was injected intraperitoneally once a week with 1 ml sterile 0.9% saline. The other rat was injected intraperitoneally once a week with 200 mg Chinese blackberry extract (0.1%) in 1 ml 0.9% saline. The extract was initially sterilized by filtering through a 0.22 micron filter.

Figure 10:
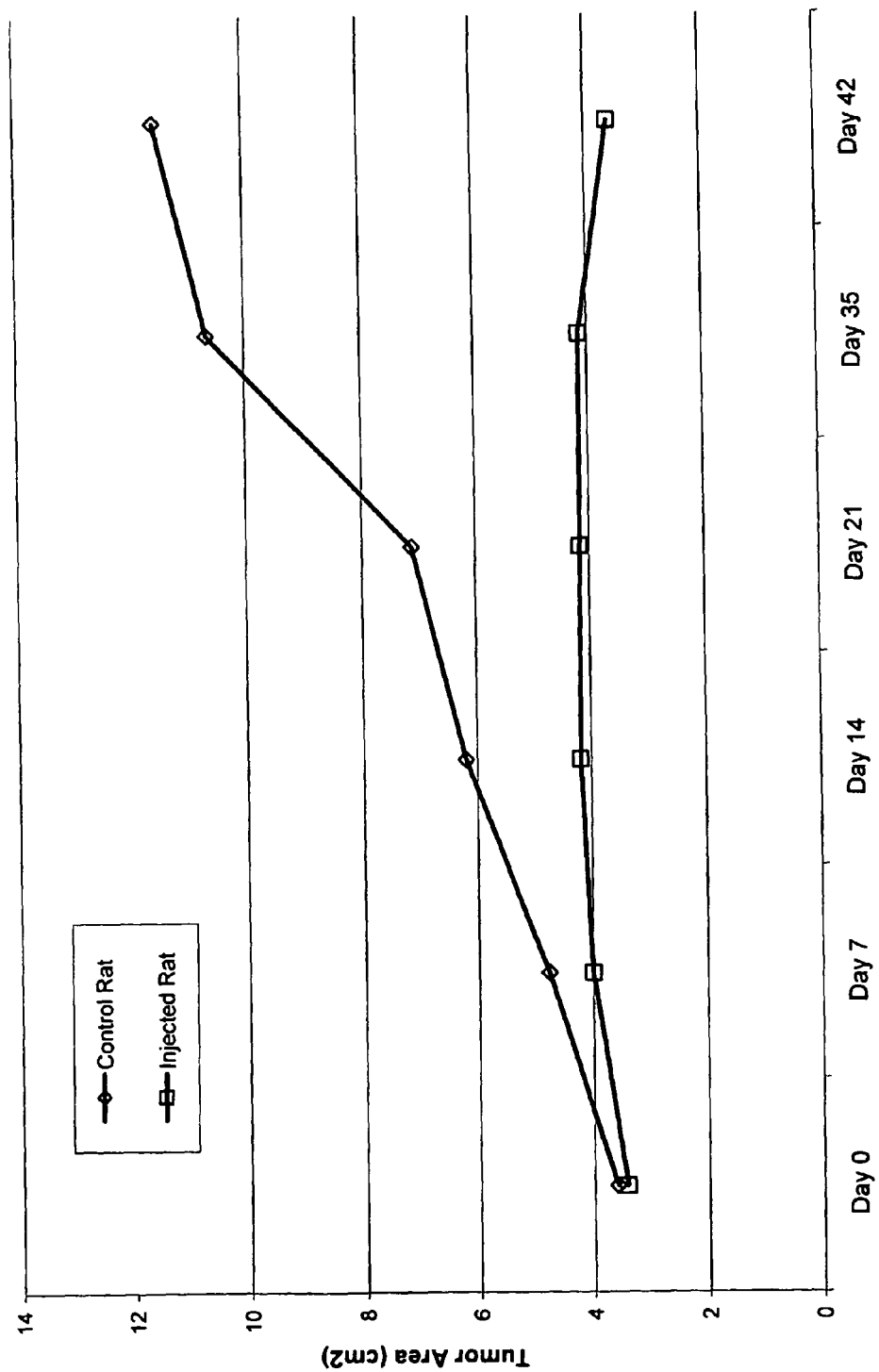
FIG. 10 illustrates the effect of a weekly intraperitoneal injection of the RUS extract (1%) on the size of pancreatic tumors in rats.

The results are shown in FIG. 10. FIG. 10 indicates the effect of the water-soluble Chinese blackberry extract on the absolute tumor area. As seen, the weekly treatment of a tumor-bearing rat with Chinese blackberry extract effectively blocked tumor growth for 42 days (only increased 15% over baseline), while the control tumor progressively increased in size (212% over baseline).

These results indicate that the water-soluble extract of Chinese blackberry contains potent anti-tumor inhibitors, possibly due to an anti-angiogenic activity.

EXAMPLE 15

Effect of Chinese Blackberry Extract on Corneal Neovascularization

To test the effects of the RUS extract on corneal neovascularization, male Long Evans pigmented rats were used. The rats were housed in individual cages and maintained under standard conditions. The experimental protocol was approved by the local Advisory Committee for Animal Resources. Forty eyes of 40 rats were used to study the effects of topical administration of the Chinese blackberry (RUS) extract or a placebo; only one eye of each animal was used as a treated or control eye.

RUS Chinese blackberry extract was reconstituted with deionized water to obtain a topical preparation. RUS extract (0.8 g) was added to 0.7 ml water and dissolved with repeated rounds of warming (37° C.) followed by extending vortexing. The solution was pH adjusted to 7.0 with 1 N NaOH. Then the volume was adjusted to 8 ml and the solution was sterile-filtered. Dilutions were prepared (1:10) using sterile water. Three concentrations were prepared for topical administration (0.1%, 1%, and 10%). To ensure the sterility, the final product was filtered using a 22 micron filter prior to use.

To induce corneal vascularization in rats, a silver nitrate cauterization was used as described by J. M. Mahoney et al., "Drug effects on the neovascularization response to silver nitrate cauterization of the rat cornea," Curr. Eye Res., vol. 4, pp. 531-535 (1998). All procedures were performed under general anesthesia induced by intraperitoneally administered ketamine hydrochloride and xylazine combination (94.7 mg/kg body weight). Also one drop of 0.5% topical proparacaine was applied to each cornea before the procedure. All corneas were cauterized by pressing the applicator stick (with a diameter of 1.8 mm) coated with 75% silver nitrate and 25% potassium nitrate to the central cornea for 8 sec under the operating microscope. Excess silver nitrate was removed by rinsing the eyes with 10 ml of a balanced salt solution and then gently blotting them with tissue paper. To increase the reproducibility of the injuries, one investigator cauterized all animals. Following cauterization, the rats were randomized to eliminate any potential bias in the degree of injury within the different groups. The rats were divided into four groups of ten each. Group 1 received 0.1% topical RUS extract; Group 2 received 1% topical RUS extract, Group 3 received 10% topical RUS extract, and Group 4 received saline. For each group, the treatment was administered two times a day for seven days. In all groups, treatment started immediately after cauterization.

After seven days, the animals in all groups were anesthetized as described above and their corneas evaluated by slit-lamp microscopy. Corneal photographs were taken with a 25× magnification using a digital camera attached to the slit-lamp microscope (Topcon SL-7E). Neovascularization in each cornea was evaluated using the technique of Mahoney et al. (1985). The evaluation was performed by an unbiased examiner. For each eye, the extent of the burn stimulus response was scored as 0 (no blister, not raised above corneal surface); +1 (small blister, raised slightly above the surface); +2 (medium blister, raised moderately above the surface); and +3 (large blister). The corneal surface covered with neovascular vessels was measured on the photographs as the percentage of the total area of the cornea. Image analysis was performed semi-automatically on each cornea using an image processing and analysis software program (BS200D-Image Analysis Software). The area of neovascularization was measured in terms of pixels, and its ratio to the entire corneal area was determined as the percentage of corneal neovascularization.

Only the corneas with a burn stimulus score of +1 or higher were included for the calculation of the mean burn stimulus and neovascularization scores in each group. Percent inhibition was calculated by comparing the mean percentage of neovascularization in each drug treated group to that in the control group. After scoring the burn stimulus and percentage of neovascularization for all groups, the animals were sacrificed in the seventh day.

For histopathology, following sedation using intraperitoneally administered ketamine hydrochloride and xylazine combination (94.7 mg/kg body weight), enucleation was performed before the animals were euthanized. Immediately after enucleation, penetration of the globe was performed with a 27-gauge needle, 1.0 mm from the limbus at the 3 and 9 o'clock meridians to allow fixative to fill the eyes rapidly. The eyes were then prepared for histologic examination using 2% paraformaldehyde, 3% glutaraldehyde fixative. After fixation for 24 hr, the eyes were removed from the fixative, and the corneas were dehydrated and sectioned. For pre-infiltration, ethanol and Technovit 7100 were used. The eyes were infiltrated overnight using Technovit 7100. The tissues were embedded in methacrylate overnight and cut at 3 μm intervals, then stained with 1% Toluidine blue for light microscopy.

Light microscopic examination was made of every microscopic section. Sections were evaluated by dividing the corneas into two halves through the center of the lesion and evaluated with regard to the intensity of new vessels, polymorphonucleated (PMN) leukocytes, edema and fibroblastic activity. The corneas were scored as 0 (no change), +1 (mild), +2 (moderate), and +3 (severe activity). An average histopathologic score for each cornea was calculated.

Statistical analyses were performed with a one-way analysis of variance (ANOVA) test and a Mann-Whitney U test using a SPSS statistical package (SPSS for Windows; Chicago, Ill.). A p value of <0.05 was considered as statistically significant.

In all eyes, the burn stimulus score was +1 or higher. The mean burn stimulus score did not show statistically significant difference between the treatment and the placebo groups ($p=0.714$). In gross examination, all eyes treated with Chinese blackberry RUS extract showed less inflammation during the treatment period with less eyelid edema and less ciliary injection. Table 1 shows the average burn stimulus, percentage of neovascularization, histopathologic scores and inhibition percentage of test drugs on the neovascularization response in comparison with the control for each group. Topical application of 10% RUS solution caused a significant decrease in percentage of neovascularization in response to silver nitrate cauterization ($p=0.024$). Topical application of the 0.1% and 1% RUS extracts showed no significant difference compared to the control eyes ($p=0.867$, 0.455, respectively). In drug-treated and placebo eyes, the severity of burn stimulus response was positively correlated with the extent of neovascular growth, which means the lesser the intensity of the burn stimulus, the lesser the extent of neovascularization ($p<0.05$). Also, the histopathologic evaluation of Group 3 showed significantly lesser neovascularization compared to control group ($p<0.05$). (Data not shown).

EXAMPLE 16

Determination of Gallic Acid in Two *Rubus* Species and Persimmon

Leaves and berries of *Rubus fruticosus* (blackberry; obtained commercially in Baton Rouge, La.) were extracted separately for the analyses of gallic acid. Leaves were first oven-dried at 60° C. for 72 hours and then ground to 6-mm or smaller particles. Fifty-five grams of the leaf particles were soaked for 1 hr with 500 ml deionized water (1:10 w/v) in a one-liter flask. The soaked solution was heated on a heating mantle to a boil for 30 min. The aqueous extract was centrifuged at 12,000 rpm. The supernatant was collected, concentrated in a rotary evaporator before being freeze-dried to an extract powder labeled as "RUF-L."

The cut and sifted fresh 300 g berries of *Rubus fruticosus* were extracted in a similar way as in the leaves described above and an extract powder was obtained and labeled as "RUF-F."

Berries of *Rubus occidentalis* (black raspberry; obtained commercially in New Orleans, La.) were extracted the same way as above and a freeze-dried extract powder was obtained and labeled as "RUO-F."

Calyx and fruit peels of persimmon (*Diospyros khaki* L.) were oven-dried and ground to 6-mm or smaller particles. The ground samples were extracted using the above described method. An extract powder was obtained and labeled as "SD."

The above-obtained extracts were analyzed for their gallic acid concentrations using HPLC by the following method: A C18 column of 150 cm long with an internal diameter of 4.6 mm with particle size 5 μm was used. The mobile phase was 10% methanol and 90% water containing 0.15% (v/v) acetic acid. A diode array UV detector was used to measure UV absorption from 190 nm to 440 nm. UV absorption of gallic acid was measured as a wavelength of 254 nm. Gallic acid was eluated at 6.8 min. The presence of gallic acid was determined by the retention time and the UV absorption spectrum from 190 nm to 440 nm by the diode array. A standard calibration curve for gallic acid was developed and used to quantitate the gallic acid concentrations in the plant extracts.

RUF-L contained 0.11% gallic acid; RUF-F contained 0.02% gallic acid; RUO-F contained 0.02% gallic acid; and SD contained 0.31% gallic acid.

EXAMPLE 17

Angiogenesis Inhibition of *Rubus Fruticosus* (Blackberry) Leaf and Berry Extracts and Sweet Leaf Tea (*Rubus Suavissimus*) Extract To test if other species from the *Rubus* genus have anti-angiogenic activity as observed in *Rubus suavissimus*, *Rubus*

TABLE 1

Inhibition of neovascularization by the drugs

| Drug | No. eyes | Mean burn stimulus score (±SEM)[a] | Mean neovascularization % (±SEM) | Mean histopathologic score (±SEM) | % Inhibition[b] | p value |
|---|---|---|---|---|---|---|
| 0.1% RUS | 10 | 2.3 ± 0.66 | 68.06 ± 13.6 | 2.50 ± 0.5 | 12.8 | 0.867 |
| 1% RUS | 10 | 2.1 ± 0.70 | 60.45 ± 15.4 | 2.40 ± 0.5 | 20.4 | 0.455 |
| 10% RUS | 10 | 2.3 ± 0.67 | 30.78 ± 10.4 | 1.90 ± 0.5 | 50.0 | 0.024 |
| Control | 10 | 2.1 ± 0.56 | 80.86 ± 9.1 | 2.90 ± 0.31 | | |

[a]SEM means the standard error of the mean
[b]% Inhibition is calculated as (1 − [Mean % neovascularization for each test compound/Mean % neovascularization for the control group]) × 100 fruticosus (blackberry) was tested in the HPVAM assay. Human placental vein discs (PVD) were grown in HPVAM supplemented with a leaf extract (RUF-L) and a berry extract (RUF-F) of *Rubus fruticosus*, prepared as above in Example 16. Ten PVDs per group and 30 PVDS per control and the heparin-steroid group were used. The control medium was supplemented with similar concentrations of NaCl. The positive control group was treated with a heparin-steroid (21-phosphate hydrocortisone) mixture (300 µg/ml and 350 µg/ml, respectively), which was previously found to reduce angiogenesis by 30 to 40%. The PVDs were allowed to grow for five days in only HPVAM before adding the RUF-L and RUF-F extracts. After addition of the various extracts, every two to three days, the medium in each well was replaced, and each well was scored for both initiation of angiogenesis and angiogenic index.

Figure 11A:
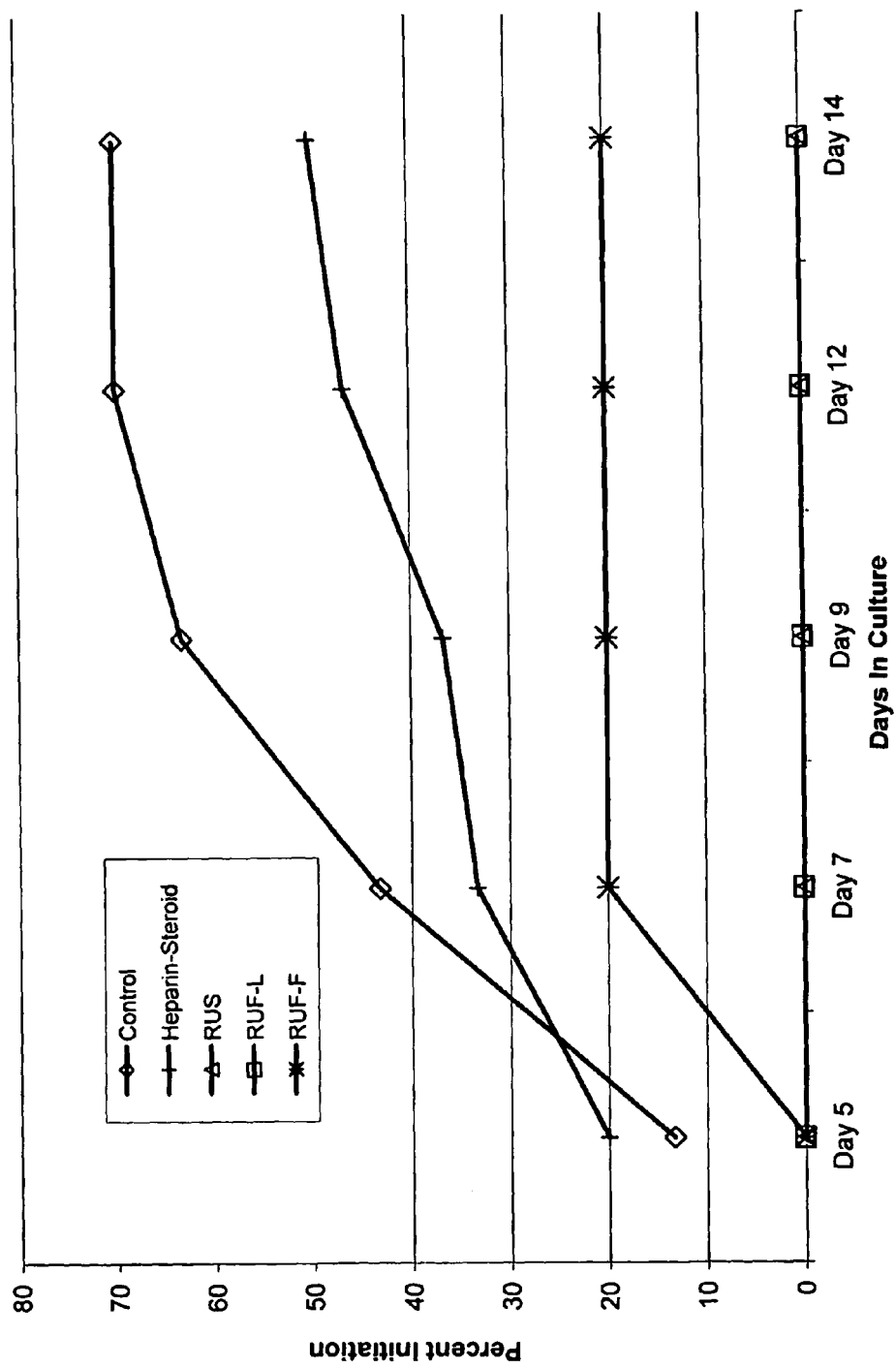
FIG. 11a illustrates the effect of extracts (0.1%) of Chinese blackberry leaves (RUS), blackberry leaves (RUF-L), and blackberry berries (RUF-F) on the initiation of angiogenesis in human placental vein discs.
Figure 11B:
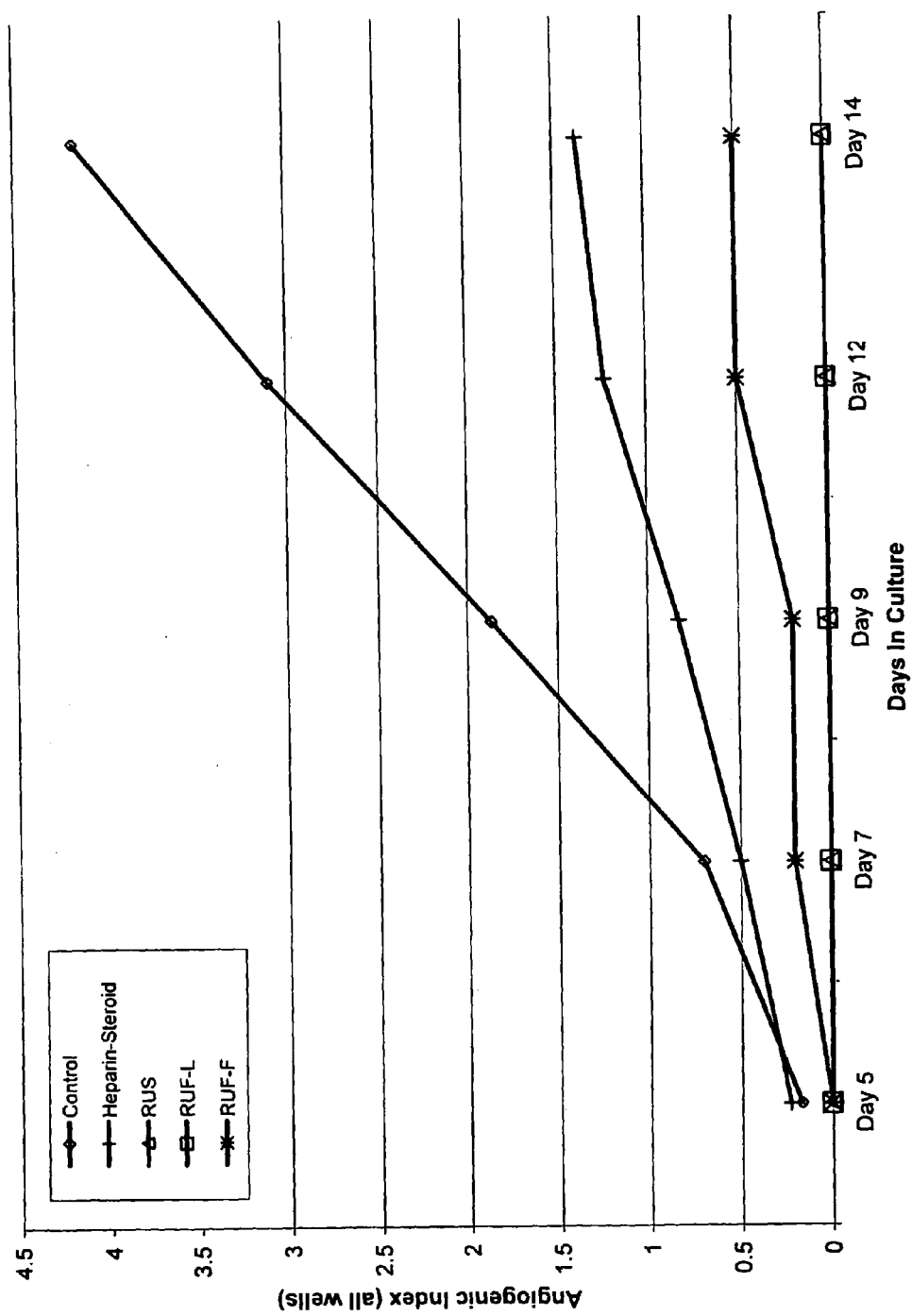
FIG. 11b illustrates the effect of extracts (0.1%) of Chinese blackberry leaves (RUS), blackberry leaves (RUF-L), and blackberry berries (RUF-F) on angiogenesis (both initiation and proliferation) in human placental vein discs as measured by an angiogenic index.
Figure 11C:
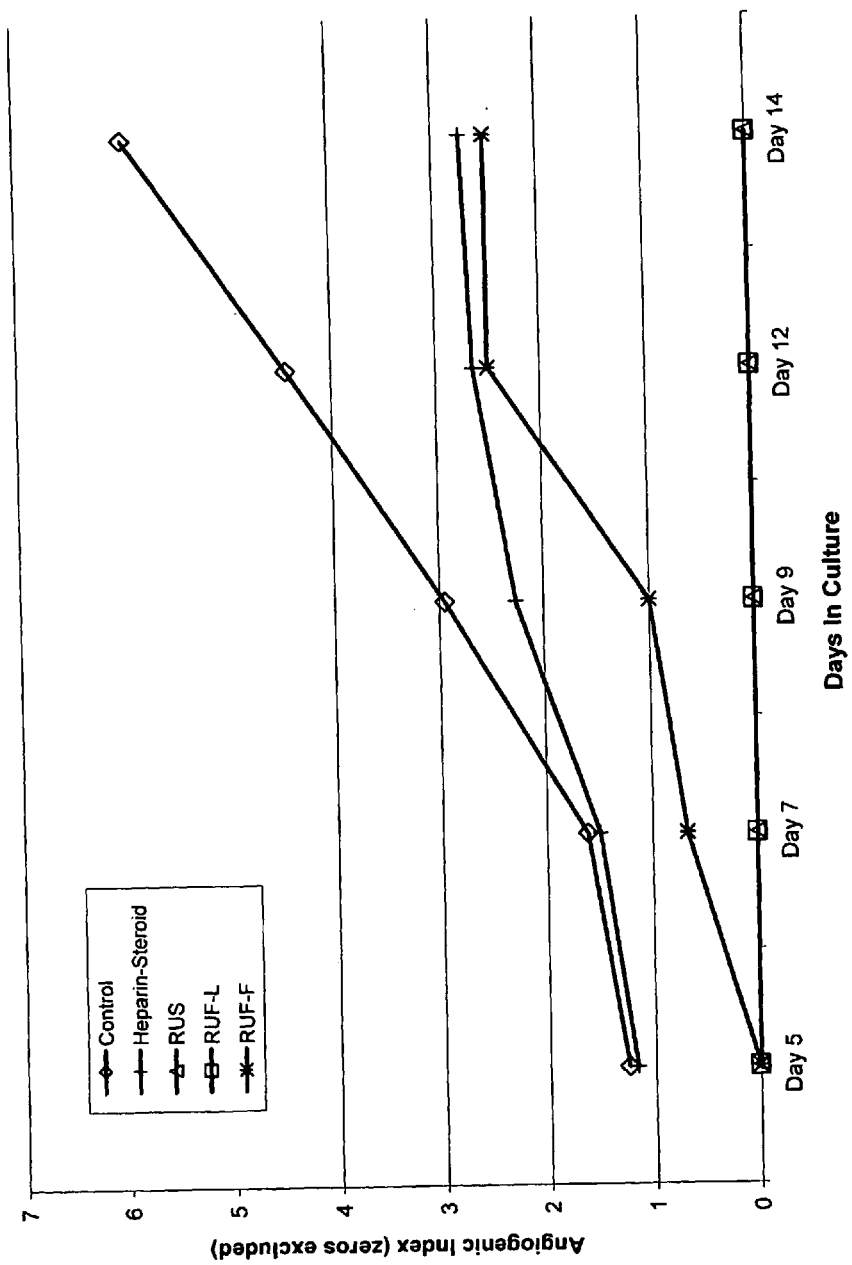
FIG. 11c illustrates the effect of extracts (0.1%) of Chinese blackberry leaves (RUS), blackberry leaves (RUF-L), and blackberry berries (RUF-F) on angiogenesis in human placental vein discs as measured by an angiogenic index after removing discs with a zero angiogenic index (i.e., discs that never initiated an angiogenic response).

As shown in FIG. 11a, RUS (Sweet Leaf Tea) and RUF-L (blackberry leaf) extracts showed 100% inhibition of initiation of angiogenesis during the 14 days of culture and approximately 70% inhibition by the addition of RUF-F (blackberry berry). A similar result was seen when initiation and proliferation are considered together as measured by the mean AI with the zero points added (FIG. 11b), or when only proliferation is considered (FIG. 11c).

This indicates that two of the *Rubus* species showed similar inhibitory effects on human angiogenesis. It is believed that other *Rubus* species will contain gallic acid and other yet-to-be identified active compounds and will show comparable angiogenic activity.

EXAMPLE 18

Effects of Various Gallic Acid Derivatives on Angiogenesis

To test the effects of various gallic acid derivatives on angiogenesis, methyl gallate, propyl gallate, butyl gallate, and octyl gallate were purchased (Sigma Chemical Co., St. Louis, Mo.), and dissolved in Medium 199 (Gibco) to reach a concentration of 0.01% w/v. These concentrations were added to PVDs that had been grown for four days in HPVAM. After addition of the various compounds, the medium was replaced every two to three days, and each well was scored for both initiation of angiogenesis and angiogenic index.

Figure 12A:
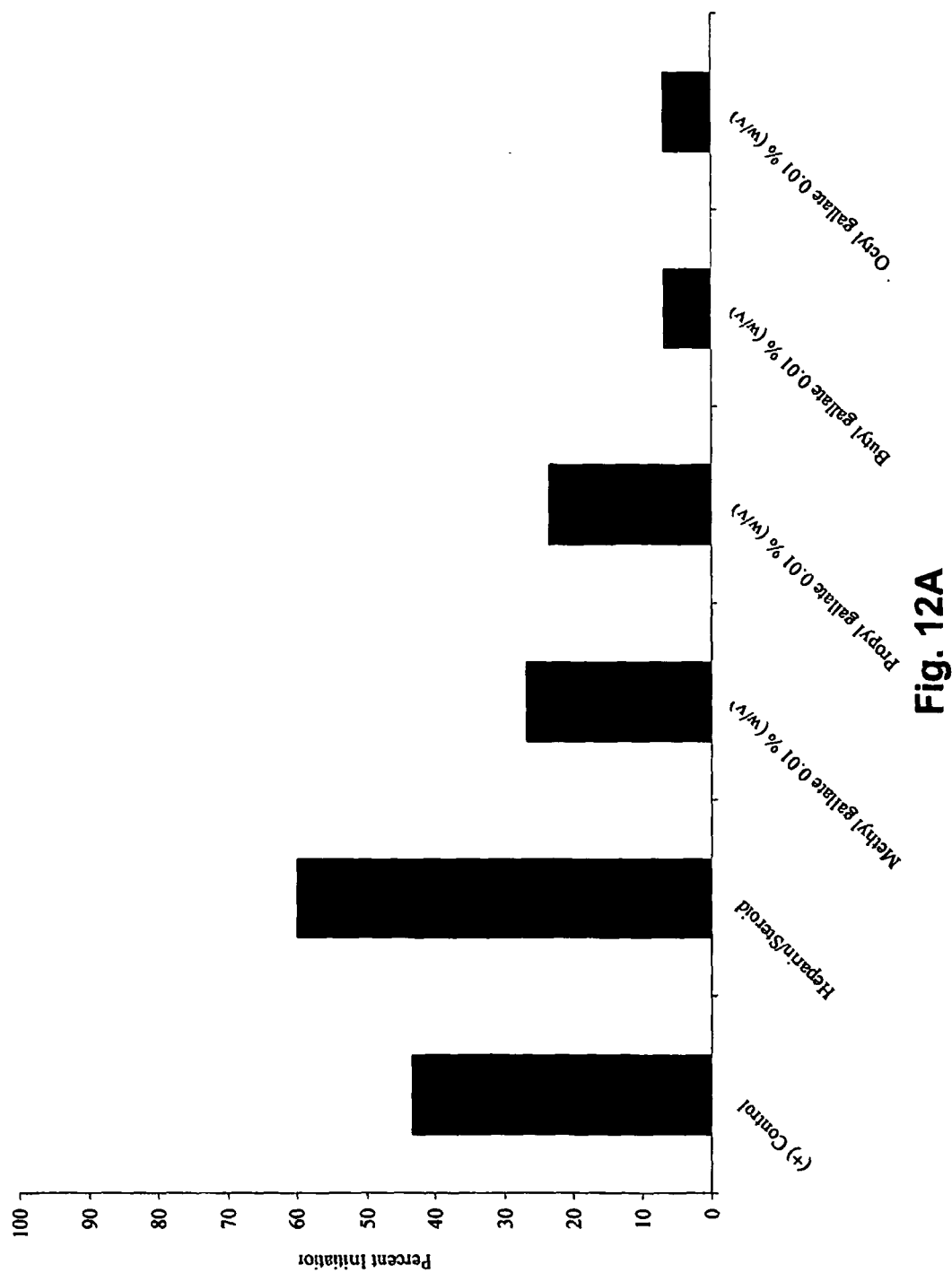
FIG. 12a illustrates the effect of four gallic acid derivatives (0.01% w/w methyl gallate, propyl gallate, butyl gallate, and octyl gallate) on the initiation of angiogenesis in human placental vein discs.

FIG. 12a shows the effects of the four derivatives on angiogenic initiation after 14 days in culture as compared to a control and heparin/steriod as a negative control. Each bar represents the mean of 30 observations. At the concentration of 0.01% w/v, all four derivatives, methyl gallate, propyl gallate, butyl gallate, and octyl gallate, indicated an inhibition of angiogenic initiation when compared to the control of 38%, 46%, 85%, and 85%, respectively.

Figure 12B:
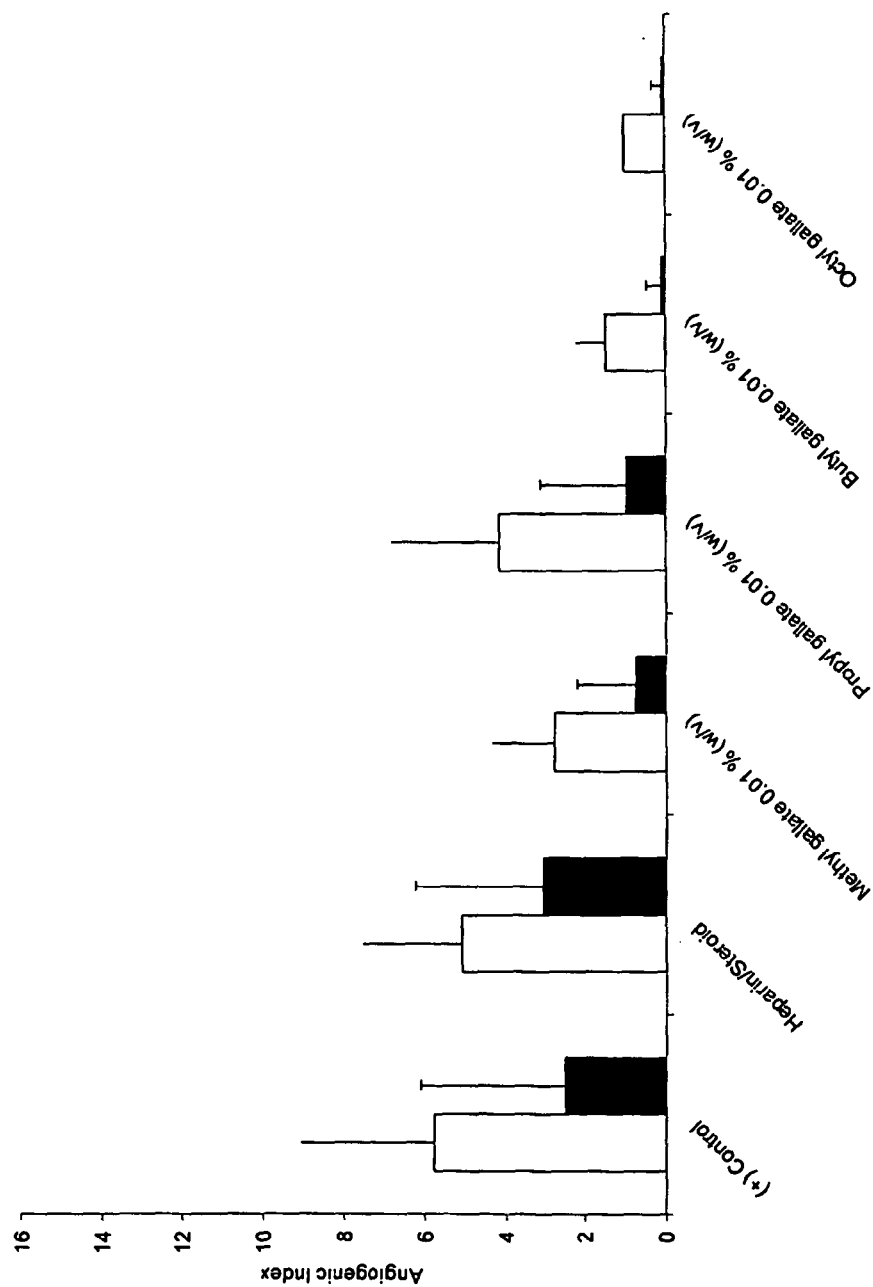
FIG. 12b illustrates the effect of four gallic acid derivatives (0.01% w/w methyl gallate, propyl gallate, butyl gallate, and octyl gallate) on angiogenesis (both initiation and proliferation) in human placental vein discs as measured by an angiogenic index, both with the zero wells and without the zero wells (i.e., wells containing discs that never initiated an angiogenic response).

When initiation and proliferation are considered together, as measured by the mean AI with the zero points included (FIG. 12b), at 0.01% w/v methyl gallate, propyl gallate, butyl gallate, and octyl gallate showed inhibition of angiogenesis when compared with the control of 71%, 61%, 96%, and 97%, respectively. When only proliferation is considered by looking at the mean AI without the zero points (FIG. 12b), at 0.01% w/v methyl gallate, propyl gallate, butyl gallate, and octyl gallate showed inhibition of angiogenic growth when compared with the control of 52%, 28%, 74%, and 83%, respectively.

Figure 13A:
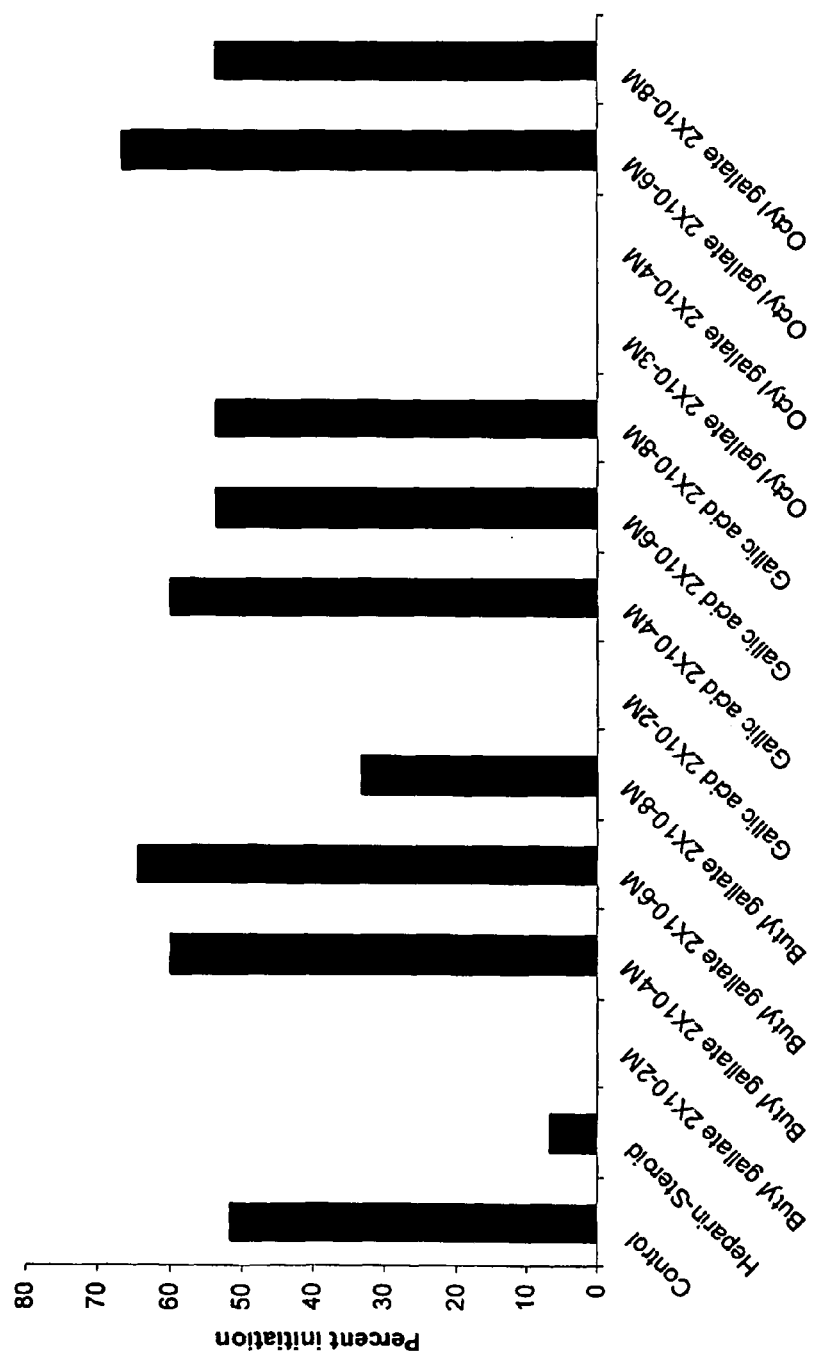
FIG. 13a illustrates the effect of various concentrations ($2 \times 10^{-2}$ M, $2 \times 10^{-4}$ M, $2 \times 10^{-6}$ M, and $2 \times 10^{-8}$ M) of gallic acid, butyl gallate, and octyl gallate on the initiation of angiogenesis in human placental vein discs.
Figure 13B:
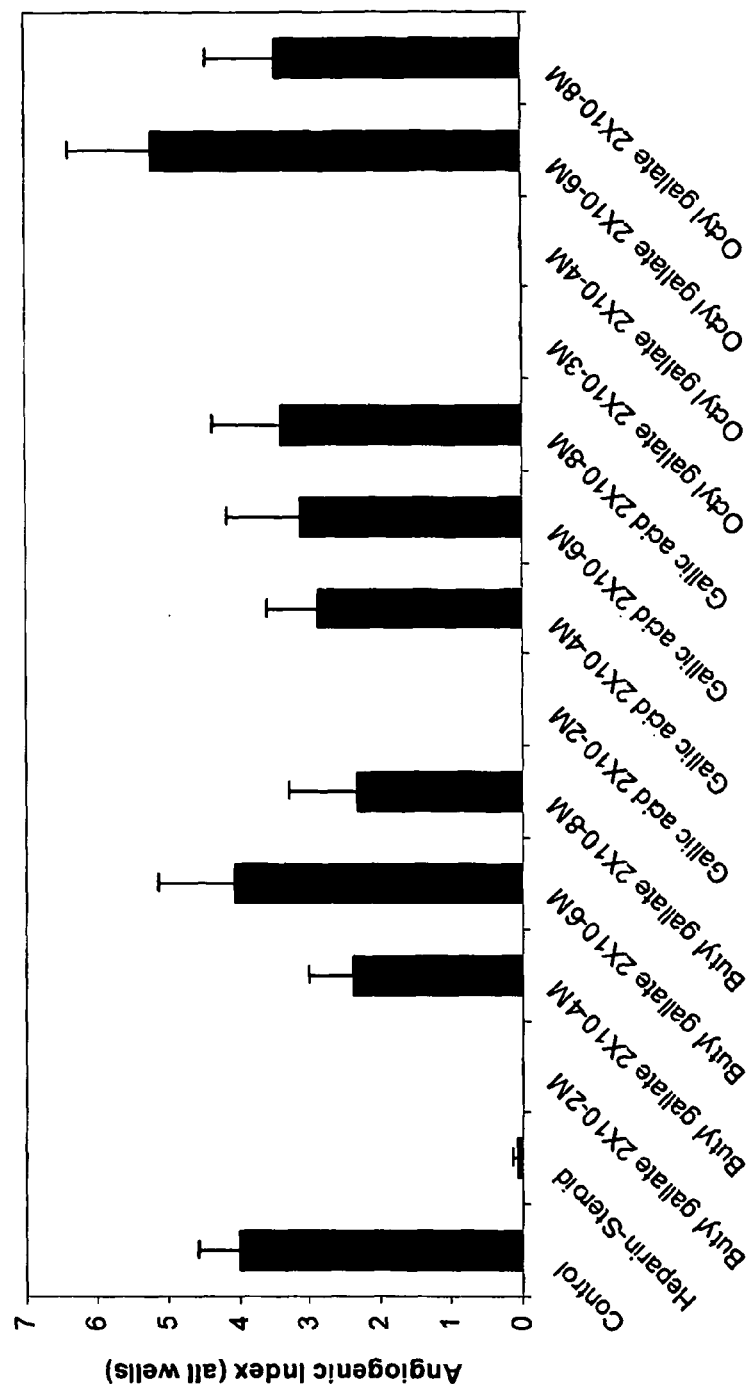
FIG. 13b illustrates the effect of various concentrations ($2 \times 10^{-2}$ M, $2 \times 10^{-4}$ M, $2 \times 10^{-6}$ M, and $2 \times 10^{-8}$ M) of gallic acid, butyl gallate, and octyl gallate on angiogenesis (both initiation and proliferation) in human placental vein discs as measured by an angiogenic index.

Various concentrations of two derivatives, butyl gallate and octyl gallate, and gallic acid were compared as to efficacy of inhibiting angiogenesis, as compared to a positive control and a negative control (heparin/steroid at a concentration of 300/350 ug/ml) as described above. Concentration of methyl gallate and gallic acid were $2 \times 10^{-2}$ M, $2 \times 10^{-2}$ M, $2 \times 10^{-6}$ M, and $2 \times 10^{-8}$ M, and of octyl gallate, $2 \times 10^{-3}$ M, $2 \times 10^{-2}$ M, $2 \times 10^{-6}$ M, and $2 \times 10^{-8}$ M. FIG. 13a indicates that all three compounds totally blocked the initiation of angiogenesis at the highest concentration. Octyl gallate also totally blocked angiogenesis initiation at a concentration of $2 \times 10^{-4}$ M. Each data point in FIGS. 13a and 13b is the mean of fifteen observations.

Figure 13C:
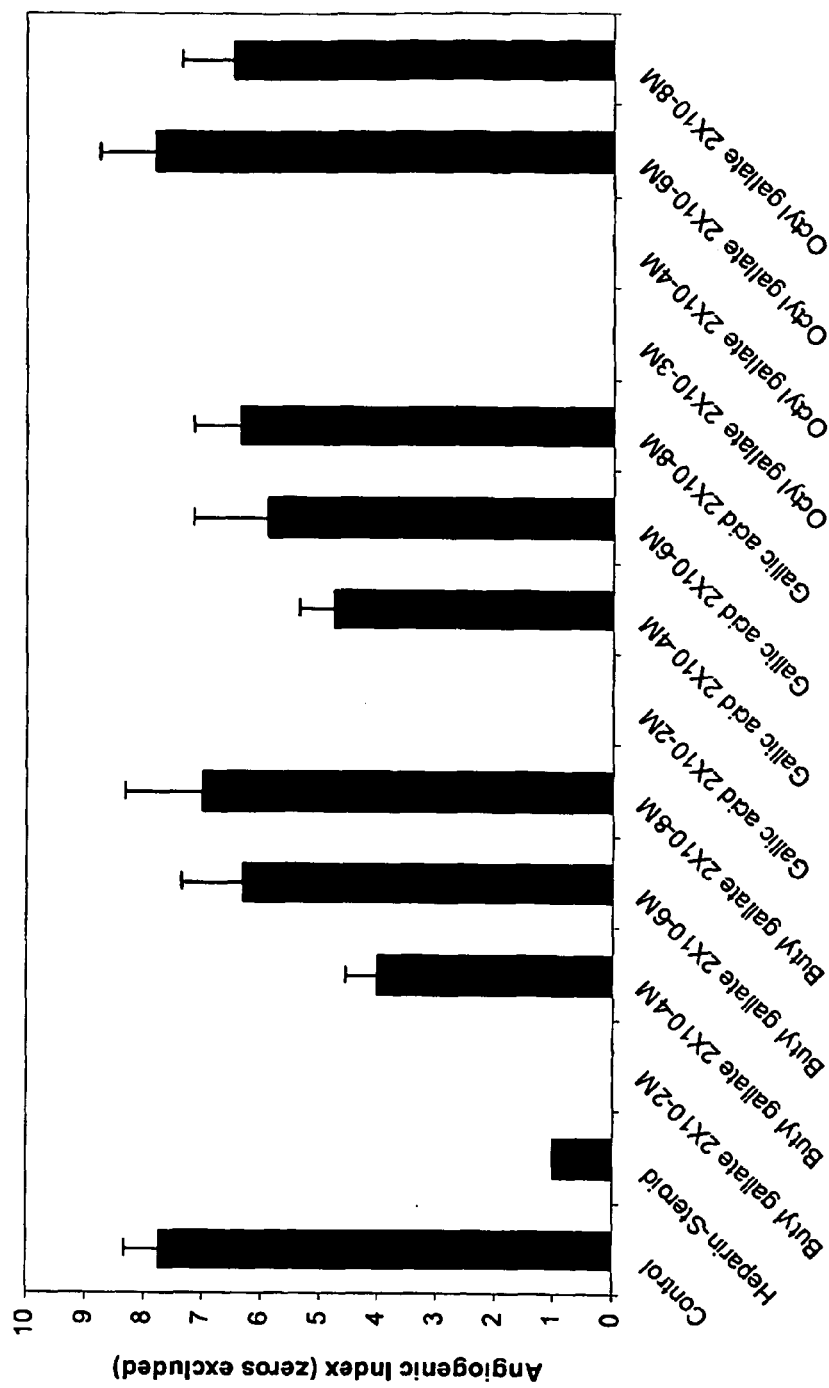
FIG. 13c illustrates the effect of various concentrations ($2 \times 10^{2}$ M, $2 \times 10^{-4}$ M, $2 \times 10^{-6}$ M, and $2 \times 10^{-8}$ M) of gallic acid, butyl gallate, and octyl gallate on angiogenesis in human placental vein discs as measured by an angiogenic index after removing discs with a zero angiogenic index (i.e., discs that never initiated an angiogenic response).

When initiation and proliferation are considered together, as measured by the mean AI with the zero points included (FIG. 13b), all three again totally blocked angiogenesis at the highest concentration, and octyl gallate was effective at $2 \times 10^{-4}$ M. When only proliferation is considered by looking at the mean AI without the zero points (FIG. 13b), the results were the same as above. In FIG. 13c, each data point is the mean of 2 to 10 observations.

These results indicate that derivatives of gallic acid are effective in inhibiting angiogenesis. Of the four derivatives tested, octyl gallate proved to be the most effective, indicating inhibition at concentrations as low as $2 \times 10^{-4}$ M.

EXAMPLE 19

Figure 14:
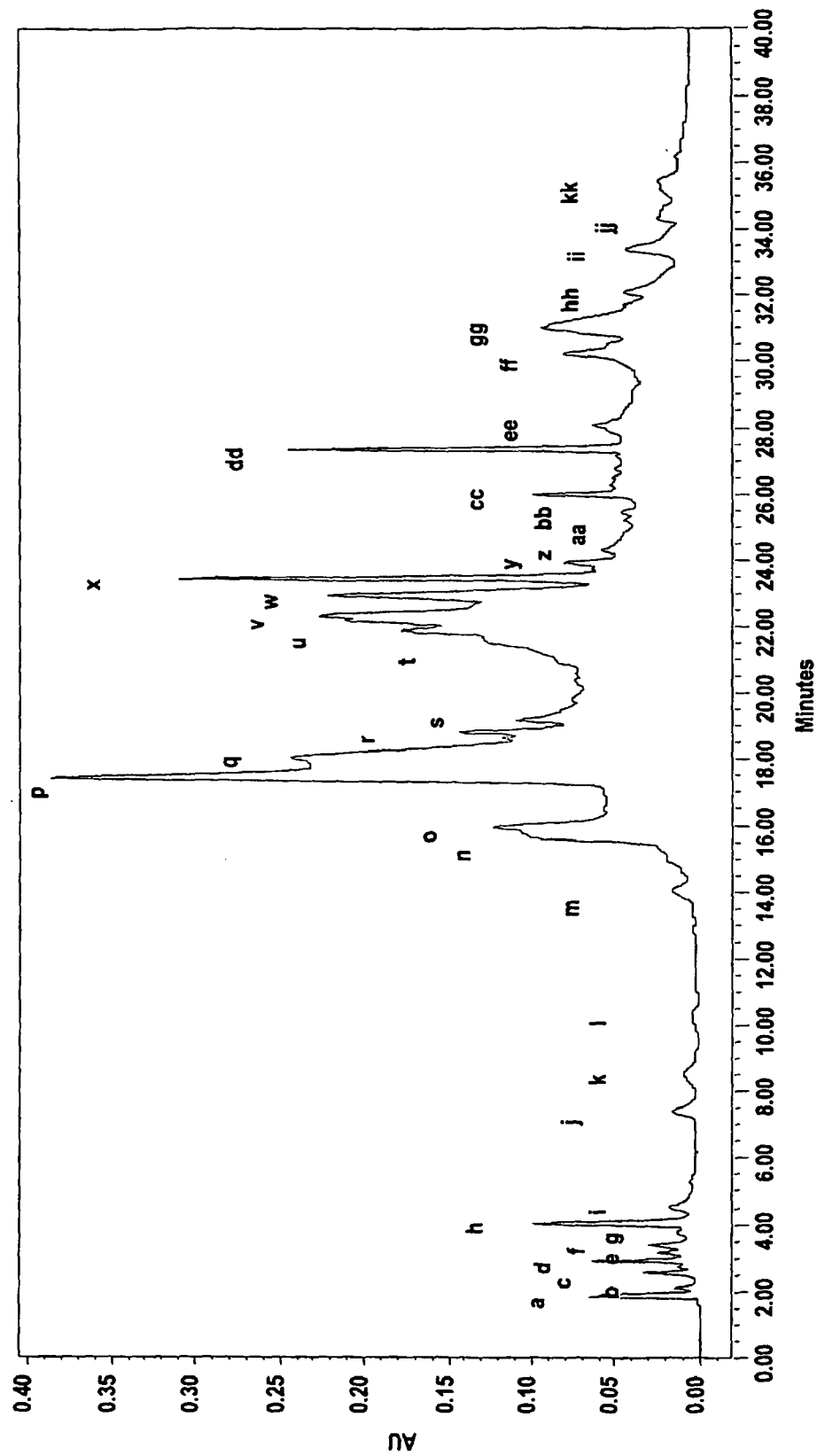
FIG. 14 illustrates a chromatogram of black raspberry crude extract (RUO-C) developed using high performance liquid chromatography at 254 nm.

Angiogenesis Inhibition by *Rubus occidentalis* (Black Raspberry) Berry Extract and Isolated Fraction Frozen whole black raspberries (*Rubus occidentalis*) were purchased from a grower in Oregon. The berries (908 gm) and deionized water at 1:15 w/v ratio were brought to boil in a heating mantle for 120 min, for a crude extraction and pasteurization of the material. The liquid extract was separated from the solids (structural components consisting mostly of fibers and other non-water extractables) by first centrifugal force with an Allegra™ 6KR Centrifuge (Beckman Coulter, Palo Alto Calif.) and then by a filtration system consisting of 20 µm, 1 µm, and 0.45 µm filter units in sequence (Ultrafilter International, Haan Germany). The filtered liquid extract was then concentrated in a 20-L capacity rotary evaporator (Buchi Rotavapor R-220, Flawi, Switzerland) and subsequently freeze-dried (Labconco CO., Kansas City Mo.) to a powder. The crude extract RUO-C powder was 15% w/w of the frozen whole berries, and was fingerprinted by a HPLC chromatogram shown in FIG. 14. Chromatogram of the extract was developed on a HPLC system (Waters Delta 600, Waters Co., Milford, Mass.) at a wavelength of 254 nm consisting of a solvent delivery pump unit, an autosampler (Waters 717 plus), a UV-Vis diode array detector (Waters 2996 Photodiode Array Detector, 190 to 800 nm), and an evaporative light-scattering detector (Waters 2420 ELSD). The system was computer controlled and analyzed with the Empower software. The mobile phase consisted of HPLC-grade methanol and HPLC-grade acetic acidic (0.15%) water and was run in isocratic elution at 5:95 (MeOH:$H_2O$) for the first 12 minutes, followed by a gradient elution to 100:0 for 14 minutes, a cleaning process for 4 minutes, and equilibrium to 5:95 for 15 minutes before a new sample was injected. As shown in FIG. 14, the black raspberry crude extract (RUO-C) is a complex chemical composition of about 39 major components.

The crude extract RUO-C was reconstituted with deionized water in 1:15 w/v ratio. The reconstituted aqueous extract was loaded to a glass column (AceGlass, Vineland N.J.) containing 15 kg of polymer adsorbent resin (a polystyrene resin with a pore size of 46 Å; Dowex® Optipore® V493; Supelco, Inc.; Bellefonte, Pa.). This is a molecular sieve-based separation. The column was first equilibrated with ethanol doing the cleaning (elution), and then with water flushing. After loading of the liquid RUO-C sample, four fractions were eluted with a gradient of 95% ethanol, RUO-00 (0% ethanol), RUO-20 (1 to 20% ethanol), RUO-50 (21 to 50% ethanol), and RUO-95 (51 to 95% ethanol). These four extracts were then evaporated to remove ethanol and subsequently freeze-dried to a powder.

Figure 15A:
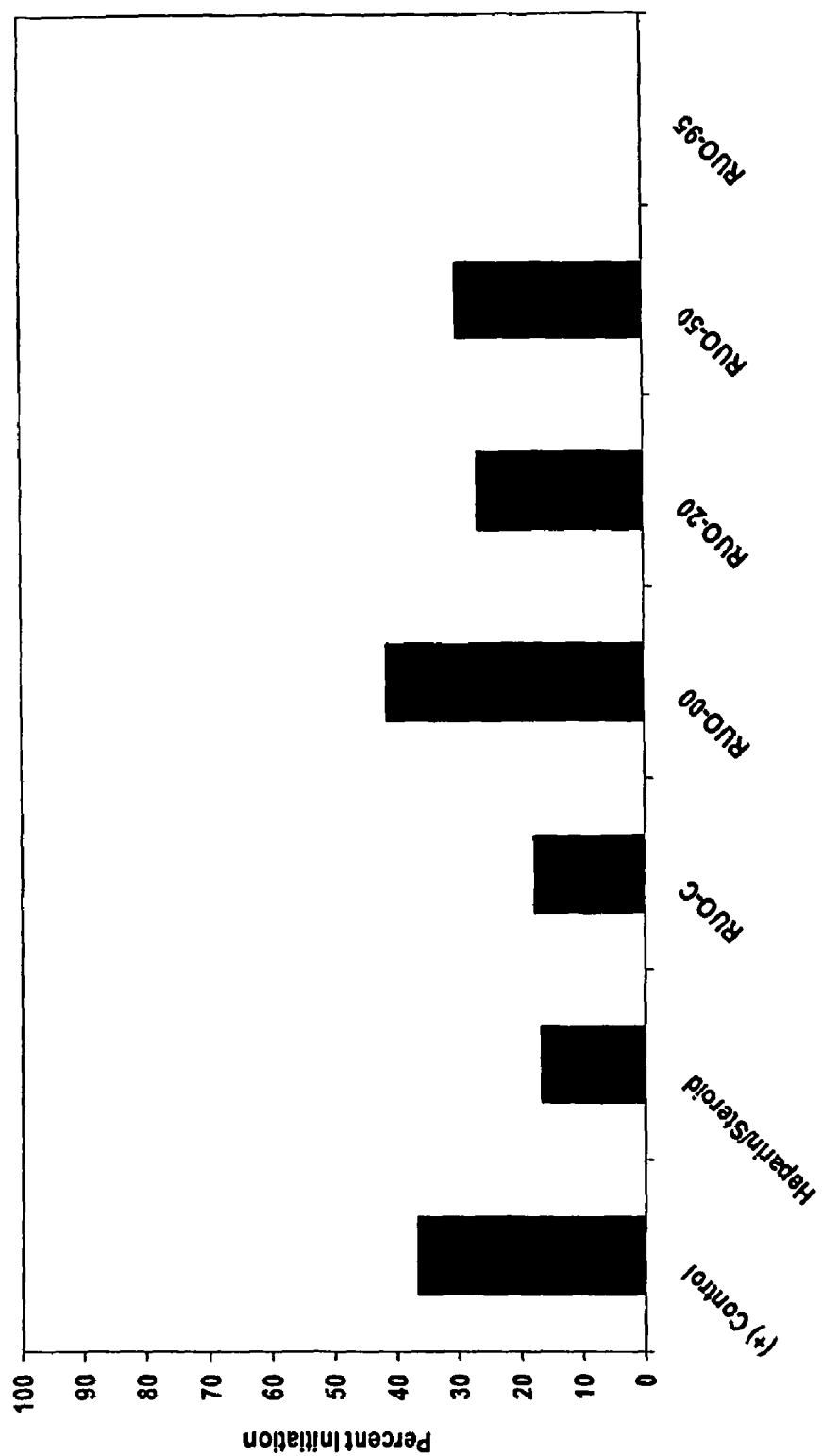
FIG. 15a illustrates the effect of black raspberry berry crude extract (RUO-C) and fractions of RUO-C (RUO-00, RUO-20, RUO-50, and RUO-95), all at 0.01% w/v concentration, on the initiation of angiogenesis in human placental vein discs.
Figure 15B:
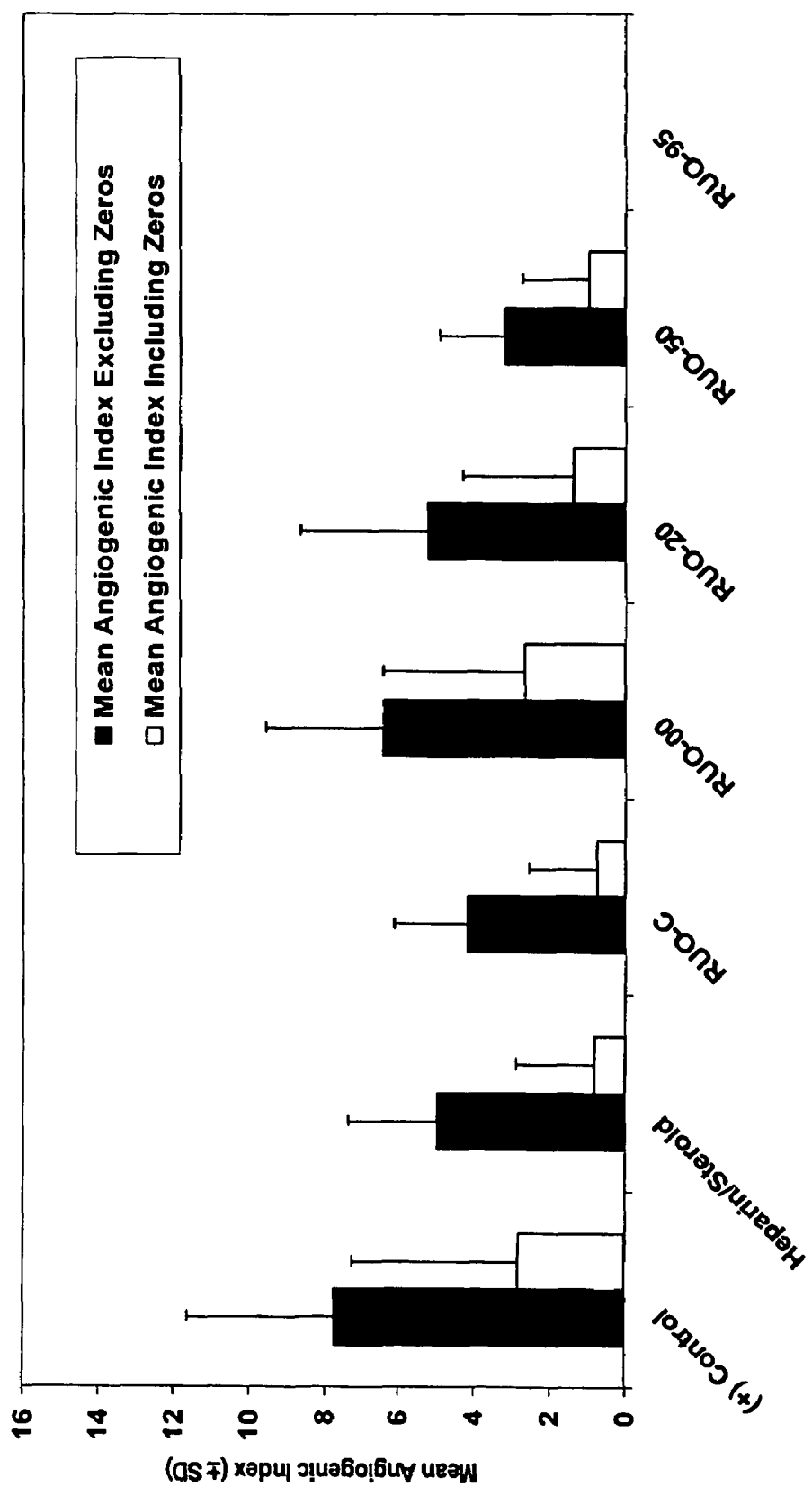
FIG. 15b illustrates the effect of black raspberry berry crude extract (RUO-C) and fractions of RUO-C (RUO-00, RUO-20, RUO-50, and RUO-95), all at 0.01% w/v concentration, on angiogenesis (both initiation and proliferation) in human placental vein discs as measured by an angiogenic index, both with the zero wells and without the zero wells (i.e., wells containing discs that never initiated an angiogenic response).

Before co-culturing with human tissues in the angiogenic assay, the frozen powders were brought to room temperature, reconstituted with HPVAM, and then sterilized with 0.2 μm filters under a sterile hood. The sterile extracts were then co-cultured with human placental vein tissues in 96-well plates for 14 days. The results for the four extracts and the crude extracts in the angiogensis assay are shown in FIGS. 15a and 15b. All fractions were tested at 0.1% w/v, and compared to a heparin/steroid (300/350 ug/ml) negative control. As shown in FIGS. 15a and 15b, both RUO-C and its fraction RUO-95 were effective in inhibiting angiogensis initiation and proliferation. The three other fractions, RUO-00, RUO-20, and RUO-50, were less effective. RUO-C was about 51% inhibitory of the control, while RUO-95 was completely inhibitory at the same concentration. Thus the anti-angiogenic components of the crude extract were almost all isolated into the RUO-95 fraction. The RUO-95 fraction was about 6% of the crude extract.

Figure 16A:
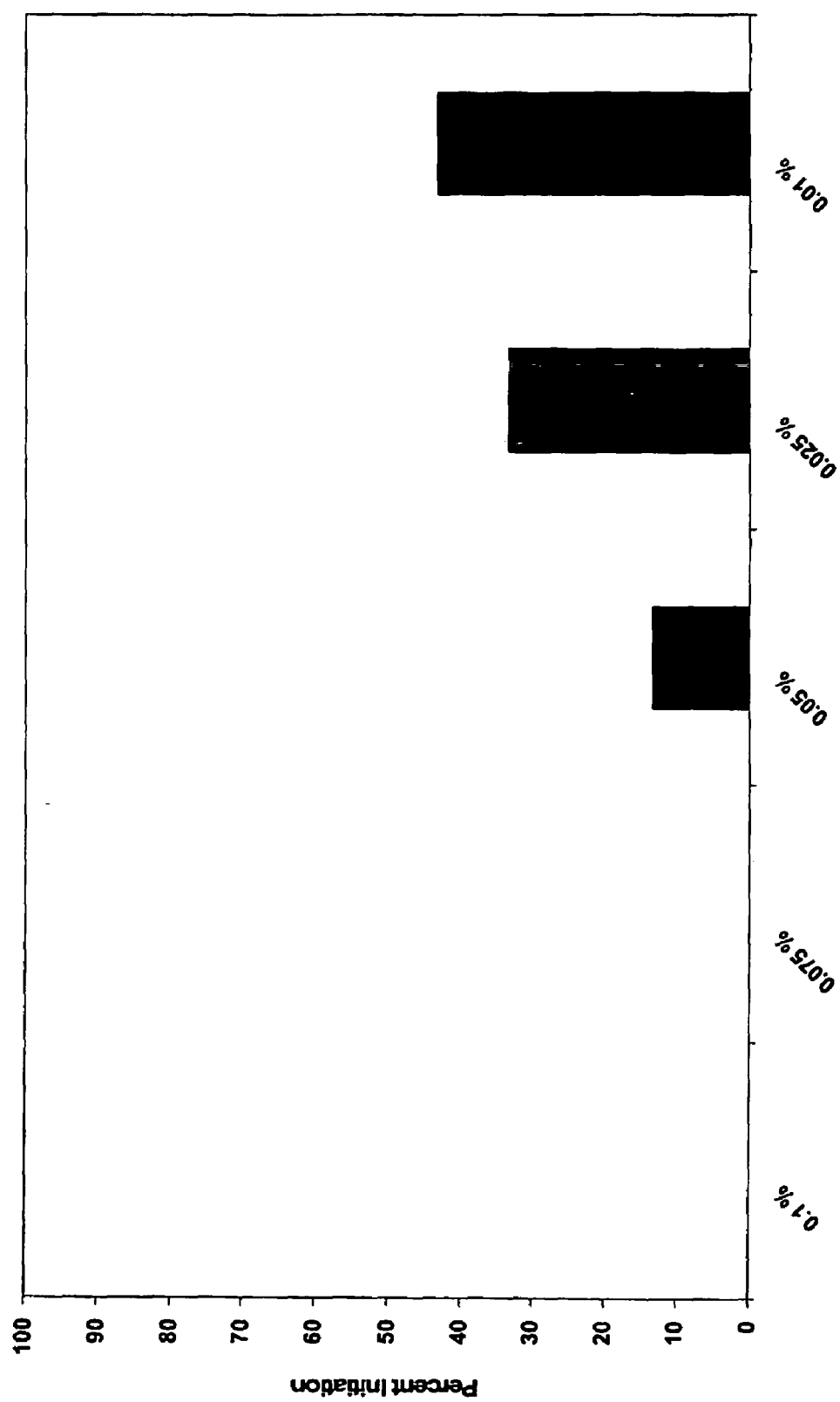
FIG. 16a illustrates the effect of various concentrations (0.1%, 0.075%, 0.05%, 0.025%, 0.01%) of black raspberry berry refined fraction RUO-95 on the initiation of angiogenesis in human placental vein discs.
Figure 16B:
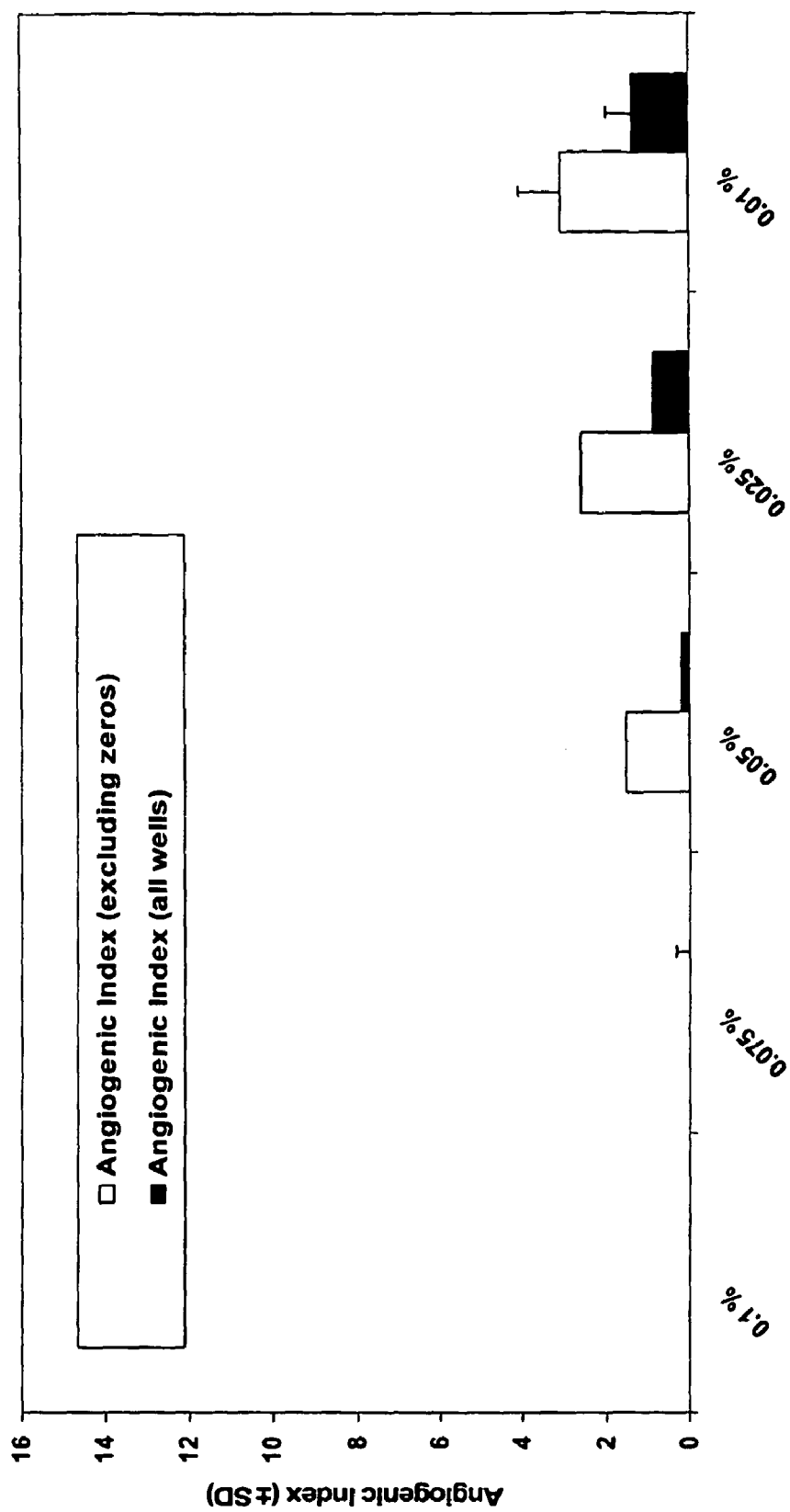

The RUO-95 extract was then assayed in the human tissue based angiogenesis model as described above to test the dose-response activity. The concentrations of RUO-95 used were 0.1% to 0.01%. FIG. 16a shows the dose response of RUO-95 in inhibiting angiogenic initiation. RUO-95 showed a dose-dependent inhibition of angiogenic initiation, and totally inhibited angiogenic initiation at a concentration of 0.075% w/v. FIG. 16b shows the dose response of RUO-95 in inhibiting overall angiogenic proliferation (all wells) and in inhibiting angiogenic vessel growth in wells initiating angiogenesis (without zero wells). Again, total inhibition was seen at 0.075%. This fractionation process resulting in RUO-95 resulted in about a 106-fold concentration of the active angiogenic components in black raspberries. This fraction could be used in therapeutic or other applications.

Figure 17:
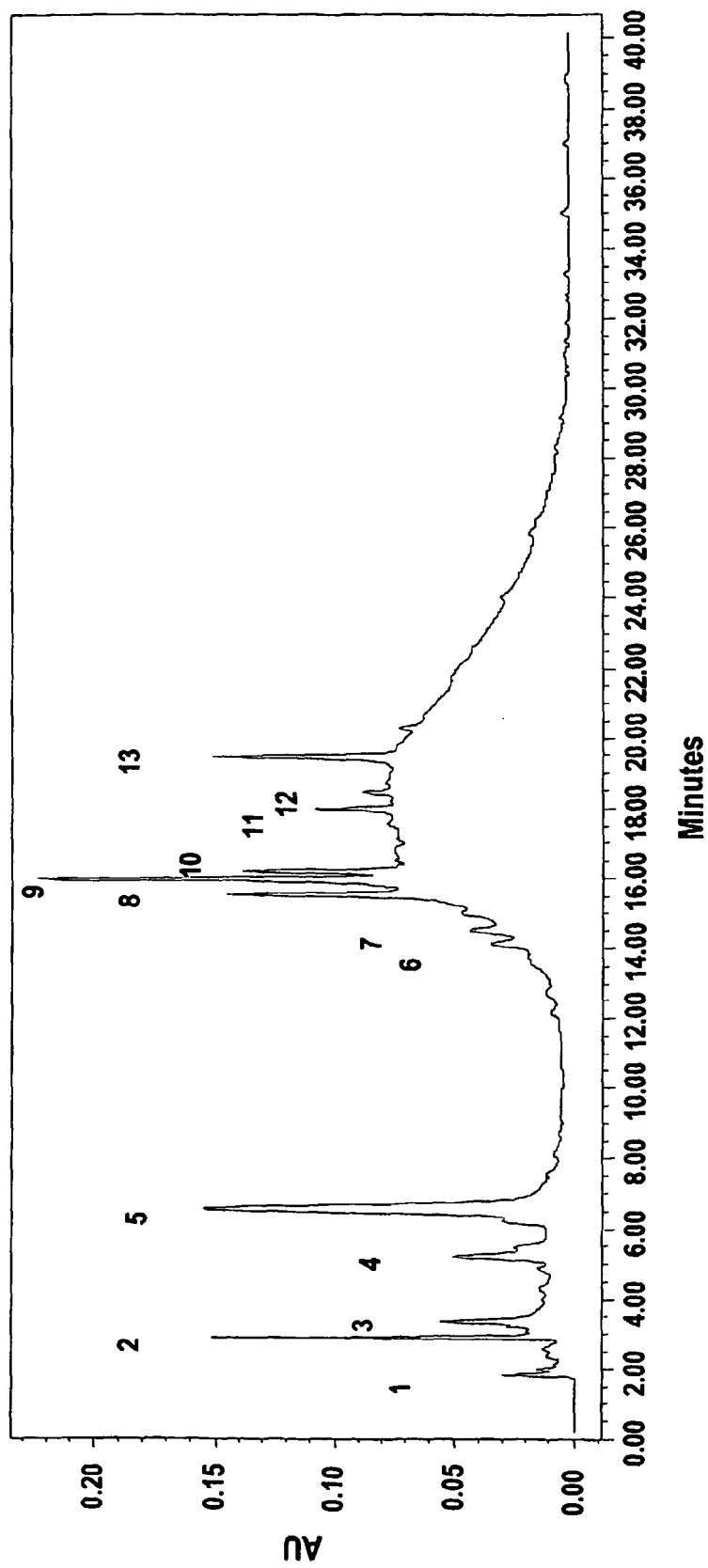
FIG. 17 illustrates a chromatogram of refined black raspberry crude extract (RUO-95) developed using high performance liquid chromatography at 254 nm.
Figure 18:
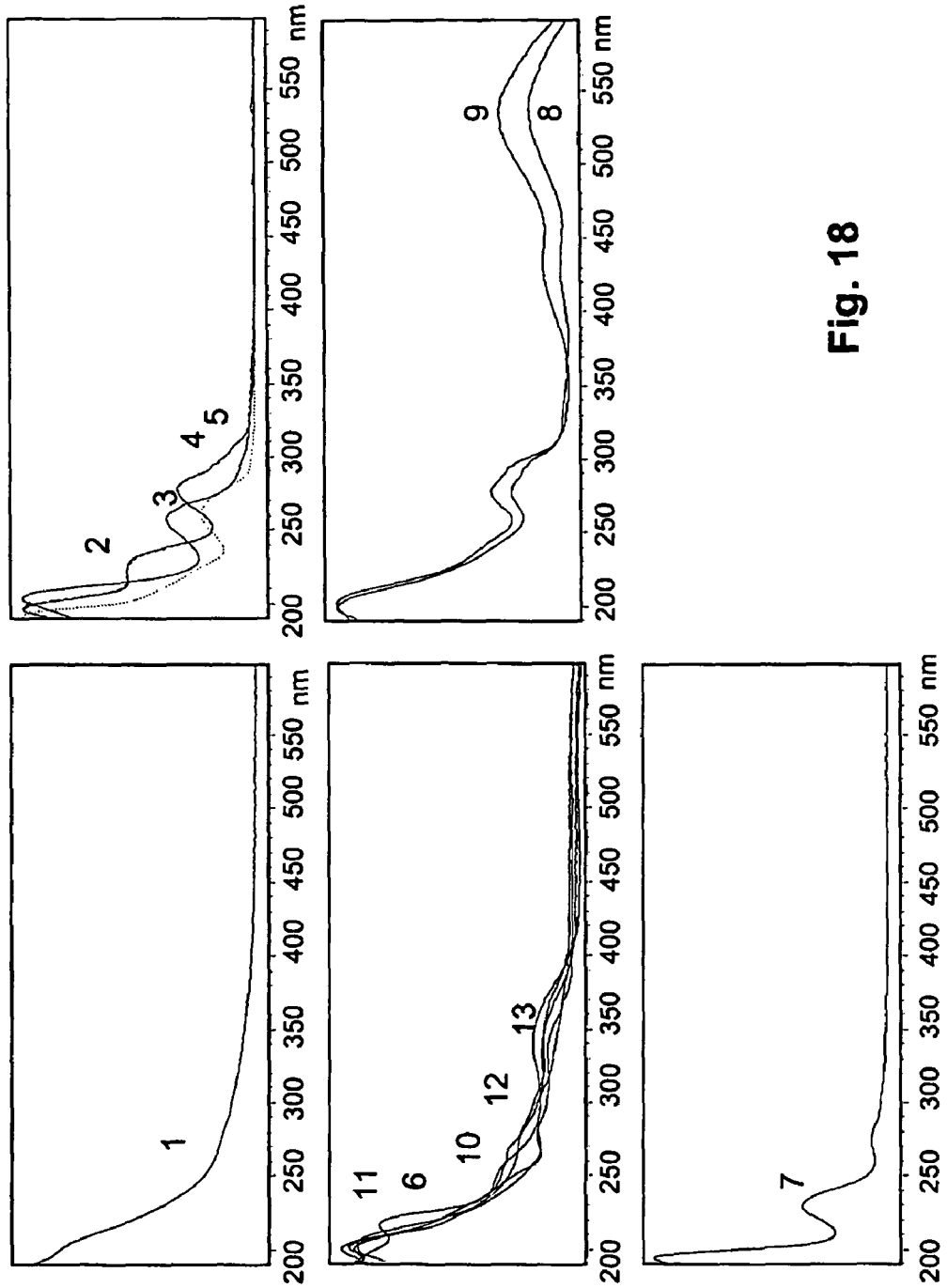
FIG. 18 illustrates the normalized UV absorption spectra of major components identified in the chromatogram of FIG. 17 of the refined black raspberry crude extract (RUO-95).

The RUO-95 fraction was fingerprinted using HPLC as described above for RUO-C. The resulting chromatogram is shown in FIG. 17. FIG. 17 indicates that RUO-95 is a simpler chemical composition than that of RUO-C, consisting of 13 major peaks. Each peak was then further characterized by its retention time and UV absorption spectra as indicated in FIG. 18.

Further quantitative analysis indicated that the refined extract RUO-95 contained about 0.42% w/w gallic acid. Thus one anti-angiogenic compound in RUO-95 is gallic acid. At the $IC_{100}$ dose (total inhibitory concentration) of 0.1% w/v, gallic acid in the refined RUO-95 extract available to the test tissues was about $2.5 \times 10^{-5}$ M. Based on the gallic acid dose response curve (FIGS. 3a, 3b, and 3c), RUO-95 is 40-fold more potent than gallic acid alone. If gallic acid were the only active compound, then its anti-angiogenic activity would have yielded an estimated 19% inhibition ($IC_{19}$) at this concentration of $2.5 \times 10^{-5}$ M. This may be a critically significant display of synergism by compounds in RUO-95. UV absorption spectral analyses on HPLC revealed that 5 major groups of compounds might exist in the active fraction RUO-95 (FIG. 18). Group 1 (Peak 1) might be such compounds with low UV absorption like saponins and terpenoids. Group 2 (Peaks 2, 3, 4, and 5) having peak absorptions around 260 nm might be gallotannins (including gallic acid). Group 3 (Peaks 6, 10, 11, 12, and 13) having weak absorption peaks at 280 nm and 350 nm might be flavonoids. Group 4 (Peaks 8 and 9) featuring absorption peaks at 279 nm, 435 nm, and 536 nm might be anthocyanins. Group 5 (Peak 7) might be aliphatic, double-bonded compounds.

Thus black raspberry crude extract was shown to be an effective anti-angiogenic composition. Moreover, fraction RUO-95 was found to contain almost all of the anti-angiogenic activity, part of which could be due to the presence of gallic acid. However, RUO-95 exhibits anti-angiogenic activity greater than what would be expected from gallic acid. This indicates either the presence of another very active anti-angiogenic compound, or a synergistic effect of several compound in RUO-95. Thus RUO-95 is an active fraction of an aqueous black raspberry extract that contains anti-angiogenic compounds that are small molecules (less than 2000 Daltons), that is more soluble in ethanol in water, that contains gallic acid, and contains one or more other compounds selected from the group consisting of saponins, terpenoids, gallotannins, flavonoids, anthocyanins, and double-bonded, aliphatic compounds. RUO-95 shows an HPLC chemical profile as shown in FIG. 17.

EXAMPLE 20

Cytotoxicity of Refined Black Raspberry Extract RUO-95

To test the toxicity of the refined RUO-95 extract, tissue viability after co-culture with RUO-95 will be monitored to ensure that inhibition of human angiogenesis is not through apoptosis or cytotoxicity.

Following a 14-day assay, embedded tissues will be tested for viability as an indication of cytotoxicity levels at various concentrations of RUO-95 from about 1% to about 0.0001%. The spent media will be aspirated, and the first 10 wells of each group will be treated with dye solution media [68% M199 (Gibco), 17% FBS, and 15% MTT dye solution (Promega)]. The tissues will be incubated for 48 hr at 37° C. and 5% $CO_2$. The wells will then be observed microscopically under low power to determine if the MTT has been metabolized to the characteristic blue color to indicate tissue viability.

It is expected that RUO-95 at these concentrations will be non-toxic to cells. The nutritional ingredients found in these berry extracts are generally non-toxic compared to herbal preparations. This may be especially true when the berry fraction is still an extract rather than a single chemical entity.

EXAMPLE 21

Absorption of Orally Administered Refined Black Raspberry Extract RUO-95

To demonstrate that a refined black raspberry extract is orally active, the anti-angiogenic activity of serum collected after oral administration by gavage of RUO-95 to rats will be assayed in the HPVAM model as described above in Example 13. For each experiment, 30 300-gram male Sprague Dawley rats will be used. Each will be housed individually and fed rat chow ad libitum. After arrival, rats will spend one week in quarantine before transfer into the experimental animal room. One group (n=5) of rats will serve as control and receive only water vehicle. All other rats will be divided into five groups to receive either one of four different doses of the extract by oral gavage in water vehicle or the lowest of the oral doses by intraperitoneal injection in a 0.9% saline vehicle (n=5 per group) daily for three consecutive days. The oral doses used will provide a 5-fold range of the extracts.

All extracts will be vortexed and passed through a 0.2 μm filter before suspension in sterile water or saline. At the end of the treatments, all rats will be anesthetized with nembutal and killed by a guillotine for collection of trunk blood for the preparation of serum. This serum will be stored at −70° C. until used in the assay procedures. This serum will be tested in a 50%-50% mixture with FBS as the serum source in the HPVAM assay, i.e. 5% FBS plus 5% rat serum for a total 10% serum for the assay.

It is expected that the serum from the gavaged rats will inhibit angiogenesis in the human placental tissue angiogenesis assay. By using multiple doses, the required levels for optimal activity will be determined. Comparison with an intraperitoneal administration of the extract will provide information on the absorption of the active components in the extracts and indicate whether a higher dose is needed in an oral form to be active.

It has been shown anti-angiogenically-conditioned rat serum does not have to be $IC_{100}$ in the in vitro HPVAM assay in order to produce an in vivo effect on stopping tumor growth of tumor bearing rats (data shown in FIG. 9 and FIG. 10; and described in Examples 13 and 14). If the anti-angiogenic inhibition activity in the serum is too low to be detected in the HPVAM assay, either the serum volume in the assay (up to a maximum 40% concentration) will be increased, or the serum collected will be concentrated by freeze-drying the serum and then reconstituting in a reduced volume.

EXAMPLE 22

Efficacy of Orally Administered Black Raspberry Extract RUO-95 Against Tumors

To test the efficacy of RUO-95 against tumors, a cancer model (CA20948 pancreatic tumor; Erasmus University, Rotterdam, Netherlands) will be used, and injected into young male Lewis rats. The rats will be divided into two groups: rats given water/standard chow, and rats given standard chow and daily gavage with low, intermediate or high dose extract (actual doses to be determined based on the outcomes of Example 21). Body weight and tumor area will be measured three times a week. Necropsies will be performed at the end of the experiment to determine the incidence and conglomerate size of the tumor and any lung metastasis.

It is expected that a dose of RUO-95 will be found that will stop or slow cancer from growing.

EXAMPLE 23

Angiogenesis Inhibition by *Punica granatum* L. (Pomegranate) Fruit Extract and Isolated Fraction Whole Pomegranate Fruit Extraction Fresh fruits of pomegranate (*Punica granatum* L. family Punicaceae, the Wonderful cultivar) were purchased from a pomegranate orchard of the Simonian Fruit Company in Fowler, Calif. The fresh fruits were surface-cleaned, cut into halves, and manually crushed into pieces in a stainless steel professional juice maker. The whole fruit pieces and juice were then extracted in deionized water at 1:15 w/v ratio, and the liquid was brought to boil for 30 min in a heating mantle to achieve pasteurization. The liquid extract was separated from the solids (structural components consisting mostly of fibers, cellulose, semi-cellulose, debris of cells), centrifuged in an Allegra™ 6KR Centrifuge (Beckman Coulter, Palo Alto, Calif.), and then filtered in a system consisting of 20 μm, 1 μm, and 0.45 μm filter units in sequence (Ultrafilter International, Haan, Germany). The filtered liquid extract was concentrated in a 20-L capacity rotary evaporator (Buchi Rotavapor R-220, Flawi, Switzerland) and subsequently freeze-dried (Labconco Co., Kansas City, Mo.) to give a crude extract powder ("PUG-C"). The PUG-C powder was placed in a sealed container and stored frozen before fractionation and assays. The crude extract PUG-C accounted for 20% of the fresh pomegranate fruit weight, and was mostly water-soluble.

Fractionation of Crude Pomegranate Extract

The crude extract PUG-C powder was reconstituted with deionized water in 1:15 w/v ratio, and then fractionated by column chromatography based on molecular size separation. The reconstituted aqueous extract was loaded on a glass column (AceGlass, Vineland, N.J.) containing polymer adsorbent resin (a polystyrene resin with a pore size of 46 Å; Dowex® Optipore® V493; Supelco, Inc.; Bellefonte, Pa.). The column was first equilibrated with ethanol for cleaning (elution), then was flushed with water. After loading the reconstituted PUG-C sample, three fractions (PUG00 (0% ethanol), PUG50 (1 to 50% ethanol), and PUG100 (51 to 95% ethanol)) were eluted with 95% ethanol. All three fractions were evaporated to remove organic solvent and subsequently freeze-dried to a powder.

Anti-Angiogenic Activity of PUG-C and Its Three Fractions

Before co-culturing with human tissues, the frozen extract or fraction powder was brought to room temperature and reconstituted with distilled, deionized water. The reconstituted liquid extract was sterilized with 0.2 μm filters under a sterile hood before the angiogenesis assays. The reconstituted liquid extract was also subjected to a column chromatography separation based on the molecular sieve mechanism. The aqueous pomegranate crude extract and its fractions were then co-cultured with the human placental vein as described above or fat tissue prepared for assaying in 96-well plates.

Figure 19A:
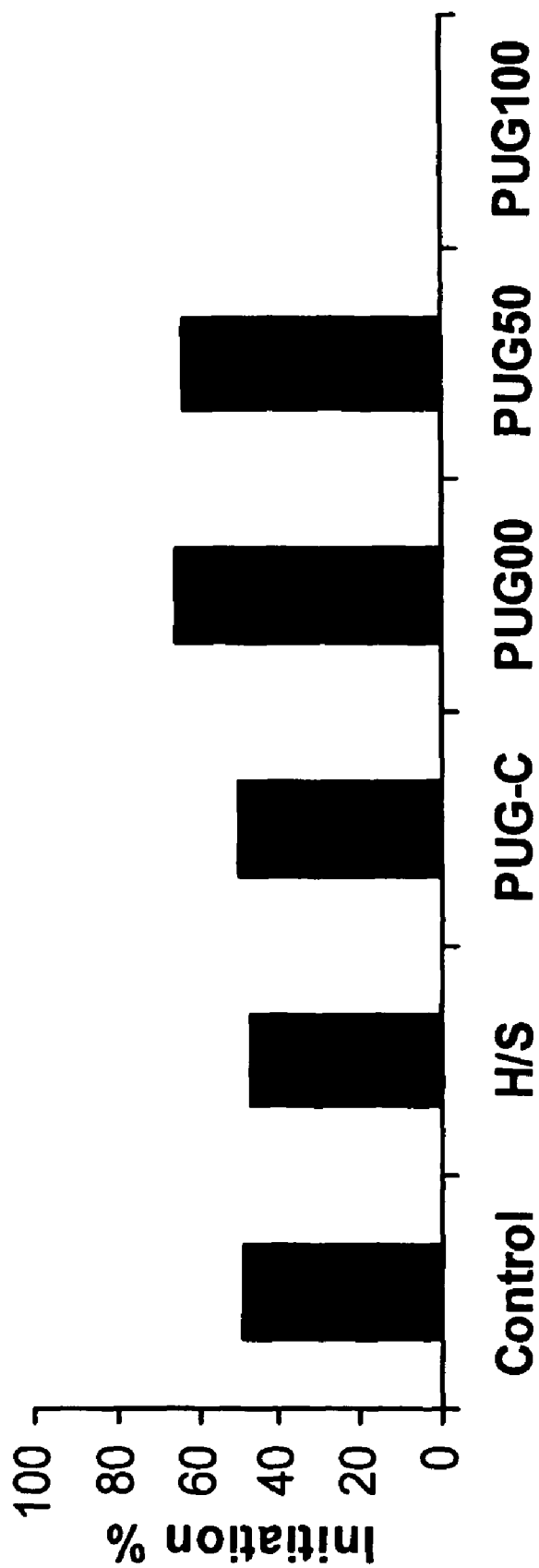
FIG. 19a illustrates the effect of pomegranate fruit crude extract (PUG-C) and its fraction (PUG00, PUG50, and PUG100), all at 0.1% w/w concentration, on the initiation of angiogenesis in human placental vein discs.
Figure 19B:
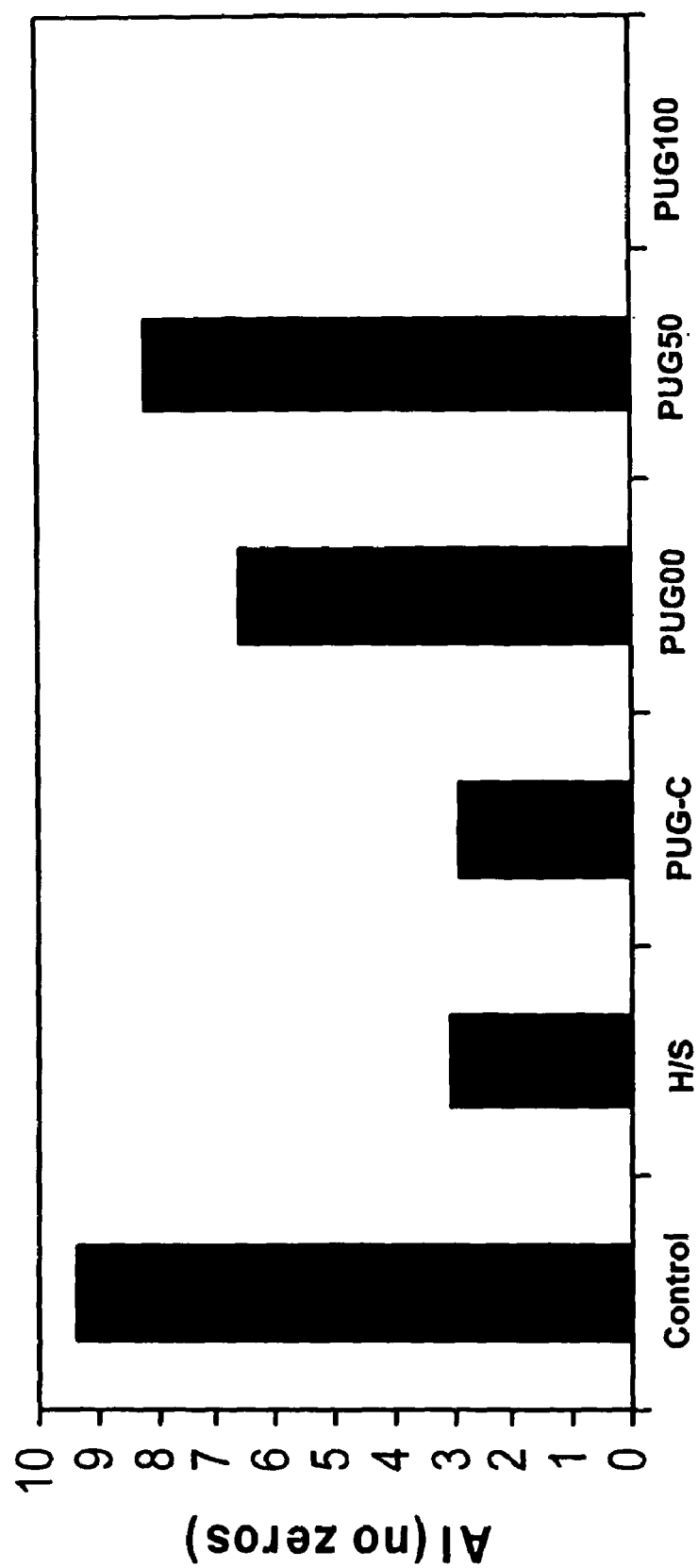
FIG. 19b illustrates the effect of pomegranate fruit crude extract (PUG-C) and its fractions (PUG00, PUG50, and PUG100), all at 0.1% w/w concentration, on angiogenesis in human placental vein discs as measured by an angiogenic index after removing discs with a zero angiogenic index (i.e., discs that never initiated an angiogenic response).
Figure 19C:
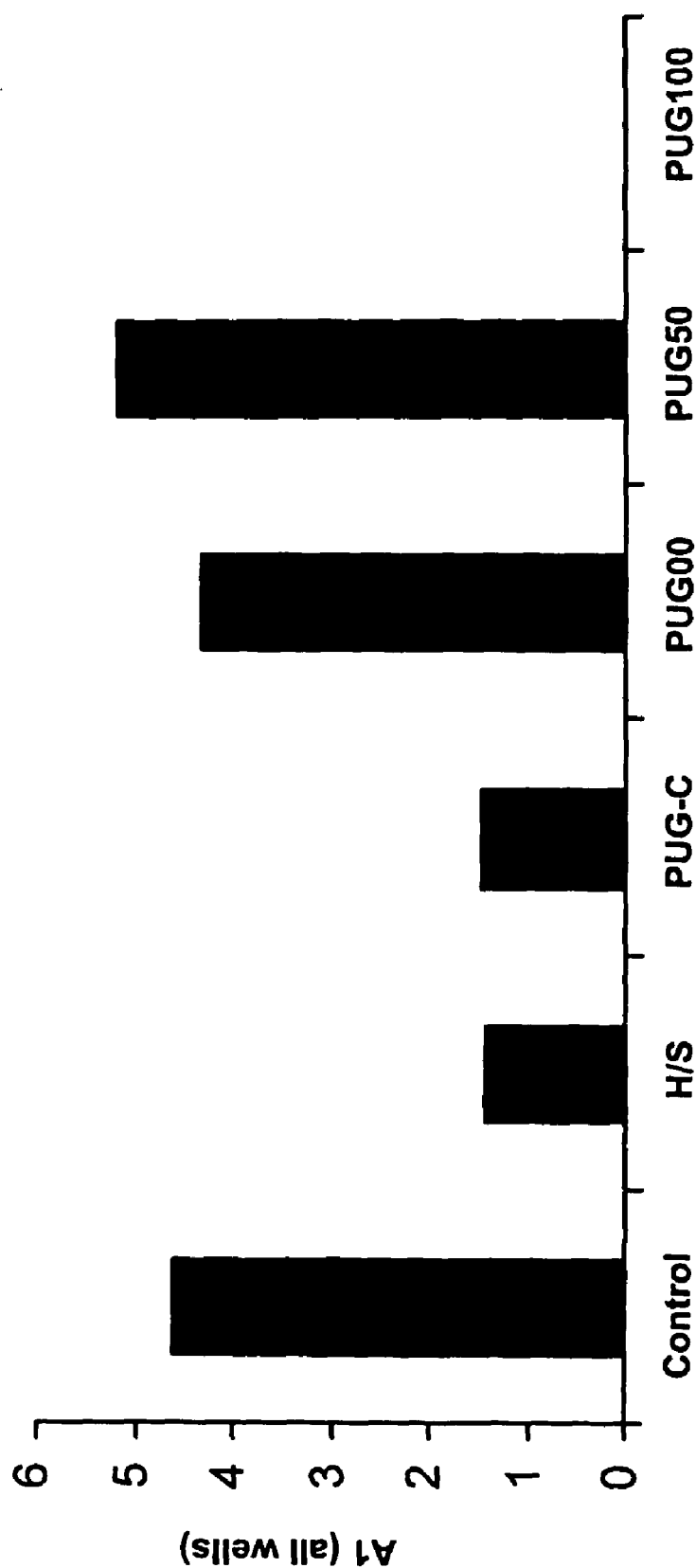
FIG. 19c illustrates the effect of pomegranate fruit crude extract (PUG-C) and its fractions (PUG00, PUG50, and PUG100), all at 0.1% w/w concentration, on angiogenesis (both initiation and proliferation) in human placental vein discs as measured by an angiogenic index.

At 0.1% w/w and after 14 days of co-culture with human placental vein discs, the crude pomegranate extract PUG-C did not affect the human angiogenic initiation compared to the control (FIG. 19a). In fact, fractions PUG00 and PUG50 appeared to be proangiogenic. Only the PUG100 fraction inhibited and completely stopped the angiogenic initiation, preventing the resting blood vessels from developing new blood vessels. Once angiogenic vessels were already present, the crude PUG-C inhibited further angiogenic vessel growth by 70% compared to the promotive control, and similar to the known inhibitory effect of the negative control, Heparin/Steroid H/S (FIG. 19b). Two fractions, PUG00 and PUG50, were not inhibitory compared to the control, suggesting the inhibitory components of the crude PUG-C must have been fractionated into the PUG100 fraction. Overall, the aqueous pomegranate extract PUG-C inhibited angiogenesis by 70% (compared to the control) 0.1% w/v concentration (FIG. 19c). Its fractions PUG00 and PUG50 were not anti-angiogenic or slightly proangiogenic. In contrast, fraction PUG100 completely suppressed human angiogenic initiation and vessel growth at 0.1% w/v concentration.

The above crude extraction resulting in PUG-C removed nearly 80% of the weight from the fresh pomegranate fruit. The removed components were structural components such as fibers, cell walls, cell debris, and other non-water extractables. By fractionation followed by the angiogenic assay, the inactive components, PUG00 and PUG50, were identified and removed. This resulted in a highly refined anti-angiogenic fraction PUG100. PUG100 accounted for 22% of the crude extract PUG-C. Thus this anti-angiogenic fraction was 4% w/w of the fresh pomegranate fruits. This fractionation process achieved a 25-fold concentration of the anti-angiogenic components.

Anti-Angiogenic Activity of Subfractions of PUG100

Figure 20A:
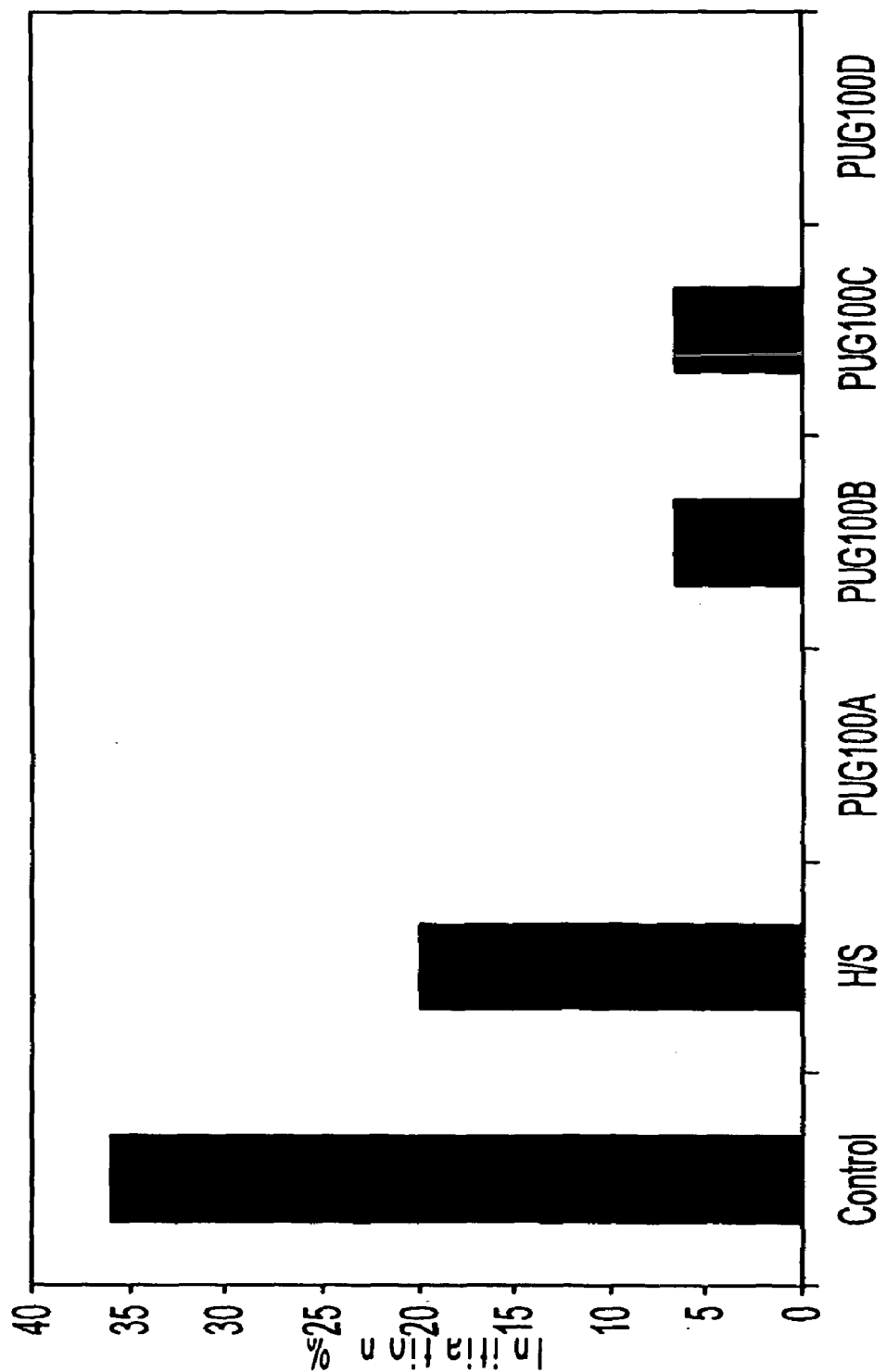
FIG. 20a illustrates the effect of four subfractions (PUG100A, PUG100B, PUG100C, and PUG100A) of the refined pomegranate fruit fraction PUG100, all at 0.1% w/w concentration, on the initiation of angiogenesis in human placental vein.
Figure 20B:
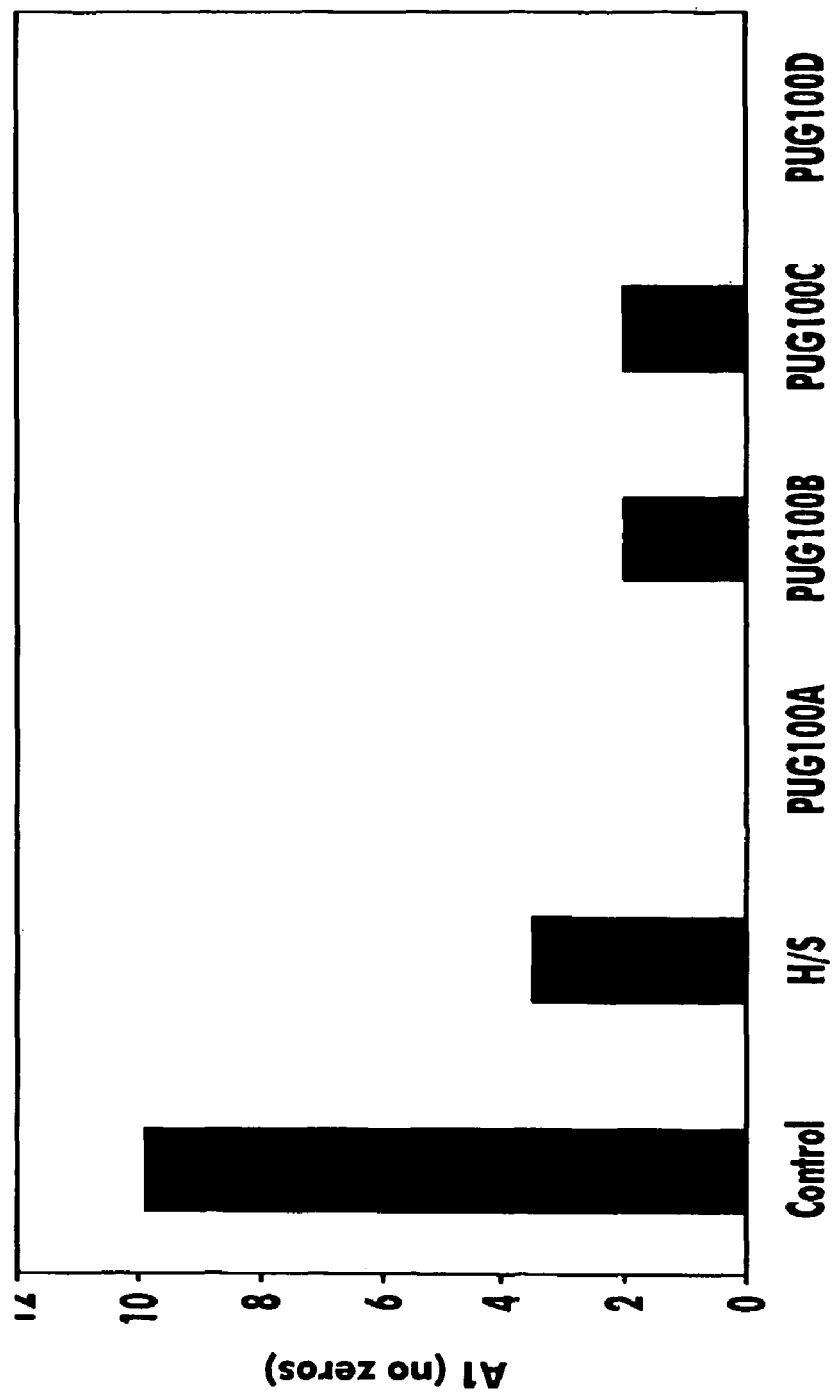
FIG. 20b illustrates the effect of four subfractions (PUG100A, PUG100B, PUG100C, and PUG100A) of the refined pomegranate fruit fraction PUG100, all at 0.1% w/w concentration, on angiogenesis in human placental vein discs as measured by an angiogenic index after removing discs with a zero angiogenic index (i.e., discs that never initiated an angiogenic response).
Figure 20C:
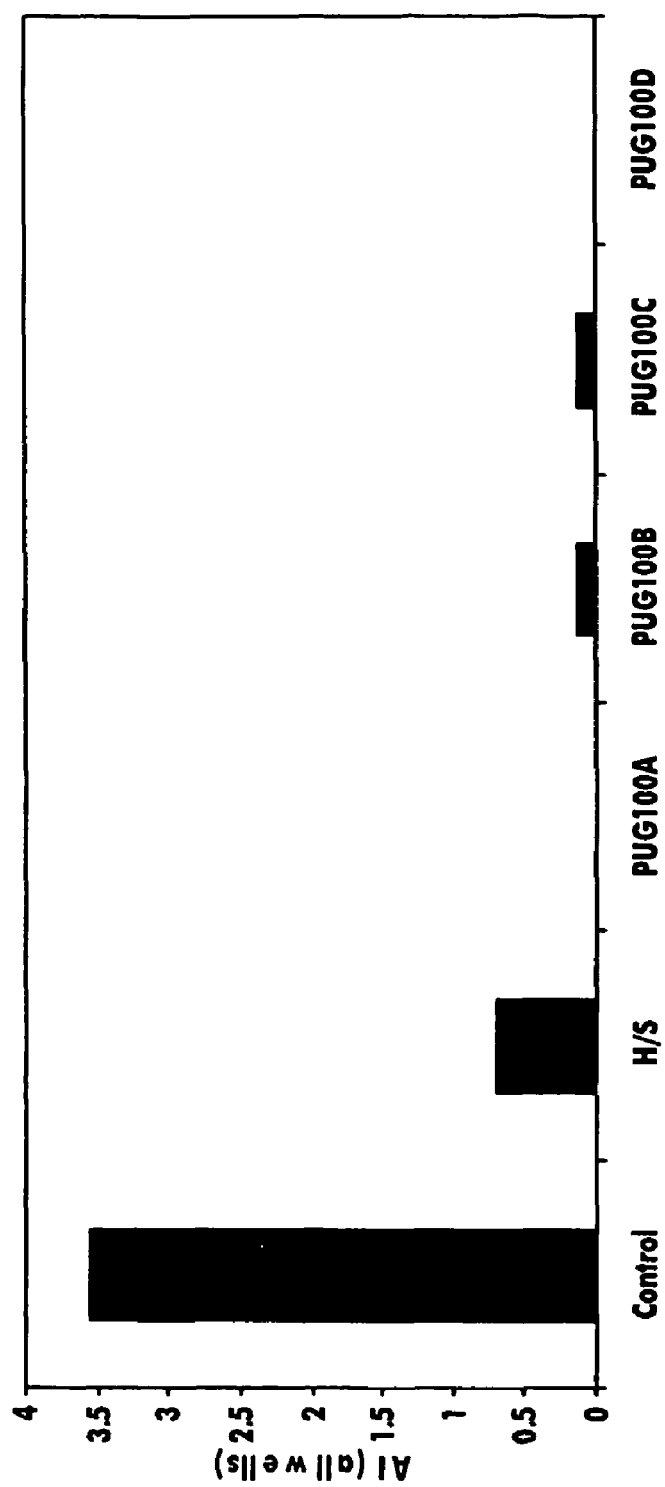
FIG. 20c illustrates the effect of four subfractions (PUG100A, PUG100B, PUG100C, and PUG100A) of the refined pomegranate fruit fraction PUG100, all at 0.1% w/w concentration, on angiogenesis (both initiation and proliferation) in human placental vein discs as measured by an angiogenic index.

To know if more than one active component were responsible for the anti-angiogenic activities, PUG100 was further sub-fractionated in a column chromatography based on a polarity separation mechanism. Two of the resulting four fractions, PUG100A and PUG100D displayed inhibitory concentration 100% ($IC_{100}$) at 0.1% w/v concentration in the angiogenesis assay. (FIGS. 20a, 20b, and 20c) These two fractions each blocked angiogenic initiation and subsequent growth of any already initiated blood vessels. Thus all four fractions showed some inhibition of angiogenesis, but the most active fractions were PUG100A and PUG100D.

Chemical Fingerprints of PUG-C, Its Fraction PUG100, and PUG100 Subfractions

Figure 21:
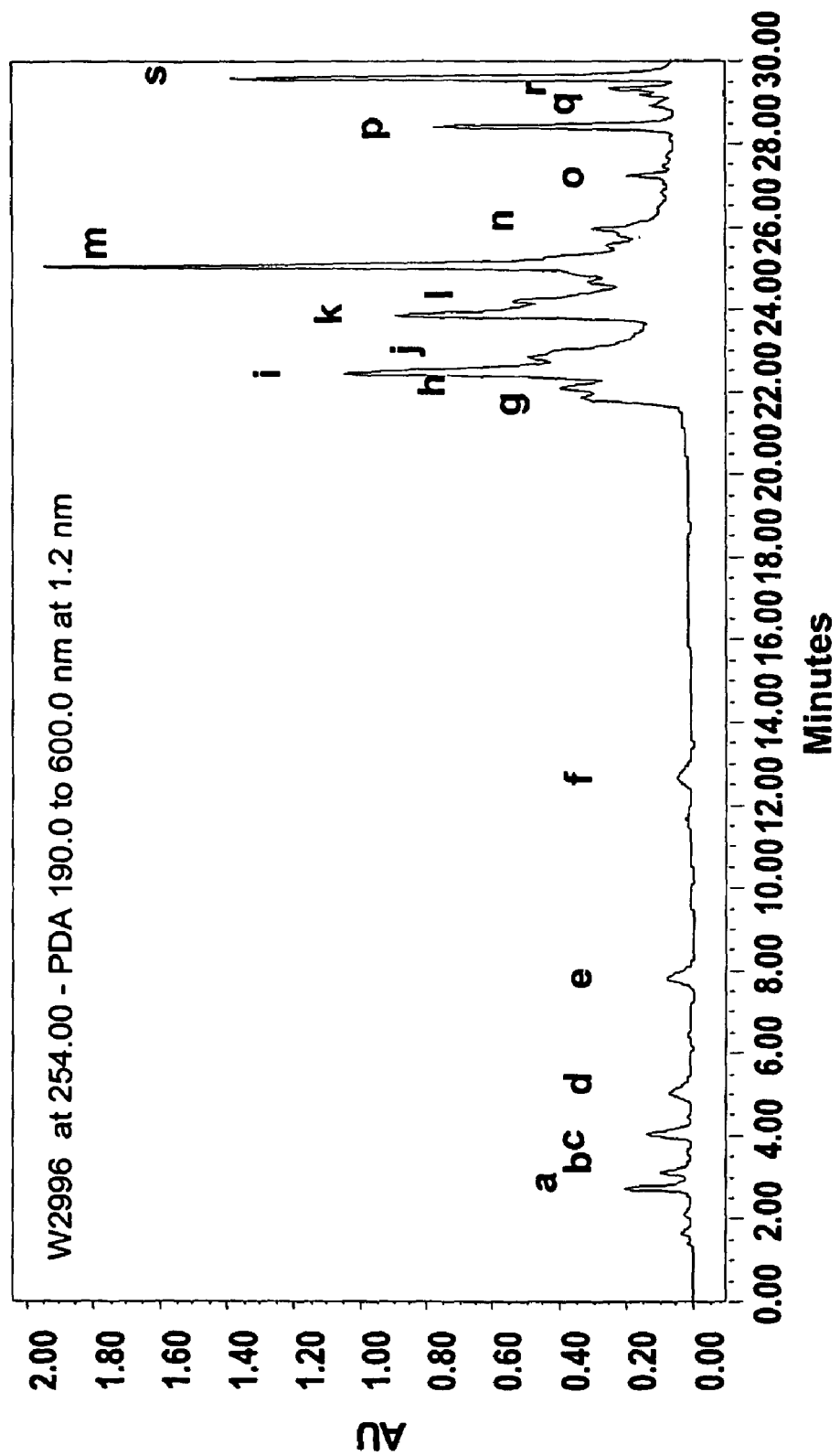
FIG. 21 illustrates a chromatogram of pomegranate fruit crude extract (PUG-C) developed using high performance liquid chromatography at 254 nm.

Pomegranate fruit extract and its fractions were analyzed in a high performance liquid chromatograph (HPLC). Chromatograms were developed on an HPLC system (Waters Delta 600, Waters Co., Milford, Mass.) consisting of a solvent delivery pump unit, an autosampler (Waters 717 plus), a UV-Vis (190 nm to 800 nm) diode array detector (Waters 2996 Photodiode Array Detector, 190 to 800 nm), an evaporative light-scattering detector (Waters 2420 ELSD), and an automatic fraction collector for preparative isolation work. The system is computer-controlled and analyzed with the Empower software. The HPLC system can conduct both analytical and preparative separations. The mobile phase consisted of HPLC-grade methanol and HPLC-grade acetic acid (0.15%) in water and was run using an isocratic elution at 5:95 (MeOH:$H_2O$) in the first 12 minutes, followed by a gradient elution to 100:0 for 14 minutes, a cleaning process for 4 minutes, and equilibrium to 5:95 for 15 minutes before a new sample is injected. The fingerprint of the pomegranate crude extract PUG-C is shown in FIG. 21. There are at least 19 identifiable components. In reality, there are more than 19 compounds in the crude pomegranate fruit extract since some peaks may not be a single compound, but rather a small cluster of compounds. Other components may be in extremely low concentrations and are easily hidden.

The isolated and purer anti-angiogenic fraction, PUG100, was much simpler in chemical composition. (FIG. 22) The fingerprint revealed 9 major components, a reduction from the 19 major components observed in the crude extract.

The HPLC fingerprints of the subfractions PUG100A, PUG100B, PUG100C and PUG100D from the polarity-based separation described above, revealed differences in major components. (FIGS. 23a, 23b, 23c, and 23d, respectively) As previously demonstrated in FIGS. 20a, 20b, and 20c, the refined fraction PUG100 contained two very active sub-fractions, PUG100A and PUG100D. PUG100A contained components 1 to 7, but no 9, whereas PUG100D contained almost all component 9, with a small amount of component 6. This indicates that at least two different anti-angiogenic compounds exist in the refined fraction PUG100.

Figure 24:
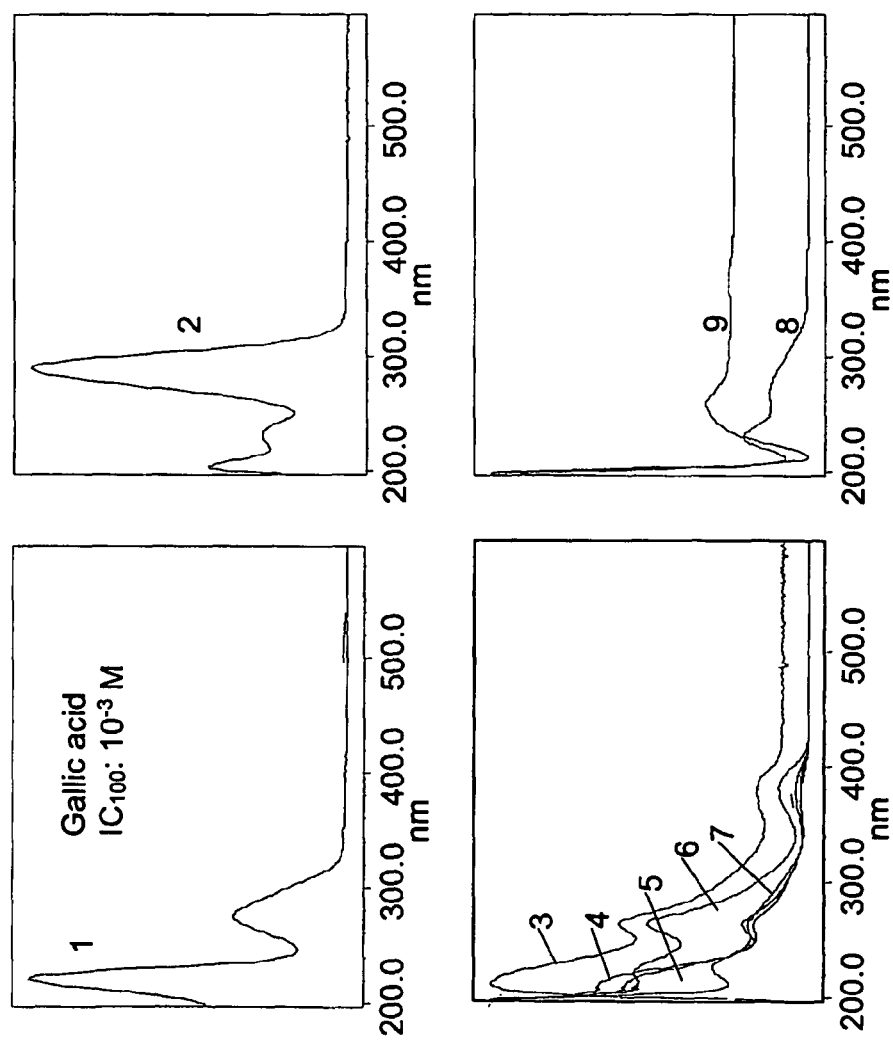
FIG. 24 illustrates the normalized UV absorption spectra of major components identified in the chromatogram of FIG. 22 of the pomegranate fruit refined extract (PUG100).

UV absorption spectral analysis over each of the major peaks in PUG100 revealed that 4 major groups of compounds might be present in the active pomegranate fraction PUG100 (FIG. 24). Group 1 consists of Peak 1 and is identified as gallic acid (gallotannins). Group 2 includes Peak 2 with strong peak absorption at 280 nm and might be phenolic acids (cinnamyl structure). Group 3 consists of Peaks 3 to 7 having two absorption peaks at 245 nm and 380 nm and might be flavonoids. Group 4 consists of Peaks 8 and 9 featuring weak absorption peaks between 220 nm and 260 nm and might be aliphatic, double-bonded compounds.

Figure 22:
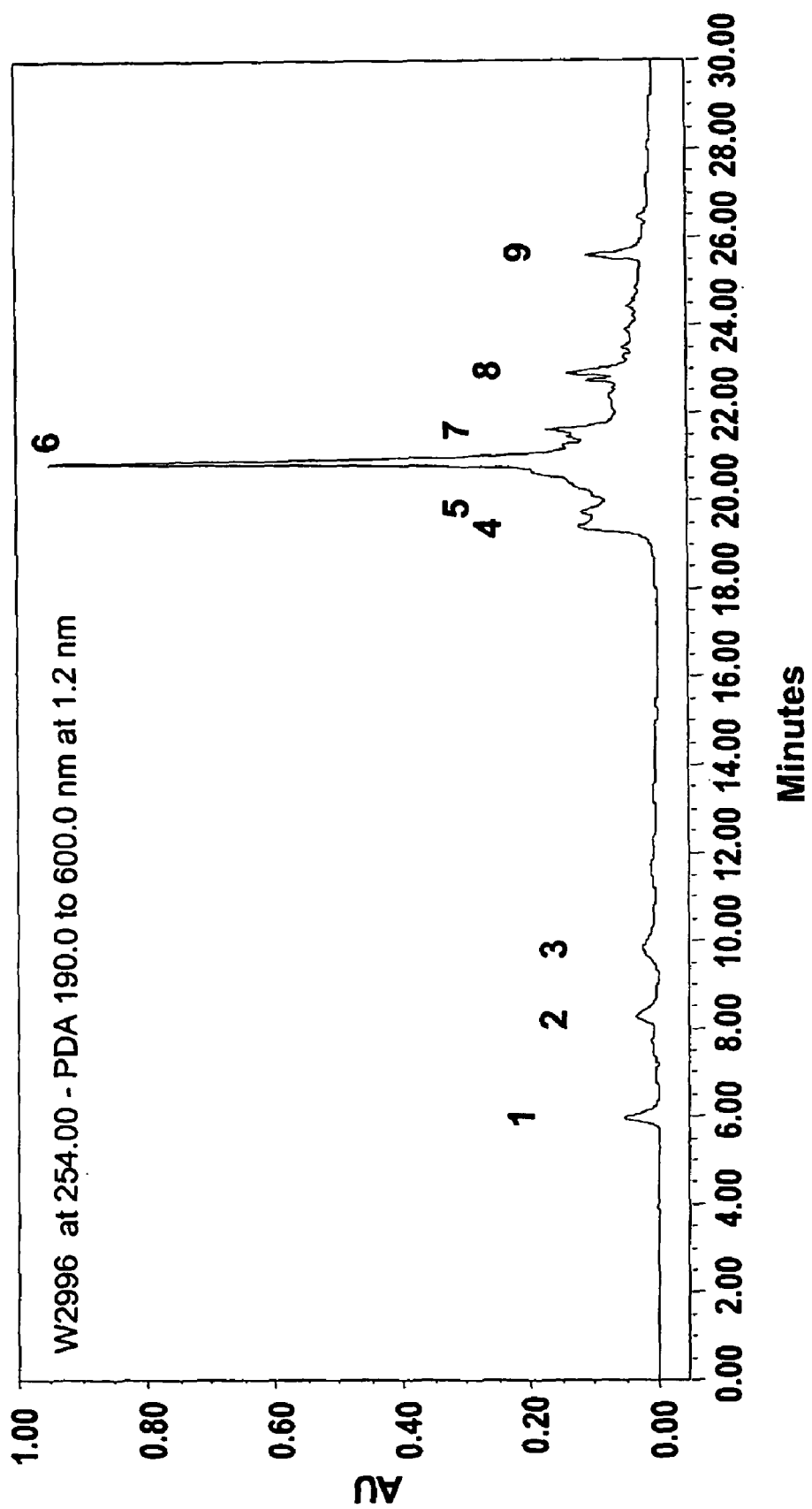
FIG. 22 illustrates a chromatogram of pomegranate fruit refined extract (PUG100) developed using high performance liquid chromatography at 254 nm.
Figure 23A:
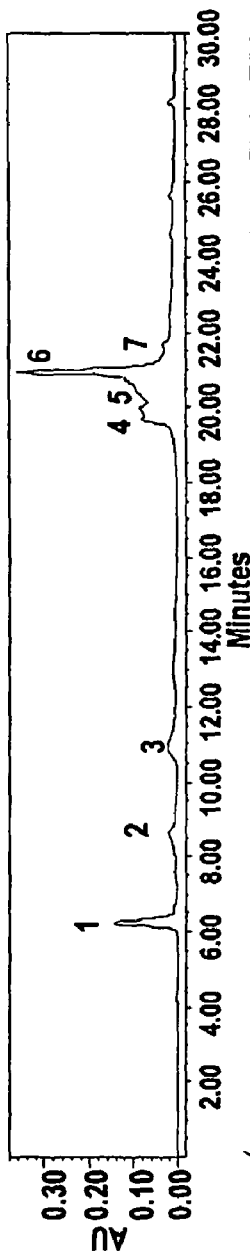
FIG. 23a illustrates a chromatogram of subfraction PUG100A of pomegranate fruit refined fraction (PUG100) developed using high performance liquid chromatography at 254 nm.
Figure 23B:
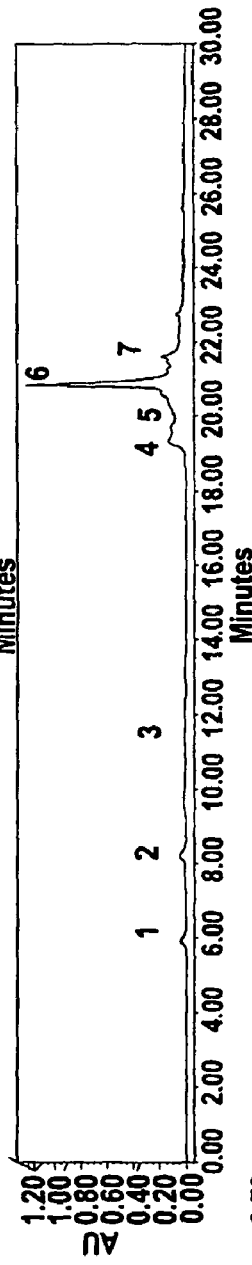
FIG. 23b illustrates a chromatogram of subfraction PUG100B of pomegranate fruit refined fraction (PUG100) developed using high performance liquid chromatography at 254 nm.
Figure 23C:
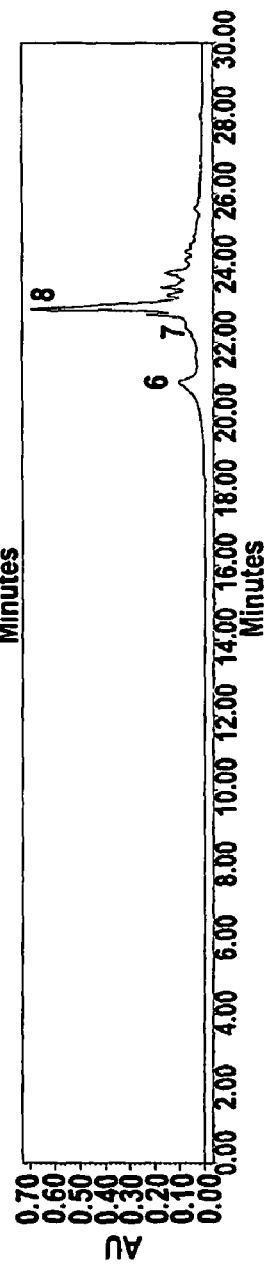
FIG. 23c illustrates a chromatogram of subfraction PUG100C of pomegranate fruit refined fraction (PUG100) developed using high performance liquid chromatography at 254 nm.
Figure 23D:
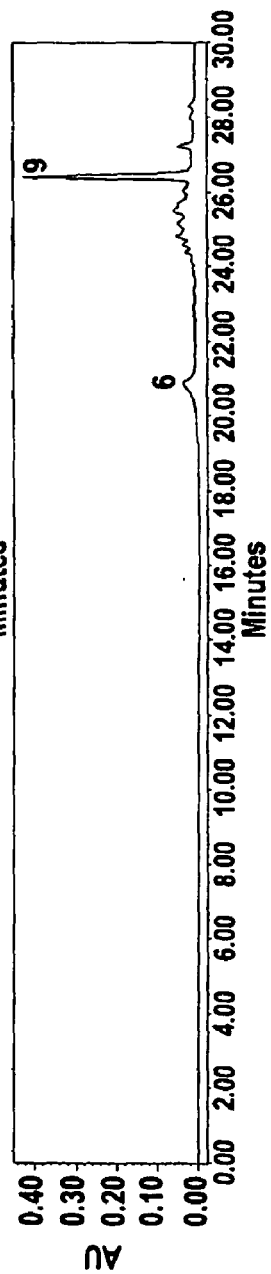
FIG. 23d illustrates a chromatogram of subfraction PUG100D of pomegranate fruit refined fraction (PUG100) developed using high performance liquid chromatography at 254 nm.

Quantitative analysis indicated that the refined fraction PUG100 contains 0.8% w/w gallic acid. At the $IC_{100}$ dose of 0.1% w/v (FIGS. 19a, 19b, and 19c), the concentration of gallic acid in PUG100 available to the test tissues was 0.00005 M (i.e. $IC_{100}$ for PUG100 gallic acid is $5 \times 10^{-5}$ M). Based on the gallic acid dose response analysis, PUG100 is 20-fold more potent than one would predict based on the gallic acid concentration. This means either that another compound has even greater anti-angiogenic activity than gallic acid, or that gallic acid and other compound(s) synergistically act to inhibit angiogenesis. Thus PUG100 is an active fraction (about 4% of the whole fruits) isolated from whole pomegranate fruit, that contains anti-angiogenic compounds that are small molecules (less than 2000 Daltons) based on the elution patterns, that are more soluble in ethanol than water, that contains some gallic acid, and that contains one or more compounds selected from the group consisting of gallotannins, phenolic acids (cinnamyl structures), flavonoids, and aliphatic, double-bonded compounds. PUG100 has a HPLC chemical fingerprint as shown in FIG. 22.

EXAMPLE 24

Inhibition of Human Fat Tissue Angiogenesis by PUG100 and by Gallic Acid

Figure 25A:
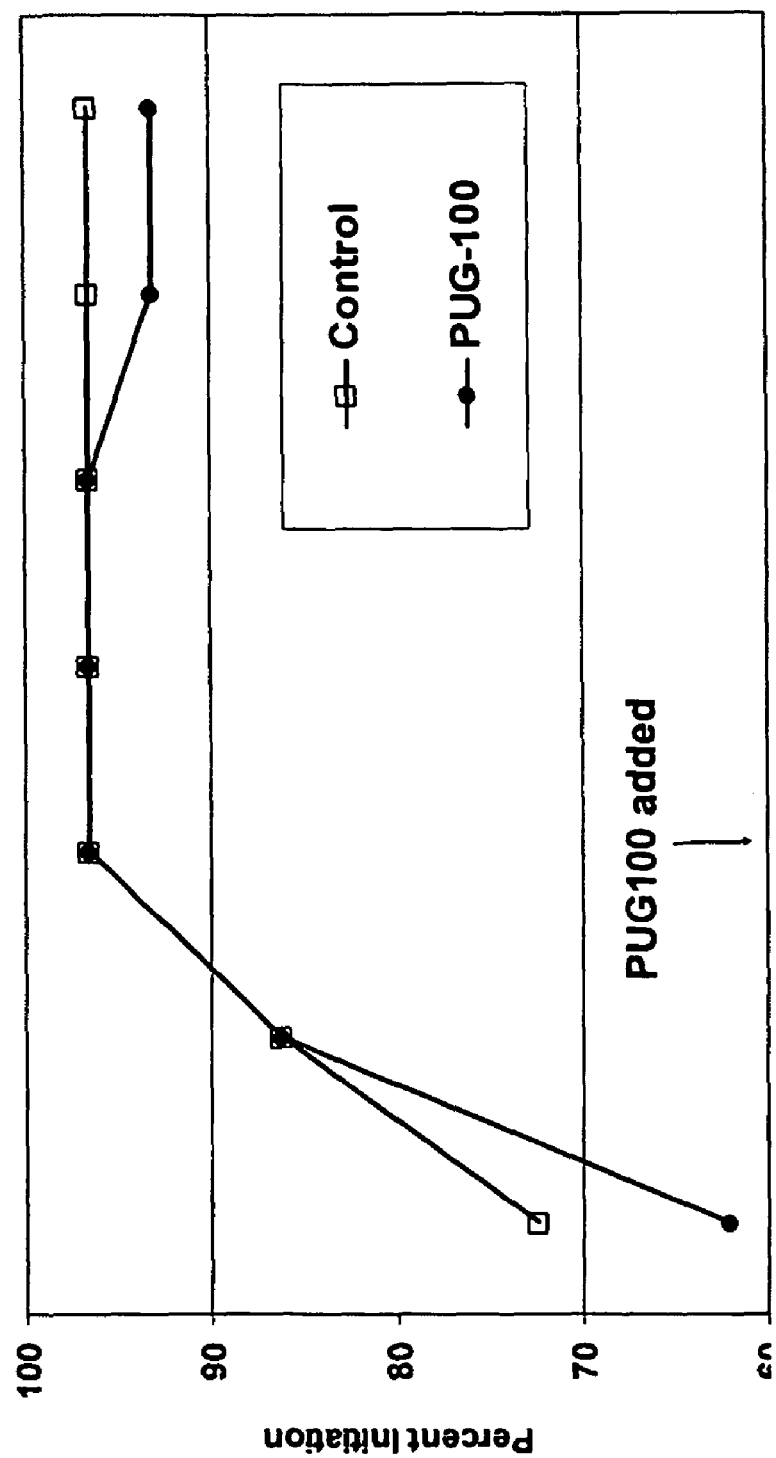
FIG. 25a illustrates the effect of pomegranate fruit refined extract (PUG100) at 0.01% w/v on the initiation of angiogenesis in human fat tissue discs.
Figure 25B:
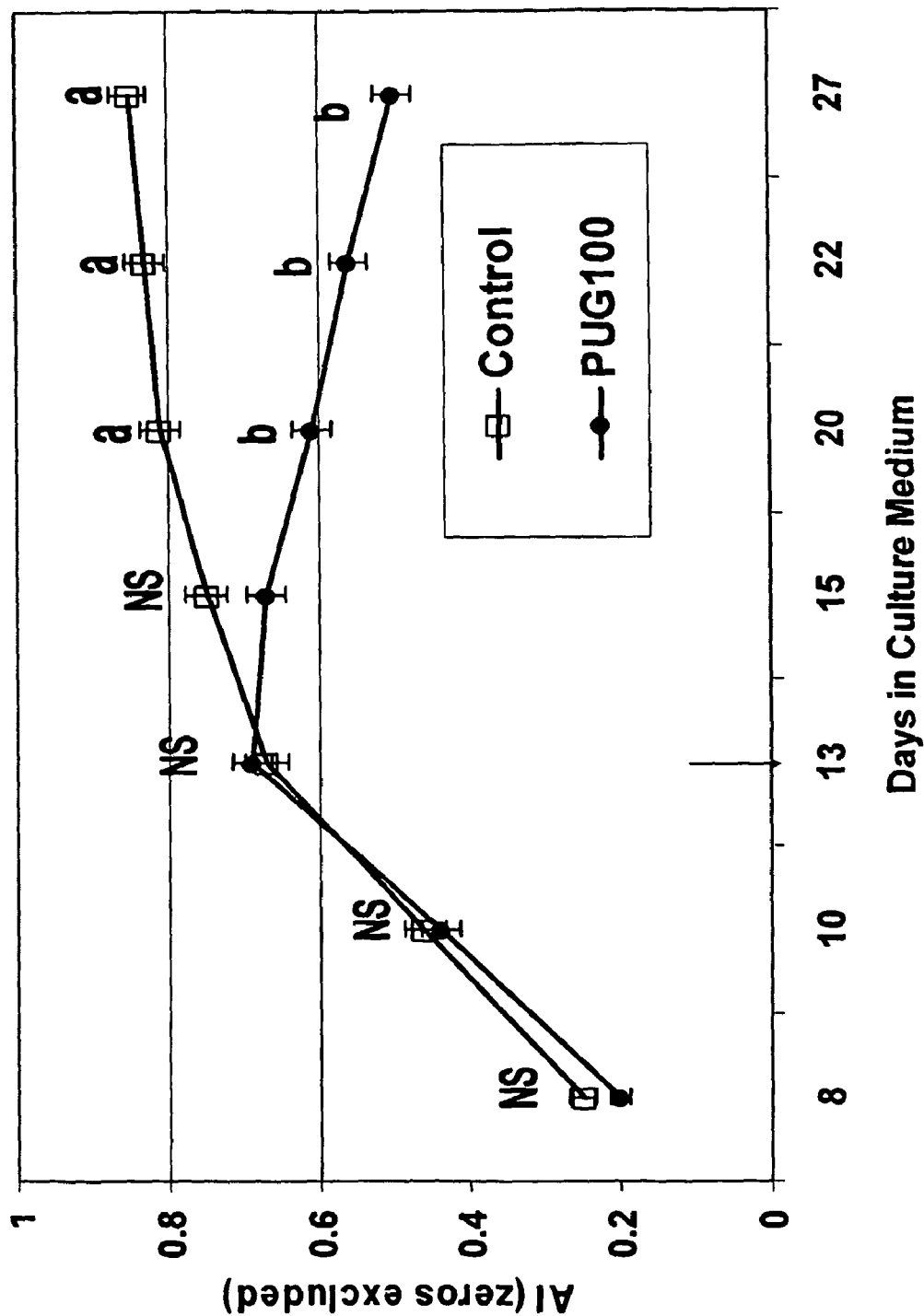
FIG. 25b illustrates the effect of pomegranate fruit refined extract (PUG100) at 0.01% w/v on angiogenesis in human placental vein discs as measured by an angiogenic index after removing discs with a zero angiogenic index (i.e., discs that never initiated an angiogenic response).

To test the angiogenic activity of plant extracts in another tissue, the refined fraction PUG100 was tested for its anti-angiogenic activity in human fat tissue taken from patients having gastric bypass surgery (Vista Surgical Hospital, Baton Rouge, La.). The human fat tissue assay was conducted very similar to that described in Example 1 for human placental vein tissue. The angiogenesis was first allowed to develop for 13 days when the refined fraction PUG100 at 0.1% w/v was added to the culture. A week of co-culture showed decreased angiogenic initiation, suggesting destruction of the already developed new blood vessels. (FIG. 25a). Immediately after the addition of the refined fraction PUG100, angiogenic vessel growth started to diverge. The control wells continued their growth, but the PUG100 treated wells stopped further growth. By Day 20, the angiogenic vessel growth was significantly reduced, strongly suggesting that the refined fraction PUG100 inhibited angiogenesis in the fat tissue. (FIG. 25b) In a separate dose study to determine the $IC_{100}$ dose of PUG100, PUG100 at 0.025% w/v completely suppressed angiogenic initiation, while PUG100 at 0.01% w/v showed an inhibition of 78% of the control growth. (Data not shown).

In another experiment, gallic acid at several concentrations was tested for inhibition of angiogenesis in the human fat tissue assay. Gallic acid at 0.01 M and 0.001 M inhibited initiation of angiogenesis in the fat tissue. (Data not shown). This indicates that these anti-angiogenic compounds inhibit angiogenesis in different tissues, and that these compounds could be used to decrease fat tissue mass either orally or by subcutaneous injection into the fat tissue.

EXAMPLE 25

Absorption in Rats of Orally Administered Refined Pomegranate Extract PUG-100

To determine the dose at which the anti-angiogenic PUG100 fraction is orally active, the anti-angiogenic activity of serum collected after oral administration to animals will be tested using the HPVAM assay as described above in Examples 1 and 13.

Thirty 300 gm male Sprague Dawley rats will be used. Each will be housed individually and fed rat chow ad libitum. After arrival rats will spend one week in quarantine before transfer into the experimental animal room. All rats will be adapted to gavaging over a 7-day period by daily gavage with sterile water, increasing the volumes from 0.2 ml to 1.0 ml over the 7-day period. One group (n=5) of rats will serve as a control, and receive only water vehicle. All other rats will be divided into five groups to receive one of four different doses of PUG-100 by oral gavage in 1.0 ml water vehicle or to received the lowest of the oral doses by intraperitoneal injection in a 0.9% saline vehicle (n=5 per group) daily for three consecutive days. The oral doses used will provide a 15-fold range of the extract from about 0.75 gm to about 12 gm of PUG-100 powder. All extracts will be vortexed and passed through a 0.2 μm filter before suspension in sterile water or saline. At the end of treatment, all rats will be anesthetized with nembutal and killed by guillotine for collection of trunk blood. The serum will be collected from the blood, and stored at −70° C. until used in the assay procedures. This serum will be tested in a 50%-50% mixture with FBS as the serum source in the HFAM assay.

A second experiment will be performed to test for any adverse effects. Twenty-four rats will be given either vehicle, low (effective oral dose determined by the above experiment) or high (double the low) dose pomegranate extract PUG100 daily (n=8 per group) by gastric intubation for 6 weeks after an initial 7-day adaptation period to the intubation procedure. Rats will be visually inspected daily for any signs of ill health. Changes in coat appearance, eyes, and any excretions will be noted. Body weights will be measured weekly. At the termination of the experiment, the rats will be anesthetized with nembutal (65 mg/kg), killed by guillotine, and trunk blood collected. Specific adipose depots (white and brown) will be weighed, as well as liver, kidney, spleen and gastrocnemius muscle. The body and tissues will be inspected for any gross anatomical or pathological changes. Samples of liver, kidney, spleen gut and stomach will be saved in formalin for future histopathological examination.

Blood will be collected for serum, which will be used for a full chemical panel plus insulin, corticosterone and leptin using standard commercially available immunoassays for rat. The panel will include glucose, triglyceride, total cholesterol, high-density lipoprotein, low-density lipoprotein, creatinine, blood urea nitrogen, calcium, magnesium, iron, potassium, alanine leucine transaminase, creatine phosphate kinase, alkaline phosphatase and albumin. These will be assayed by standard methods in a clinical chemistry laboratory. Remaining serum will be stored at −70° C. for 6 months.

It is expected that the serum from the gavaged rats will inhibit angiogenesis in the human fat tissue angiogenesis assay. The multiple doses will provide insight into the required levels for optimal oral activity. Comparison with the intraperitoneal administration of the extract will provide information on the absorption of the active components in the extracts and indicate whether a higher dose is needed in an oral form to be active. If the rate of response is not statistically different, either the serum volume in the assay (up to a maximum 40% concentration) will be increased, or the serum collected will be concentrated by freeze-drying and then reconstituted in a reduced volume.

EXAMPLE 26

Absorption in Humans of Orally Administered Refined Pomegranate Extract PUG-100

Using the information from Example 25, a human dose will be derived from the rodent data using the metabolic mass equation of mass raised to the 0.67 power as described by A. A. Heusner, "Energy metabolism and body size. I. Is the 0.75 mass exponent of the Kleiber's equation a statistical artifact?" Respiration Physiology, vol. 48, pp. 1-12 (1982). A PUG100 extract powder will be produced based on the procedure described above in Example 23, and will be capsulated in a commercial manufacturing facility with GMP compliance. Four subjects between 18 and 60 years with a BMI between 25 and 35 kg/m² who are otherwise healthy and on no chronic medications will be chosen to participate in this study. Subjects will have a medical history, physical examination, chemistry panel, urinalysis, CBC and electrocardiogram at screening. The first subject will come to the clinic after an overnight fast, and blood will be drawn at time −15, 0, 15, 30, 60, 90, 120, 180, 240, 360 and 480 min. The highest dose of PUG100 to be tested will be given orally with ½ glass of water at time 0, equivalent to 3.3 times the lowest effective dose equivalent in rodents as determined in Example 25. At time 0 the subject will void, and the urine will be discarded. Beginning at time 0, all the urine will be collected for 24 hours with the last voiding being 24 hours after time 0. As a safety measure, the subject will have a repeat chemistry panel, CBC, urinalysis, electrocardiogram and brief physical examination 24 hours following the dose of PUG100 when the 24-hour urine is returned. The blood and urine will be assayed for angiogenic activity or for the chemical profile of the two compounds active in inhibiting angiogenesis. This information from the serum will be used to determine the maximal concentration of PUG100, its timing and its half-life in the serum. The urinary measures will be used to determine the minimal amount absorbed from the gastrointestinal tract.

The time points to be used for the testing of the subsequent three subjects will be decided based on the results of the first subject's results. The test curves at the three different doses will be used to calculate the time of the maximal concentration and the half-life of the active compounds in the blood stream. The 24-hour urine will be used to determine the minimal amount of PUG100 absorbed from the gastrointestinal tract. The serum activity will be confirmed at the time of the maximal concentration by testing the serum in the human fat tissue angiogenesis assay. Subjects will have a brief physical exam, CBC, chemistry panel, urinalysis and electrocardiogram 24 hours before and after each dose of PUG100. Each of the three doses will be separated by 1 week as a safety measure when the 24-hour urine is returned.

It is expected that the above procedures will give a minimal estimate of the amount of PUG100 absorbed from the gastrointestinal tract. It is also expected that the timing and maximal concentration in relation to dose of the active compounds in PUG100 will be defined. It is also anticipated that knowing the half-life and the dose response relationship, the best dose and the dosing frequency for the subsequent pilot clinical trial will be estimated.

EXAMPLE 27

Efficacy of PUG100 in Causing Weight Loss in Humans

To test the ability of the PUG100 extract to cause weight loss in humans, human volunteers will be used. Prior to the pilot trial, four subjects will be enrolled in a 1-week repeated dose safety trial. Four subjects between 18 and 60 years of age with a BMI between 25 and 35 kg/m² who are otherwise healthy and on no chronic medications will participate in this study. Subjects will have a medical history, physical examination, chemistry panel, urinalysis, CBC and electrocardiogram at screening. They will be given the dose of PUG100 to be used in the pilot study over the course of 1-week. At the end of the week, the physical examination, blood tests, urinalysis and electrocardiogram will be repeated. Confirmation of the safety of PUG100 will lead to a 12-week pilot clinical trial.

The pilot trial will enroll 20 healthy subjects between the ages of 18 and 60 years of age with a BMI between 25 and 35 kg/m². Subjects will be healthy and on no chronic medication other than birth control pills or hormone replacement therapy. Subjects with the potential to bear children will be on an effective contraceptive, and women who are nursing or pregnant will be excluded. At screening, subjects will have a medical history, physical examination, chemistry panel, CBC, electrocardiogram and a urinalysis. Subjects will be randomized in a 1:1 fashion to PUG100 or a placebo, and at the time of randomization subjects will be instructed in a 1200 Kcal/d diet for women and a 1500 kcal/d diet for men. Subjects will also be given a sheet with suggestions for lifestyle change and be asked to walk 30 min most days of the week. Subjects will be seen at week 1, 2 and then every 2 weeks for the 12 weeks of the trial. On those visits during the trial subjects will be questioned about adverse events, vital signs will be measured, and weight will be taken. At the final visit at 12 weeks the physical examination, chemistry panel, CBC, urinalysis and electrocardiogram will be repeated.

This study is designed as a pilot trail to develop data needed to determine the number of subjects required for a definitive clinical trial with the power to detect a difference at 80% probability with an alpha of 0.05.

It is expected that in the pilot study the standardized PUG100 will give a weight loss of 4% or greater that is numerically greater than the placebo weight loss which is anticipated to be between 1-2%. This would be predicted to give a medically significant weight loss of >5% at the six-month plateau seen in most weight loss studies.

Miscellaneous

The term "active plant extract" is defined as an extract from a plant that has been shown to be angiogenic or that contains sufficient gallic acid to either inhibit angiogenesis or to degrade existing capillary networks. The active plant extract is an extract from a plant selected from the group consisting of *Rubus* spp.; *Rubus suavissimus* (Sweet leaf tea; Chinese blackberry); *Rubus occidentalis* (North American black raspberry); *Rubus laciniatus* (European cut-leaved blackberry); *Rubus ursinus* (Pacific blackberry or dewberry); *Rubus fruticosus* (Blackberry); *Rubus idaeus* (Raspberry); *Rubus chingii* Hu; *Rubus parviflorus* (thimbleberry); *Diospyros khaki* L. (persimmon); *Punica granatum* L. (Pomegranate); *Abrus prccatorius* L.; *Acacia catechu* (L.) Willd.; *Ampelopsis brevipedunculata*; *Ampelopsis japonica*; *Coriaria sinica* Maxim.; *Cornus officinalis* Sieb. et Zucc. (dogwood); *Cotinus coggygria* Scop. (Smokebush); *Daucus carota* L. var. *Sativa* DC.; *Erodium stephanianum* Willd.; *Eucalyptus robusta* Sm.; *Euonymus bungeanus* Maxim. (Winterberry Euonymus); *Euphorbia humifusa* Wild. (Wolf's milk); *Geranium pratense* L.; *Geranium wilfordii* Maxim. (Heron's Bill); *Juglans regia* L.; *Loropetalum chinensis* (R. Br.) Oliv. (Chinese fringe tree); *Lythrum salicaria* L.; *Malus* spp. (Apple); *Mangifera indica* L. (Mango); *Macrocarpium officinale* Sieb. et Zucc.; *Passiflora caerulea* L.; *Pharbitis nil* (L.) Choisy; *Phyllanthus emblica* L.; *Pistacia chinensis* Bge.; *Platycarya longipes* Wu.; *Platycarya strobilacea* Sieb. et Zucc. (Australia cheesewood); *Polygonum aviculare* L.; *Polygonum bistorta* l. (Bistort); *Psidium guajava* L. (guava); *Quercus infectoria* Oliver; *Rheum officinale* Baill.; *Rheum palmatum* L. (rhubarb); *Rheum tanguticum* Maxim. Ex Reg.; *Rhus chinensis* Mill. (Chinese sumac gallnut); *Rhus potaninii* Maxim. (Sumac gallnut); *Rosa chinensis* Jacq. (Mini rose); *Rosa rugosa* Thunb. (Rose); *Rubus ulmifolius*; *Rumex japonicus* Houtt. (Japanese dock); *Sanguisorba officinalis* L. (Burnet); *Sapium sebiferum* (L.) Roxb.; *Syzygium cumini* (L.) Skeels; *Tamarix chinensis* Lour.; *Terminalia chebula* Retz. (Medicine terminalia); *Tetrastigma hypoglaucum* Planch.; and *Tussilago farfara* L.

The term "therapeutically effective amount" as used herein refers to an amount of gallic acid (or its derivatives) or of an "active plant extract" sufficient either to inhibit angiogenesis or to degrade existing capillary networks to a statistically significant degree (p<0.05). The term "therapeutically effective amount" therefore includes, for example, an amount sufficient to prevent the growth of angiogenic vessels found in diseases of tumor growth, diabetic retinopathy, psoriasis, retinopathy of prematurity, rheumatoid arthritis, and obesity, and preferably to reduce by at least 50%, and more preferably to reduce by at least 90%, the amount of angiogenesis. The dosage ranges for the administration of gallic acid or the active plant extract are those that produce the desired effect. Generally, the dosage will vary with the age, weight, condition, sex of the patient, type of tumor or other pathology, the degree of tumor development, and the degree of angiogenic response. A person of ordinary skill in the art, given the teachings of the present specification, may readily determine suitable dosage ranges. The dosage can be adjusted by the individual physician in the event of any contraindications. In any event, the effectiveness of treatment can be determined by monitoring the extent of angiogenic inhibition or remission by methods well known to those in the field. Moreover, gallic acid or the active plant extract can be applied in pharmaceutically acceptable carriers known in the art. Gallic acid or the active plant extract can be used to treat cancers in animals and in humans in vivo. The application can be oral, by injection, or topical, providing that in an oral administration gallic acid or the active plant extract is preferably protected from digestion.

Gallic acid or the active plant extract may be administered to a patient by any suitable means, including oral, parenteral, subcutaneous, intrapulmonary, topically, and intranasal administration. Parenteral infusions include intramuscular, intravenous, intraarterial, intraperitoneal or intravitreal administration. Additionally, the infusion could be into an organ or tumor or site of disease. Injection of gallic acid or its active plant extract may include the above infusions or may include intraperitonieal, intravitreal, direct injection into a tumor, or direct injection into a site of angiogenic disease. Gallic acid or the active plant extract may also be administered transdermally, for example in the form of a slow-release subcutaneous implant, or orally in the form of capsules, powders, or granules. Although direct oral administration may cause some loss of anti-angiogenic activity, gallic acid or the active plant extract could be packaged in such a way to protect the active ingredient(s) from digestion by use of enteric coatings, capsules or other methods known in the art.

Pharmaceutically acceptable carrier preparations for parenteral administration include sterile, aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, emulsions or suspensions, including saline and buffered media. Parenteral vehicles include sodium chloride solution, Ringer's dextrose, dextrose and sodium chloride, lactated Ringer's, or fixed oils. The active therapeutic ingredient may be mixed with excipients that are pharmaceutically acceptable and are compatible with the active ingredient. Suitable excipients include water, saline, dextrose, and glycerol, or combinations thereof. Intravenous vehicles include fluid and nutrient replenishers, electrolyte replenishers, such as those based on Ringer's dextrose, and the like. Preservatives and other additives may also be present such as, for example, antimicrobials, anti-oxidants, chelating agents, inert gases, and the like.

The form may vary depending upon the route of administration. For example, compositions for injection may be provided in the form of an ampule, each containing a unit dose amount, or in the form of a container containing multiple doses. Direct injections into a tumor tissue or fat mass would be the most direct way to deliver the anti-angiogenic compounds to the target tissue.

Gallic acid or the active plant extract may be formulated into therapeutic compositions as pharmaceutically acceptable salts. These salts include the acid addition salts formed with inorganic acids such as, for example, hydrochloric or phosphoric acid, or organic acids such as acetic, oxalic, or tartaric acid, and the like. Salts also include those formed from inorganic bases such as, for example, sodium, potassium, ammonium, calcium or ferric hydroxides, and organic bases such as isopropylamine, trimethylamine, histidine, procaine and the like.

Controlled delivery may be achieved by admixing the active ingredient with appropriate macromolecules, for example, polyesters, polyamino acids, polyvinyl pyrrolidone, ethylenevinylacetate, methylcellulose, carboxymethylcellulose, prolamine sulfate, or lactide/glycolide copolymers. The rate of release of gallic acid or the active plant extract may be controlled by altering the concentration of the macromolecule.

Controlled delivery can also be achieved by conjugating gallic acid with a known compound that targets cellular surface receptors that are known to be unique to angiogenic blood vessels, e.g., somatostatin and its analogs and derivatives (binding to somatostatin receptor subtype 2), platelet-derived growth factor (binding to platelet derived growth factor receptor), and vascular endothelial growth factor (binding to a kdr receptor). See M. O. Meyers et al, "Gene upregulation of PDGF in human angiogenesis," abstract presented at Association for Academic Surgery, 1998; J. C. Watson et al., "SST-2 gene expression appears during human angiogenesis," abstract published in Regul. Peptides, vol. 64, pp. 206 (1996); J. C. Watson et al., "Initiation of kdr gene transcription is associated with conversion of human vascular endothelium to an angiogenic phenotype," Surgical Forum, vol. 47, pp. 462-464 (1996); and J. C. Watson et al., "Growing vascular endothelial cells express somatostatin subtype 2 receptors," British Journal of Cancer, vol. 85, pp. 266-272 (2001).

Another method for controlling the duration of action comprises incorporating gallic acid or the active plant extract into particles of a polymeric substance such as a polyester, peptide, hydrogel, polylactide/glycolide copolymer, or ethylenevinylacetate copolymers. Alternatively, gallic acid or the active plant extract may be encapsulated in microcapsules prepared, for example, by coacervation techniques or by interfacial polymerization, for example, by the use of hydroxymethylcellulose or gelatin-microcapsules or poly(m-ethylmethacrylate) microcapsules, respectively, or in a colloid drug delivery system. Colloidal dispersion systems include macromolecule complexes, nanocapsules, microspheres, beads, and lipid-based systems including oil-in-water emulsions, micelles, mixed micelles, and liposomes.

Gallic acid (or its derivates) could be administered as glyceryl trigallate. Gallic acid is a small molecule that is absorbed when taken orally. Large amounts of gallic acid could result in a large acid or salt load. Three gallic acid molecules (or its derivatives) could be attached to glycerol by ester bonds and would allow safe delivery of gallic acid without potential for an increase in acid or salt load. Since esterases are abundant in the gastrointestinal tract and in tissue, the glyceryl trigallate should be rapidly broken down into two food products, gallic acid and glycerol.

The present invention provides a method of preventing, treating, or ameliorating a disease that causes an angiogenic response in the body such as retinopathy and psoriasis, comprising administering to a subject at risk for a disease or displaying symptoms for such disease, a therapeutically effective amount of gallic acid, a gallic acid derivative, or an active plant extract. The term "ameliorate" refers to a decrease or lessening of the symptoms or signs of the disorder being treated. The symptoms or signs that may be ameliorated include those associated with an increase in angiogenesis in the body. The term "substantially similar" is understood by a person skilled in the art to refer to the possibility that small differences in factors and concentrations of factors may exist between two compositions even after following the same extraction procedure, but that these small differences do not affect the antiangiogenic properties as measured in the original composition.

The complete disclosures of all references cited in this specification are hereby incorporated by reference. In the event of an otherwise irreconcilable conflict, however, the present specification shall control.

What is claimed:

1. An anti-angiogenic composition, wherein said composition is more soluble in ethanol than in water; contains compounds having a molecular weight less than 2000 Daltons; comprises gallic acid or a derivative of gallic acid; is identical to a composition that elutes from an aqueous extract of black raspberry fruit with about 51% to about 95% ethanol from a polystyrene resin column with a pore size of 46 Å; inhibits angiogenesis; and has a chemical fingerprint on high performance liquid chromatography as shown in FIG. 17.

2. The composition as recited in claim 1, additionally comprising one or more different antiangiogenic compounds selected from the group consisting of a derivative of gallic acid, an active plant extract that is not from black raspberry, angiostatin, endostatin, platelet factor-4, TNP-470, thalidomide, interleukin-12, antibodies to fibroblast growth factor or vascular endothelial growth factor, suramin and its analogs, tecogalan, and somatostatin and its analogs.

3. A method of ameliorating or inhibiting angiogenesis in a mammal, said method comprising administering to the mammal a therapeutically effective amount of a composition as recited in claim 1.

4. The method of claim 3, wherein the angiogenesis is associated with a disease.

5. The method of claim 4, wherein the angiogenic-associated disease is selected from the group consisting of diabetic retinopathy, macular degeneration, obesity, systemic lupus erythematosis, psoriasis, rheumatoid arthritis, retinopathy of prematurity, corneal neovascularization, malignant tumor growth beyond 2 mm, benign tumors, hemangioma, arterial/venous malformations, sickle cell anemia, sarcoidosis, Pagets disease, vein occlusion in the eye, mycobacterial infection, systemic lupus erythematosis, uveitis, infections of the retina, myopia, primary hyperparathyroidism, secondary hyperparathyroidism, and tertiary hyperparathyroidism.

6. The method of claim 4, wherein the disease is a non-malignant disease.

7. The method of claim 5, wherein the disease is obesity.

8. The method of claim 5, wherein the disease is corneal neovascularization.

9. The method of claim 5, wherein the disease is psoriasis.

10. The method of claim 3, wherein the ameliorating or inhibiting of angiogenesis inhibits the growth of a malignant tumor greater than 2 mm in diameter.

11. The method of claim 3, wherein said administration is by injection.

12. The method of claim 3, wherein said administration is orally.

13. The method of claim 3, wherein said mammal is a human.

14. The method of claim 3, wherein the ameliorating or inhibiting of angiogenesis substantially decreases adipose fat tissue mass.

15. The method of claim 14, wherein the administration is by subcutaneous injection into the fat tissue.

16. The method of claim 3, additionally comprising administering one or more different compounds selected from the group consisting of gallic acid and its derivatives, an active plant extract that is not extracted from black raspberry, angiostatin, endostatin, platelet factor-4, TNP-470, thalidomide, interleukin-12, antibodies to fibroblast growth factor or vascular endothelial growth factor, protein kinase inhibitors, suramin and its analogs, tecogalan, somatostatin and its analogs, radiolabeled somatostatin, rad iolabeled somatostatin analogs, radiation octreotide, tubulin inhibitors, and interferon.

17. A method of decreasing the size of an existing capillary network in a mammal, wherein the growth and maintenance of the network depends on angiogenesis, said method comprising administering to the mammal a therapeutically effective amount of a composition as recited in claim 1.

18. The method of claim 17, wherein the capillary network is associated with a disease.

19. The method of claim 18, wherein the capillary network-associated disease is selected from the group consisting of diabetic retinopathy, macular degeneration, obesity, systemic lupus erythematosis, psoriasis, rheumatoid arthritis, retinopathy of prematurity, corneal neovascularization, malignant tumor growth beyond 2 mm, benign tumors, hemangioma, arterial/venous malformations, sickle cell anemia, sarcoidosis, Pagets disease, vein occlusion in the eye, mycobacterial infection, systemic lupus erythematosis, uveitis, infections of the retina, myopia, primary hyperparathyroidism, secondary hyperparathyroidism, and tertiary hyperparathyroidism.

20. The method of claim 18, wherein the disease is a non-malignant disease.

21. The method of claim 19, wherein the disease is obesity.

22. The method of claim 18, wherein the existing capillary network is due to corneal neovascularization.

23. The method of claim 19, wherein the disease is psoriasis.

24. The method of claim 17, wherein said administration is by injection.

25. The method of claim 17, wherein said administration is orally.

26. The method of claim 17, wherein said mammal is a human.

27. The method of claim 17, wherein the capillary network is associated with a malignant tumor greater than 2 mm, and wherein decreasing the capillary network decreases the growth and size of said tumor.

28. The method of claim 17, wherein the existing capillary network is associated with adipose fat tissue, and wherein decreasing the capillary network decreases the adipose fat tissue.

29. The method of claim 28, wherein the administration is by subcutaneous injection into the fat tissue.

30. The method of claim 17, additionally comprising administering one or more different compounds selected from the group consisting of gallic acid and its derivatives, an active plant extract that is not extracted from black raspberry, angiostatin, endostatin, platelet factor-4, TNP-470, thalidomide, interleukin-12, antibodies to fibroblast growth factor or vascular endothelial growth factor, protein kinase inhibitors, suramin and its analogs, tecogalan, somatostatin and its analogs, rad iolabeled somatostatin, radiolabeled somatostatin analogs, radiolabeled octreotide, tubulin inhibitors, and interferon.

31. The composition of claim 2, wherein the gallic acid derivative is selected from a list consisting of tannic acid, methyl gallate, propyl gallate, butyl gallate, octyl gallate, ethyl gallate, lauryl gallate, ellagic acid, BUSMUTH-gallate, galloyl glucose, di-galloyl glucose, tri-galloyl glucose, tetra-galloyl glucose, penta-galloyl glucose, and glyceryl trigallate.

* * * * *